(12) United States Patent
Wong et al.

(10) Patent No.: US 12,168,680 B2
(45) Date of Patent: *Dec. 17, 2024

(54) FUSION MOLECULES AND IL-15 VARIANTS

(71) Applicant: Altor BioScience LLC, Culver City, CA (US)

(72) Inventors: Hing C. Wong, Culver City, CA (US); Peter Rhode, Culver City, CA (US); Xiaoyun Zhu, Culver City, CA (US); Kai-Ping Han, Culver City, CA (US)

(73) Assignee: Altor Bioscience, LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/305,965

(22) Filed: Apr. 24, 2023

(65) Prior Publication Data

US 2023/0257437 A1 Aug. 17, 2023

Related U.S. Application Data

(63) Continuation of application No. 17/716,986, filed on Apr. 8, 2022, now Pat. No. 11,673,932, which is a continuation of application No. 16/654,958, filed on Oct. 16, 2019, now Pat. No. 11,365,231, which is a continuation of application No. 15/254,713, filed on Sep. 1, 2016, now Pat. No. 10,450,359, which is a continuation of application No. 13/946,438, filed on Jul. 19, 2013, now Pat. No. 9,464,127, which is a continuation of application No. 12/151,980, filed on May 9, 2008, now Pat. No. 8,492,118.

(60) Provisional application No. 60/928,900, filed on May 11, 2007.

(51) Int. Cl.
| | |
|---|---|
| A61K 38/20 | (2006.01) |
| A61K 38/17 | (2006.01) |
| C07K 14/54 | (2006.01) |
| C07K 14/715 | (2006.01) |
| C07K 14/725 | (2006.01) |
| C07K 16/28 | (2006.01) |
| C12N 15/09 | (2006.01) |
| C12N 15/62 | (2006.01) |
| G01N 33/569 | (2006.01) |
| A61K 38/00 | (2006.01) |
| C07K 16/18 | (2006.01) |
| C12P 21/00 | (2006.01) |

(52) U.S. Cl.
CPC ...... *C07K 14/5443* (2013.01); *A61K 38/1774* (2013.01); *A61K 38/1793* (2013.01); *A61K 38/2086* (2013.01); *C07K 14/7051* (2013.01); *C07K 14/7155* (2013.01); *C07K 16/28* (2013.01); *C12N 15/09* (2013.01); *C12N 15/62* (2013.01); *G01N 33/56977* (2013.01); *A61K 38/00* (2013.01); *C07K 16/18* (2013.01); *C07K 2319/00* (2013.01); *C07K 2319/31* (2013.01); *C07K 2319/33* (2013.01); *C07K 2319/74* (2013.01); *C07K 2319/75* (2013.01); *C12P 21/00* (2013.01)

(58) Field of Classification Search
None
See application file for complete search history.

(56) References Cited

U.S. PATENT DOCUMENTS

| | | | |
|---|---|---|---|
| 5,116,964 A | 5/1992 | Capon et al. | |
| 5,288,931 A | 2/1994 | Chang et al. | |
| 5,541,087 A | 7/1996 | Lo et al. | |
| 5,620,939 A | 4/1997 | Halasa et al. | |
| 6,344,192 B1 | 2/2002 | Grooten et al. | |
| 7,112,660 B1 | 9/2006 | Domingues et al. | |
| 8,124,084 B2 | 2/2012 | Lefrancois et al. | |
| 8,163,879 B2 | 4/2012 | Wong et al. | |
| 8,492,118 B2 | 7/2013 | Wong et al. | |
| 8,507,222 B2 | 8/2013 | Wong et al. | |
| 8,940,288 B2 | 1/2015 | Lefrancois et al. | |
| 8,940,289 B2 | 1/2015 | Wong et al. | |
| 9,255,141 B2 | 2/2016 | Wong et al. | |
| 9,328,159 B2 | 5/2016 | Wong et al. | |
| 9,365,630 B2 | 6/2016 | Lefrancois et al. | |
| 9,428,573 B2 | 8/2016 | Wong et al. | |
| 9,464,127 B2 | 10/2016 | Wong et al. | |
| 9,593,152 B2 | 3/2017 | Wong et al. | |
| 9,925,247 B2 | 3/2018 | Klu et al. | |
| 10,150,805 B2 | 12/2018 | Wong et al. | |
| 10,358,478 B2 | 7/2019 | Wong et al. | |
| 10,450,359 B2 | 10/2019 | Wong et al. | |
| 10,537,615 B2 | 1/2020 | Klu et al. | |
| 10,865,230 B2 | 12/2020 | Liu et al. | |

(Continued)

FOREIGN PATENT DOCUMENTS

| | | |
|---|---|---|
| AU | 2008/253720 | 1/2014 |
| AU | 2013/273643 | 1/2016 |

(Continued)

OTHER PUBLICATIONS

U.S. Appl. No. 18/045,572, filed Oct. 11, 2022, Liu et al.
U.S. Appl. No. 18/063,871, filed Dec. 9, 2022, Liu et al.
U.S. Appl. No. 18/175,112, filed Feb. 27, 2023, Liu et al.
U.S. Appl. No. 18/176,196, filed Feb. 28, 2023, Liu et al.
Gene Characterization Kits (1988), Strategene Catalog, 2 pages.
"N-803 Plus BCG Elicits 72% CR in BCG-Unresponsive, High-Grade Non-Muscle Invasive Bladder Cancer" Dec. 2020, Onclive. Accessed Apr. 15, 2021, 15 pages.

(Continued)

*Primary Examiner* — Michael D Pak
(74) *Attorney, Agent, or Firm* — Sheridan Ross P.C.

(57) ABSTRACT

The instant invention provides soluble fusion protein complexes and IL-15 variants that have therapeutic and diagnostic use, and methods for making the proteins. The instant invention additionally provides methods of stimulating or suppressing immune responses in a mammal using the fusion protein complexes and IL-15 variants of the invention.

17 Claims, 43 Drawing Sheets

Specification includes a Sequence Listing.

(56) References Cited

U.S. PATENT DOCUMENTS

| | | | |
|---|---|---|---|
| 10,899,821 B2 | 1/2021 | Wong et al. | |
| 11,046,747 B2 | 6/2021 | Wong et al. | |
| 11,053,299 B2 | 7/2021 | Soon-Shiong et al. | |
| 11,104,716 B2 | 8/2021 | Wong et al. | |
| 11,129,883 B2 * | 9/2021 | Marcus | A61K 39/00114 |
| 11,161,890 B2 * | 11/2021 | Wong | A61P 37/04 |
| 11,168,138 B2 | 11/2021 | Li et al. | |
| 11,173,191 B2 | 11/2021 | Liu et al. | |
| 11,318,201 B2 | 5/2022 | Wong et al. | |
| 11,365,231 B2 | 6/2022 | Wong et al. | |
| 11,369,679 B2 | 6/2022 | Wong et al. | |
| 11,471,511 B2 | 10/2022 | Liu et al. | |
| 11,498,950 B1 | 11/2022 | Wong et al. | |
| 11,571,470 B2 * | 2/2023 | Marcus | C07K 16/283 |
| 11,612,645 B2 * | 3/2023 | Marcus | C07K 14/5434 424/192.1 |
| 11,673,932 B2 * | 6/2023 | Wong | A61K 38/1774 424/85.2 |
| 11,679,144 B2 | 6/2023 | Liu et al. | |
| 2003/0045474 A1 | 3/2003 | Sailer et al. | |
| 2003/0144474 A1 | 7/2003 | Weidanz et al. | |
| 2003/0180888 A1 | 9/2003 | Fraser | |
| 2004/0156826 A1 | 8/2004 | Dangond et al. | |
| 2004/0242025 A1 | 12/2004 | Angerpointner et al. | |
| 2004/0253587 A1 | 12/2004 | Grabstein et al. | |
| 2006/0263857 A1 | 11/2006 | LeFrancois et al. | |
| 2009/0010966 A1 | 1/2009 | Davis et al. | |
| 2009/0117618 A1 | 5/2009 | Hermann et al. | |
| 2009/0238791 A1 | 9/2009 | Jacques et al. | |
| 2011/0081311 A1 | 4/2011 | Pavlakis et al. | |
| 2013/0121960 A1 | 5/2013 | Sadelain et al. | |
| 2014/0099254 A1 | 4/2014 | Chang et al. | |
| 2015/0023938 A1 | 1/2015 | Yee | |
| 2015/0152188 A1 | 6/2015 | Morisseau et al. | |
| 2015/0154743 A1 | 6/2015 | Levy et al. | |
| 2017/0088597 A1 | 3/2017 | Wong et al. | |
| 2018/0200366 A1 | 7/2018 | Wong et al. | |
| 2022/0281937 A1 | 9/2022 | Wong et al. | |

FOREIGN PATENT DOCUMENTS

| | | |
|---|---|---|
| AU | 2011/305476 | 12/2016 |
| AU | 2016/326575 | 4/2018 |
| AU | 2017/201056 | 12/2018 |
| AU | 2017/345791 | 5/2019 |
| AU | 2015/284248 | 4/2020 |
| BR | 112019007920 | 10/2019 |
| CA | 2811734 | 3/2012 |
| CA | 2953816 | 1/2016 |
| CA | 2999294 | 3/2017 |
| CA | 3041310 | 4/2018 |
| CA | 2690825 | 2/2019 |
| CN | 1441675 | 9/2003 |
| CN | 1478098 | 2/2004 |
| CN | 1493687 | 5/2004 |
| CN | 1760209 | 4/2006 |
| CN | 1780856 | 5/2006 |
| CN | 1942481 | 4/2007 |
| CN | 101360827 | 2/2009 |
| CN | 101484472 | 7/2009 |
| CN | 101743249 A | 6/2010 |
| CN | 104672325 | 6/2015 |
| CN | 105017429 | 11/2015 |
| CN | 106659775 | 5/2017 |
| CN | 101743249 B | 8/2017 |
| CN | 103370339 | 12/2017 |
| CN | 104109200 | 3/2018 |
| CN | 107880136 | 4/2018 |
| CN | 108463239 | 8/2018 |
| CN | 108948177 | 12/2018 |
| CN | 110799528 | 2/2020 |
| EP | 0971728 | 1/2000 |
| EP | 1777294 | 4/2007 |
| EP | 1934353 | 6/2008 |
| EP | 2388266 A2 | 11/2011 |
| EP | 2537933 | 12/2012 |
| EP | 2388266 B1 | 4/2014 |
| EP | 2160401 | 9/2014 |
| EP | 2619229 | 4/2016 |
| EP | 3160498 | 5/2017 |
| EP | 2769984 | 8/2017 |
| EP | 2918607 | 11/2017 |
| EP | 3305805 | 4/2018 |
| EP | 3327040 | 5/2018 |
| EP | 3352779 | 8/2018 |
| EP | 3529263 | 8/2019 |
| EP | 3673915 | 7/2020 |
| EP | 3912637 | 11/2021 |
| IN | 201917020025 | 8/2019 |
| JP | H06-87898 | 3/1994 |
| JP | H09-512165 | 12/1997 |
| JP | H11-500908 | 1/1999 |
| JP | 2001-502521 | 2/2001 |
| JP | 2008-545397 | 12/2008 |
| JP | 2009-512433 | 3/2009 |
| JP | 2010-527919 | 8/2010 |
| JP | 6251570 | 9/2011 |
| JP | 2013-541335 | 11/2013 |
| JP | 5501222 | 3/2014 |
| JP | 2014-524737 | 9/2014 |
| JP | 5841623 | 11/2015 |
| JP | 6152156 | 6/2017 |
| JP | 2017-521410 | 8/2017 |
| JP | 2018-046831 | 3/2018 |
| JP | 6408039 | 9/2018 |
| JP | 2018-174697 | 11/2018 |
| JP | 2018-532729 | 11/2018 |
| JP | 2019-033754 | 3/2019 |
| JP | 2019-533449 | 11/2019 |
| KR | 10-2007-0000252 | 1/2007 |
| KR | 10-2007-0002052 | 1/2007 |
| KR | 10-2014-0020228 | 2/2014 |
| KR | 10-2017-0047221 | 5/2017 |
| KR | 20180125435 | 11/2018 |
| KR | 2019/0091264 | 8/2019 |
| KR | 10-2070098 | 1/2020 |
| MX | 2017000116 | 5/2017 |
| MX | 2019004681 | 10/2019 |
| WO | WO 94/04689 | 3/1994 |
| WO | WO 94/29350 | 12/1994 |
| WO | WO 95/27722 | 10/1995 |
| WO | WO 96/26274 | 8/1996 |
| WO | WO 96/32478 | 10/1996 |
| WO | WO 97/34631 | 9/1997 |
| WO | WO 97/41232 | 11/1997 |
| WO | WO 98/36768 | 8/1998 |
| WO | WO 0187330 | 11/2001 |
| WO | WO 03080672 | 10/2003 |
| WO | WO 2005/046449 | 5/2005 |
| WO | WO 2005/085282 | 9/2005 |
| WO | WO 2006/063974 | 6/2006 |
| WO | WO 2007/001677 | 1/2007 |
| WO | WO 2007/046006 | 4/2007 |
| WO | WO 2008/143794 | 11/2008 |
| WO | WO 2009/002562 | 12/2008 |
| WO | WO 2009/117117 | 9/2009 |
| WO | WO 2012/040323 | 3/2012 |
| WO | WO 2012/175222 | 12/2012 |
| WO | WO 2013/076183 | 5/2013 |
| WO | WO 2014/028776 | 2/2014 |
| WO | WO 2014/066527 | 5/2014 |
| WO | WO 2015/109124 | 7/2015 |
| WO | WO 2016/004060 | 1/2016 |
| WO | WO 2017/053649 | 3/2017 |
| WO | WO 2017/205726 | 11/2017 |
| WO | WO 2018/075989 | 4/2018 |

OTHER PUBLICATIONS

Press Release, Feb. 16, 2021, ImmunityBio, Inc.: ASCO Genitourinary Cancer symposium 2021 presentation: Phase 11/111 clinical results of IL-15RaFc superagonist N-803 with BCG in BCG-

(56) References Cited

OTHER PUBLICATIONS unresponsive non-muscle invasive bladder cancer (NMIBC) carcinoma in situ (CIS) patients. Accessed Apr. 15, 2021, 5 pages.
Alam et al. (Feb. 1999) "Qualitative and Quantitative Differences in T Cell Receptor Binding of Agonist and Antagonist Ligands", Immunity, 10(2):227-237.
Alpdogan et al. (Jan. 2005) "IL-7 and IL-15: Therapeutic Cytokines for Immunodeficiency", Trends in Immunology, 25-26(1):56-64.
Anderson et al. (1995) "Functional Characterization of the Human Interleukin-15 Receptor a Chain and Close Linkage of IL 15RA and IL2RA Genes", The Journal of Biological Chemistry, 270(50):29862-29869.
Anonymous (May 15, 2014) "A Study of Intravesical BCG in Combination With ALT-803 in Patients with Non-Muscle Invasive Bladder Cancer", ClinicalTrials.gov, NTC02138734, 9 Pages.
Arcaro et al. (Nov. 19, 2001) "CD8 Endows CD8 with Efficient Coreceptor Function by Coupling T Cell Receptor/CD3 to Raft-associated CD8/p56lck Complexes", Journal of Experimental Medicine, 194(10):1485-1495.
Baeuerle et al. (Feb. 2009) "BiTE: Teaching Antibodies to Engage T-Cells for Cancer Therapy", Current Opinion in Molecular Therapeutics, 11(1):22-30.
Bailey et al. (2013) "New Interleukin-15 Superagonist (IL-15 SA) Significantly Enhances Graft-Versus-Tumor Activity After Allogeneic Hematopoietic Stem Cell Transplantation", Blood, 122(21):05 pages.
Bailey et al. (Jul. 4, 2017) "New Interleukin-15 Superagonist (IL-15SA) Significantly Enhances Graft-versus-tumor Activity", Oncotarget, 8(27):44366-44378.
Bazan et al. (Dec. 2012) "Phage display—A Powerful Technique for Immunotherapy", Human Vaccines & Immunotherapeutics, 8(12):1817-1828.
Beers et al. (1999) "The Merck Manual of Diagnosis and Therapy", 17th Edition, 986-995.
Belmont et al. (Oct. 2006) "Potent Antitumor Activity of a Tumor-specific Soluble TCR/IL-2 Fusion Protein", Journal of Clinical Immunology, 121(1):29-39.
Benton et al. (Apr. 8, 1977) "Screening λgt Recombinant Clones by Hybridization to Single Plaques in Situ", Science, 196(4286):180-182.
Bergamaschi et al. (Feb. 15, 2008) "Intracellular Interaction of Interleukin-15 with its Receptor Alpha during Production Leads to Mutual Stabilization and Increased Bioactivity", Journal of Biological Chemistry, 28(7):4189-4199.
Bernard et al. (Jun. 4, 2004) "Identification of an Interleukin-15αReceptor-binding Site on Human Interleukin-15", Journal of Biological Chemistry, 279(23):24313-24322.
Bessard et al. (Sep. 2009) "High Antitumor Activity of RLI, an Interleukin-15 (IL-15)-IL-15 Receptor a Fusion Protein, in Metastatic Melanoma and Colorectal Cancer", Molecular Cancer Therapeutics, 8(9):2736-2745.
Bevan (Aug. 1997) "In Thymic Selection, Peptide Diversity Gives and Takes Away", Immunity, 7(2): 175-178.
Bjorkman (Apr. 18, 1997) "MHC Restriction in Three Dimensions: A View of T Cell Receptor/Ligand Interactions", Cell, 89(2):167-170.
Bork, Peer, "Powers and Pitfalls in Sequence Analysis: The 70% Hurdle," Genome Research, vol. 10 (2000):398-400.
Borras et al. (Mar. 19, 2010) "Generic Approach for the Generation of Stable Humanized Single-chain Fv Fragments from Rabbit Monoclonal Antibodies", The Journal of Biological Chemistry, 285(12):9054-9066.
Bouchaud et al., "The Exon-3-Encoded Domain of IL-15Rα Contributes to IL-15 High-Affinity Binding and Is Crucial for the IL-15 Antagonistic Effect of Soluble IL-15Rα", Journal of Molecular Biology, Sep. 26, 2008, vol. 382(1), pp. 1-12.
Bruhns (Apr. 16, 2009) "Specificity and Affinity of Human Fcγ Receptors and their Polymorphic Variants for human IgG Subclasses", Blood, 113(16):3716-3725.

Busch et al. (May 1, 2002) "Stabilization of Soluble, Low-Affinity HLA-DM/HLA-DR1 Complexes by Leucine Zippers", Journal of Immunological Methods, 263(1-2):111-121.
Cany et al. (Jan. 11, 2018) "Decitabine Enhances Targeting of AML Cells by CD34+ Progenitor-Derived NK Cells in NOD/SCID/IL2Rgnull Mice", Blood, 131(2):202-214.
Capon et al. (Feb. 9, 1989) "Designing CD4 Immunoadhesins for AIDS Therapy", Nature, 337(6207):525-531.
Card et al. (Nov. 11, 2003) "A Soluble Single-Chain T-Cell Receptor IL-2 Fusion Protein Retains MHC-Restricted Peptide Specificity and IL-2 Bioactivity", Cancer Immunology, Immunotherapy, 53(4):345-357.
Chae et al. (1996) "Mutant IL-15 Protein Exerting Antagonistic Effects on IL-15 Triggered Cell Proliferation", Journal of the American Society of Nephrology, 7(9):1654.
Chamow et al. (Feb. 1996) "Immunoadhesins: Principles and Applications", Trends Biotechnology, 14:52-60.
Chan et al. (May 2010) "Therapeutic Antibodies for Autoimmunity and Inflammation", Nature Reviews Immunology, 10(5):301-316.
Cheever (Apr. 2008) "Twelve Immunotherapy Drugs That Could Cure Cancers", Immunological Reviews, 222(1):357-368.
Chirifu et al. (Jul. 22, 2007) "Crystal Structure of the IL-15-IL-15Rα Complex, a Cytokine-Receptor Unit Presented in Trans", Nature Immunology, 8:1001-1007.
Chu et al. (Mar. 2016) "Therapeutic Effects of AL T-803, an IL-15 Superagonist, in Combination with Anti-CD20 Chimeric Antigen Receptor Modified Expanded Natural Killer Cells Against Burkitt Lymphoma (BL)", Biology of Blood and Marrow Transplantation, 22(3):1 page.
Cole et al. (Feb. 19, 2008) "T Cell Receptor Engagement of Peptide-Major Histocompatibility Complex Class I Does Not Modify CD8 Binding", Molecular Immunology, 45(9):2700-2709.
Conlon et al. (Jan. 1, 2005) "Redistribution, Hyperproliferation, Activation of Natural Killer Cells and CD8 T Cells, and Cytokine Production During First-In-Human Clinical Trial of Recombinant Human Interleukin-15 in Patients With Cancer", Journal of Clinical Oncology, 33(1):74-82.
Cragg et al. (Apr. 1, 2004) "Antibody Specificity Controls in Vivo Effector Mechanisms of Anti-Cd20 Reagents", Blood, 103(7):2738-274 3.
Cuesta et al. (Apr. 2009) "In Vivo Tumor Targeting and Imaging with Engineered Trivalent Antibody Fragments Containing Collagen-Derived Sequences", Plos One, 4(4):(e5381):9 pages.
Daniels et al. (2000) "Critical Role for Cd8 in T Cell Receptor Binding and Activation by Peptide/Major Histocompatibility Complex Multimers", Journal of Experimental Medicine, 191(2):335-346.
Database Genbank (Dec. 19, 1995) "Human Interleukin-15 receptor Alpha Chain Precursor (IL 15RA) mRNA, complete eds", Genbank Accession No. U31628.1, 2 pages.
Database Genbank (May 20, 2005) "Mus Musculus Interleukin 15 Receptor, Alpha Chain, mRNA (cDNA clone Image:4457379), complete eds", Genbank Accession No. BC095982.1, 2 pages.
Database Genbank (Sep. 14, 1995) "Mus Musculus Interleukin 15 (IL15) mRNA, complete eds", Genbank Accession No. U14332.1, 2 pages.
Database Genbank (Sep. 21, 1994) "Human Interleukin 15 (IL 15) mRNA, complete eds", Genbank Accession No. U14407.1, 2 pages.
Database UniProt Sequence, retrieved from EBI, Database Accession No. 097687, XP002659759 (1999), 1 page, 1999.
Database UniProt Sequence, retrieved from EBI, Database Accession No. Q6B416, XP002659761, 1 page, 2004.
Database UniProt Sequence, retrieved from EBI, Database Accession No. Q8SPYO, XP002659760, 1 page, 2002.
Davis (1985) "Molecular Genetics of the T Cell-receptor Beta Chain", Annual Review of Immunology, 3:537-560.
Davis (1998) "Ligand Recognition by αβ T Cell Receptors", Annual Reviews Immunology, 16:523-544.
Davis et al. (Aug. 4, 1988) "T-cell Antigen Receptor Genes and T-cell Recognition", Nature, 334(6181):395-402.

(56) References Cited

OTHER PUBLICATIONS

Deer et al. (2004) "High-Level Expression of Proteins in Mammalian Cells Using Transcription Regulatory Sequences from the Chinese Hamster EF-1α Gene", Cell Culture and Tissue Engineering, 20(3):880-889.
Desbois et al. (May 23, 2016) "IL-15 Trans-Signaling with the Superagonist RLI Promotes Effector/Memory CD8+ T Cell Responses and Enhances Antitumor Activity of PD-1 Antagonists", The Journal of Immunology, 97(1):168-178.
Disis et al., "Avelumab (MSB0010718C; anti-PD-L1) in patients with recurrent/refractory ovarian cancer from the JAVELIN Solid Tumor phase lb trial: Safety and clinical activity," Journal of Clinical Oncology, 2016 ASCO Annual Meeting, vol. 34(15 supp.), 4 pages.
Doerks, Tobias et al., "Protein annotation: detective work for function prediction," TIG, vol. 14, Issue 6 (1998):248-250.
Dubois et al. (2008) "Preassociation of IL-15 with IL-15Rα-IgG1-Fc Enhances Its Activity on Proliferation of NK and CD8+/CD44high T Cells and Its Antitumor Action", Journal of Immunology, 180(4):2099-2106.
Dubois et al. (Sep. 17, 1999) "Natural Splicing of Exon 2 of Human Interleukin-15 Receptor α-Chain mRNA Results in a Shortened Form with a Distinct Pattern of Expression", The Journal of Biological Chemistry, 274(38):26978-26984.
Dudley et al. (Sep. 2003) "Adoptive-Cell-Transfer Therapy for the Treatment of Patients with Cancer", Nature Review Cancer, 3:665-695.
Eisen et al. (1996) "Antigen-Specific T-Cell Receptors and Their Reactions with Complexes Formed by Peptides with Major Histocompatibility Complex Proteins", Advances in Protein Chemistry, 49:1-56.
Ellison et al. (Jul. 10, 1982) "The Nucleotide Sequence of a Human Immunoglobulin Cγ1 gene", Nucleic Acids Research, 10(13):4071-4079.
Epardaud et al. (Apr. 15, 2008) "Interleukin-15/Interleukin-15Rα Complexes Promote Destruction of Established Tumors by Reviving Tumor-Resident CD8+ T Cells", Cancer Research, 68(8):2972-2983.
Fabbi et al. (2016) "Dual Roles of IL-15 in Cancer Biology", Journal of Cytokine Biology, 1(2):103, 7 pages.
Feldmann (May 1, 2002) "Development of Anti-TNF Therapy for Rheumatoid Arthritis", Nature Reviews Immunology 2:364-371.
Felices et al. (Dec. 2016) "CD16-IL 15-CD33 Trispecific Killer Engager (TrikE) Overcomes Cancer-Induced Immune Suppression and Induces Natural Killer Cell-Mediated Control of MDS and AML via Enhanced Killing Kinetics", Blood, 128(22):4 pages.
Felices et al. (Feb. 21, 2017) "IL-15 Super-Agonist (ALT-803) Enhances Natural Killer (NK) Cell Function Against Ovarian Cancer", Gynecologic Onocology, 145(3): 19 pages.
Ferrari-Lacraz et al. (Dec. 15, 2006) "CD8+ T Cells Resistant to Costimulatory Blockade Are Controlled by an Antagonist Interleukin-15/Fc Protein", Transplantation, 82(11):14 pages.
Ferrari-Lacraz et al. (Nov. 1, 2004) "Targeting IL-15 Receptor-Bearing Cells with an Antagonist Mutant IL-15/Fc Protein Prevents Disease Development and Progression in Murine Collagen-Induced Arthritis", The Journal of Immunology, 173(9):5818-5826.
Ferrari-Lacraz et al. (Sep. 15, 2001) "An antagonist IL-15/Fc protein prevents costimulation blockade-resistant rejection", Journal of Immunology, 167(6): 3478-3485.
Fleer (Oct. 1992) "Engineering Yeast for High Level Expression", Current Opinion in Biotechnology, 3(5):486-496.
Frankel et al. (Oct. 2000) "Cell Surface Receptor-Targeted Therapy of Acute Myeloid Leukemia: A Review", Cancer Biotherapy & Radiopharmaceuticals, 15(5) :459-47 6.
Gakamsky et al. (Sep. 2005) "CD8 Kinetically Promotes Ligand Binding to the T-Cell Antigen Receptor", Biophysical Journal, 89(3):2121-2133.
Galfre, et al., (1981) "Preparation of Monoclonal Antibodies: Strategies and Procedures", Methods in Enzymology, 73(PL B):3-46, publication nummary, 2 pages.

Garboczi et al. (Apr. 15, 1989) "HLA-A2-Peptide Complexes: Refolding and Crystallization of Molecules Expressed in *Escherichia coli* and Complexed with Single Antigenic Peptides", PNAS, 89(8):3429-3433.
Garboczi et al. (Nov. 14, 1996) "Pillars Article: Structure of the Complex Between Human T-cell Receptor, Viral Peptide and HLA-A2", Nature, 384:134-141.
Gerber et al. (2009) "Antibody Drug-Conjugates Targeting the Tumor Vasculature- Current and Future Developments", mAbs, 1 (3) :24 7-253.
Gillies et al. (May 15, 2005) "An Anti-CD20-IL-2 Immunocytokine is Highly Efficacious in A SCIO Mouse Model of Established Human B Lymphoma", Blood, 105(10):3972-3978.
Golay et al. (Nov. 14, 2013) "Glycoengineered CD20 Antibody Obinutuzumab Activates Neutrophils and Mediates Phagocytosis Through CD16B More Efficiently Than Rituximab", Blood, 122(20):3482-3491.
Gomes et al. (May 5, 2013) "IL-15 Analogue (ALT-803) Targeting T Regulatory Cells Causes Tomor Burden Reduction in an Orthotopic Non-Muscle Invasive Bladder Cancer Model," The Journal of Urology, 189(4S):e238-e239.
Gomes-Giacoia et al. (Jun. 4, 2014) "Intravesical ALT-803 and BCG Treatment Reduces Tumor Burden in a Carcinogen Induced Bladder Cancer Rat Model; a Role for Cytokine Production and NK Cell Expansion", PLoS One, e96705, 9(6):11 pages.
Graham et al. (Jul. 1977) "Characteristics of a Human Cell Line Transformed by DNA from Human Adenovirus Type 5", Journal of General Virology, 36(1):59-72.
Grunstein et al. (Oct. 1975) "Colony Hybridization: A Method for the Isolation of Cloned DNAs That Contain a Specific Gene", Proceedings of the National Academy of Sciences of the United States of America, 72(10):3961-3965.
Guglielmi et al. (Jul. 15, 2002) "Donor lymphocyte infusion for relapsed chronic myelogenous euken1 ia: prognostic relevance of the initial cell dose", Blood, 100(2):295-307.
Guo et al. (2013) "Therapeutic Cancer Vaccines: Past, Present and Future", Advances in Cancer Research, 119:421-475.
Han et al., "IL-15:IL-15 receptor alpha superagonist complex: High-level co-expression in recombinant mammalian cells, purification and characterization", Cytokine, Sep. 28, 2011, vol. 56(3), pp. 804-810.
Hara et al. (Nov. 1, 1995) "Implicating a Role for Immune Recognition of Self in Tumor Rejection: Passive Immunization Against the Brown Locus Protein", Journal of Experimental Medicine, 182(5):1609-1614.
Hatzimichael et al. (2010) "Hematopoietic stem cell transplantation", Stem Cells and Cloning: Advances and Applications, 3:105-117.
Hayden-Ledbetter et al. (Apr. 2009) "CD20-Directed Small Modular Immunopharmaceutical, TRU-015, Depletes Normal and Malignant B Cells", Clinical Cancer Research, 15(8):2739-2746.
Hessell et al. (Sep. 6, 2007) "Fc Receptor but Not Complement Binding is Important in Antibody Protection Against HIV", Nature, 449(7158):101-104.
Hezareh et al. (Dec. 2001) "Effector Function Activities of a Panel of Mutants of a Broadly Neutralizing Antibody against Human Immunodeficiency Virus Type 1", Journal of Virology, 75(24):12161-12168.
Hogquist et al. (Jan. 1994) "T Cell Receptor Antagonist Peptides Induce Positive Selection", Cell, 76(1): 17-27.
Holliger et al. (Sep. 2005) "Engineered Antibody Fragments and the Rise of Single Domains", Nature Biotechnology, 23(9):1126-1136.
Huang, J., et al. Intravesical ALT-803 for BCG-unresponsive Bladder Cancer—A Case Report. Urology Case Reports 14 (2017) 15-17.
Hughes et al. (Apr. 2005) "Transfer of a TOR Gene Derived from a Patient with a marked Antitumor Response Conveys Highly Active T-Cell Effector Functions", Human Gene Therapy, 16(4):457-472.
Jakobisiak et al., Interleukin 15 as a promising candidate for tumor immunotherapy. Cytokine & Growth Factor Reviews. 2011; 22:99-108.

(56) References Cited

OTHER PUBLICATIONS

Kaspar et al. (May 15, 2007) "The antibody-mediated targeted delivery of interleukin-15 and GM-CSF to the tumor neovasculature inhibits tumor growth and metastasis Cancer Research", American Association for Cancer Research, US 67(10): 4940-4948.
Kern et al. (Sep. 17, 1999) "Expression, Purification, and Functional Analysis of Murine Ectodomain Fragments of CD8αα and CD8αβ Dimers", The Journal of Biological Chemistry, 274:27237-27243.
Khantasup et al. (Dec. 1, 2015) "Design and Generation of Humanized Single-chain Fv Derived from Mouse Hybridoma for Potential Targeting Application", Monoclonal Antibodies in Immunodiagnosis and Immunotherapy, 34(6):404-417.
Kim et al. (2012) "Humanization by CDR Grafting and Specificity-Determining Residue Grafting" Methods in molecular biology, 907:237-245.
Kim et al. (Feb. 18, 2016) "IL-15 superagonist/IL-15RαSushi-Fc fusion complex (IL-15SA / IL-15RαSu-Fc; ALT-803) markedly enhances specific subpopulations of NK and memory CD8+ T cells, and mediates potent anti-tumor activity against murine breast and colon carcinomas", Oncotarget, 7(13):16130-16145.
Kim, Yon Su et al., "Targeting the IL-15 Receptor with an Antagonist IL-15 Mutant/Fcγ 2a Protein Blocks Delayed-Type Hypersensitivity," The Journal of Immunology, vol. 160(1998):5742-5748.
Kimmel (1987) "Identification and Characterization of Specific Clones: Strategy for Confirming the Validity of Presumptive Clones", Methods in Enzymology, 152:507-511.
Klebanoff et al. (Feb. 17, 2004) "IL-15 Enhances the in Vivo Antitumor Activity of Tumor-Reactive CD8+ T Cells", Proceedings of the National Academy of Sciences of the United States of America, 101(7):1969-1974.
Kobayashi et al. (Dec. 15, 1994) "Tyrosinase Related Protein 1 (TRP1) Functions as a DHICA Oxidase in Melanin Biosynthesis", The EMBO Journal, 13(24):5818-5825.
Kostelny et al. (Mar. 1, 1992) "Formation of a Bispecific Antibody by the Use of Leucine Zippers", Journal of Immunology, 148(5):1547-1553.
Kouzarides et al. (Aug. 17, 1989) "Leucine zippers of fos, jun and GCN4 dictate dimerization specificity and hereby control DNA binding", Nature, 340:568-571.
Kouzarides et al. (Dec. 15, 1988) "The role of the leucine zipper in the fos-jun Interaction", Nature, 336:646-651.
Kruif et al. (Mar. 29, 1996) "Leucine Zipper Dimerized Bivalent and Bispecific scFv Antibodies from a Semi-synthetic Antibody Phage Display Library", The Journal of Biological Chemistry, 271:7630-7634.
Kubetzko et al. (Nov. 17, 2006) "PEGylation and Multimerization of the Anti-p185HER-2 Single Chain Fv Fragment 4D5-Effects on Tumor Targeting", The Journal of Biological Chemistry, 281:35186-35201.
Laugel et al. (Aug. 17, 2007) "Different T Cell Receptor Affinity Thresholds and CD8 Coreceptor Dependence 43 Govern Cytotoxic T Lymphocyte Activation and Tetramer Binding Properties", The Journal of Biological Chemistry, 282:23799-23810.
Lawrencia et al. (May 2001) "Transfection of Urothelial Cells using Methyl-β-Cyclodextrin Solubilized Cholesterol and Dotap", Gene Therapy, 8(10):760-768.
Lazar et al. (Mar. 14, 2006) "Engineered Antibody Fc Variants with Enhanced Effector Function", Proceedings of the National Academy of Sciences, 103(11):4005-4010.
Lazar et al. (Mar. 1988) "Transforming Growth Factor α: Mutation of Aspartic Acid 47 and Leucine 48 Results in Different Biological Activities", Molecular and Cellular Biology, 8(3):1247-1252.
Lin et al. (Aug. 10, 1990) "Expression of T Cell Antigen Receptor Heterodimers in a Lipid-Linked Form", Science, 249(4969):677-679.
Liu et al. "A Novel Fusion of ALT-803 (Interleukin (IL)-15 Superagonist) with an Antibody Demonstrates Antigen-specific Antitumor Responses," Journal of Biological Chemistry, 2016, vol. 291(46), pp. 23869-23881. Online publication Sep. 20, 2016.
Liu et al. (Dec. 2014) "Evaluation of a Novel CD20-Targeted IL-15 Immunotherapeutic with Potent Activity Against B Cell Lymphoma", Journal for ImmunoTherapy of Cancer, 2(Suppl 3):1 page.
Lu et al. (2009) "Construction and Production of an IgG-like Tetravalent Bispecific Antibody for Enhanced Therapeutic Efficacy", Methods in Molecular Biology, 525:377-404.
Mathios et al. (Jan. 1, 2016) "Therapeutic Administration of IL-15 Superagonist Complex ALT-803 Leads to Long-term Survival and Durable LAntitumor Immune Response in a Murine Glioblastoma Model", International Journal of Cancer, 138(1):187-194.
Matsumoto et al., Intravesical Interleukin-15 Gene Therapy in an Orthotopic Bladder Cancer Model. Human Gene Therapy. Nov. 2011; 22:1423-1432.
McLaughlin et al. (2015) "Adoptive T-cell therapies for refractory/relapsed leukemia and lymphoma: current strategies and recent advances", Therapy Advance Hematology, 6(6):295-307.
Mohler et al. (Aug. 1, 1993) "Soluble Tumor Necrosis Factor (TNF) Receptors Are Effective Therapeutic Agents in 3 Lethal Endotoxemia and Function Simultaneously as Both TNF Carriers and TNF Antagonists", The Journal of Immunology, 151(3):1548-1561.
Mortier et al. (Jan. 20, 2006) "Soluble Interleukin-15 Receptor α (IL-15Rα)-sushi as a Selective and Potent Agonist of IL-15 Action through IL-15Rβ/γ", The Journal of Biological Chemistry, 281(3):1612-1619.
Morton et al. (Nov. 1, 2016) "Humanized Mouse Xenograft Models: Narrowing the Tumor-Microenvironment Gap", Cancer Research, 76(21):6153-6158.
Moskaug et al. (Sep. 15, 1989) "Translocation of Diphtheria Toxin A-Fragment to the Cytosol. Role of the Site of Interfragment Cleavage", Journal of Biological Chemistry, 264(26):15709-15713.
Mosquera et al. (Apr. 1, 2005) "In Vitro And In Vivo Characterization of a Novel Antibody-Like Single-Chain TCR Human IgG1 Fusion Protein", Journal of Immunology, 174(7):4381-4388.
Neveu et al. (Jul. 2006) "Impact of CD8-MHC Class I Interaction in Detection and Sorting Efficiencies of Antigen-7 Specific T Cells Using MHC Class I/peptide Multimers: Contribution of pMHC Valency", International Immunology, 18(7):1139-1145.
Ng et al. (2005) "Liposomal Polyene Antibiotics", Methods in Enzymology, 391:304-313.
Nogawa et al. (Apr. 2005) "Intravesical Administration of Small Interfering RNA Targeting PLK-1 Successfully Prevents the Growth of Bladder Cancer", Journal of Clinical Investigation, 115(4):978-985.
Novellino et al. (Mar. 2005) "A Listing of Human Tumor Antigens Recognized by T Cells: Mar. 2004 Update", Cancer Immunology, Immunotherapy, 54(3):187-207.
Nugent et al. (May 15, 2005) "Low Binding Capacity of Murine Tetramers Mutated at Residue 227 Does Not Preclude the Ability to Efficiently Activate CD8+ T Lymphocytes", Immunology Letters, 98(2):208-215.
Oleksiewicz et al. (Oct. 15, 2012) "Anti-bacterial Monoclonal Antibodies: Back to the Future?", Archives of Biochemistry and Biophysics, 526(2):124-131.
Olsnes et al. (1982) "Chimeric Toxins", Pharmacology and Therapeutics, 15(3):355-381.
Orti et al. (2017) "Donor lymphocyte infusions in AML and MOS: Enhancing the graft-versus-leuke1nia effect", Experimental Hematology, 48:1-11.
Ortiz-Sanchez et al. (May 2008) "Antibody-cytokine Fusion Proteins: Applications in Cancer Therapy", Expert Opinion on Biological Therapy, 8(5):609-632.
Otegbeye et al. (Dec. 3, 2015) "The IL-15 Super-Agonist ALT-803 Promotes Superior Activation and Cytotoxicity of Ex Vivo Expanded NK Cells Against AML", Blood, 3090, 126(23):4 Pages.
Ozdemir et al. "Mechanisms of Superior Anti-Tumor Cytotoxic Response of Interleukin 15-Induced Lymphokine-Activated Killer Cells," Journal of Immunotherapy, Jan./Feb. 2005, vol. 28(1), pp. 44-52.
Pardoll (Apr. 2012) "The Blockade of Immune Checkpoints in Cancer Immunotherapy", Nature Reviews Cancer, 12(4):252-264.
Parmiani et al. (Feb. 15, 2007) "Unique Human Tumor Antigens: Immunobiology and Use in Clinical Trials", The Journal of Immunology, 178(4):1975-1979.

(56) References Cited

OTHER PUBLICATIONS

Pastan et al. (1992) "Recombinant Toxins as Novel Therapeutic Agents", Annual Review Biochemistry, 61:331-354.
Pastan et al. (Dec. 5, 1986) "Immunotoxins", Cell, 47:641-648.
Penichet et al. (1997) "Antibody-IL-2 Fusion Proteins: A Novel Strategy for Immune Protection", Human Antibodies, 8(3):106-118.
Pettit et al. (Jan. 24, 1997) "Structure-Function Studies of Interleukin 15 Using Site-Specific Mutagenesis, Polyethylene Glycol Conjugation, and Homology Modeling", Journal of Biological Chemistry, 272(4):2312-2318.
Powles et al., "MPDL3280A (anti-PD-L1) treatment leads to clinical activity in metastatic bladder cancer," Nature, Letter, Nov. 27, 2014, vol. 515(7528), 12 pages.
Quemener, Agnes et al., "Docking of Human Interleukin-15 to its Specific Receptor alpha Chain: Correlation Between Molecular Modeling and Mutagenesis Experimental Data," Proteins: Structure, Function and Bioinformatics, vol. 65 (2006):623-636.
Rabinowitz et al. (Feb. 20, 1996) "Kinetic Discrimination in T-cell Activation", Proceedings of the National Academy of Sciences of the United States of America, 93(4):1401-1405.
Ramos et al. (Apr. 10, 2015) "Current Approaches in the Treatment of Relapsed and Refractory Acute Myeloid Leukemia", Journal of Clinical Medicine, 4:665-695.
Richards et al. (Aug. 2008) "Optimization of Antibody Binding to FcγRIIa Enhances Macrophage Phagocytosis of Tumor Cells", Molecular Cancer Therapeutics, 7(8):2517-2527.
Rieker et al. (2000) "Molecular Applications of Fusions to Leucine Zippers", Methods in Enzymology, 328:282-296.
Rossi et al. (Oct. 29, 2009) "CD20-Targeted Tetrameric Interferon-α, a Novel and Potent Immunocytokine for the Therapy of B-Cell Lymphomas", Blood, 114(18):3864-3871.
Rossi et al., "Optimization of Multivalent Bispecific Antibodies and Immunocytokines with Improved in Vivo Properties," Bioconjugate Chemistry. 2013, vol. 24, pp. 63-71.
Roychowdhury et al. (Nov. 1, 2004) "Failed 1-15 Adoptive Immunotherapy with Tumor-Specific T Cells: Reversal with Low-Dose Interleukin 15 but not Low-Dose Interleukin 2", Cancer Research, 64(21):8062-8067.
Rubinstein et al. (Jun. 13, 2006) "Converting IL-15 to a Superagonist by Binding to Soluble IL-15Rα", Proceedings of the National Academy of Sciences of the United States of America, 103(24):9166-9171.
Rudikoff et al., "Single amino acid substitution altering antigen-binding specificity," PNAS, Mar. 1982, vol. 79, pp. 1979-1983.
Sauter et al. (Apr. 29, 2013) "Interleukin-15 Administration Increases Graft-Versus-Tumor Activity in Recipients of Haploidentical Hematopoietic SCT", Bone Marrow Transplantation, 48(9):1237-1242.
Savio, Alicia Santos, "IL-15: a relevant cytokine for lymphoid homeostasis and autoimmune diseases," Biotecnologia Aplicada, vol. 23 (2006):87-93.
Schmohl et al. (Jul. 2016) "Enhanced ADCC and NK Cell Activation of an Anticarcinoma Bispecific Antibody by Genetic Insertion of a Modified IL-15 Cross-linker", TriKE Facilitates ADCC and Sustaining of NK Cells, Molecular Therapy, 24(7):1312-1322.
Schott et al. (Dec. 2002) "Mouse MHC Class I Tetramers That Are Unable to Bind to CD8 Reveal the Need for CD8 Engagement in Order to Activate Naive CD8 T Cells", European Journal of Immunology, 32(12):3425-3434.
Shen et al. (Feb. 15, 2006) "Single Variable Domain-IgG Fusion a Novel Recombinant Approach to Fe Domain-Containing Bispecific Antibodies", The Journal of Biological Chemistry, 281:10706-10714.
Skolnick, Jeffrey et al., "From genes to protein structure and function: novel applications of computational approaches in the genomic era," Trends Biotechnol., vol. 18 Issue 1 (2000):34-39.
Isliwkowski et al. (Sep. 13, 2013) "Antibody Therapeutics in Cancer", Science, 341(6151):1192-1198.
Sloan et al. (Jun. 29, 1995) "Mediation by HLA-DM of Dissociation of Peptides from HLA-DR" Nature, 375:802-806.
Sockolosky et al. (Apr. 18, 2016) "Durable Antitumor Responses to CD47 Blockade Require Adaptive Immune Stimulation", Proceedings of the National Academy of Sciences of the United States of America, May 10, 2016, 113(19): E2646-E2654.
Sprent et al. (Mar. 29, 2000) "T-cell proliferation in vivo and the role of cytokines", Philosophical Transactions of the Royal Society of London, Series B, Biological Sciences, 355(1395):317-322.
Steel, Interleukin-15 and its Receptor Augment Dendritic Cell Vaccination Against the neu Oncogene Through the Induction of Antibodies Partially Independent of CD4-help. Cancer Res. Feb. 1, 2010; 70(3): 1-19.
Stern et al. (Feb. 7, 1992) "The Human Class II MHC Protein HLA-DR1 Assembles as Empty αβ Heterodimers in the Absence of Antigenic Peptide," Cell, 68(3):465-477.
Stewart et al. (Sep. 2015; e-published on May 5, 2015) "Identification and Characterization of MEDI4736, an Antagonistic Anti-PD-L 1 Monoclonal Antibody", Cancer Immunolgy Research, 3(9):1052-1062.
Stoklasek et al. (Nov. 4, 2015) "Combined IL-15/IL-15Rα Immunotherapy Maximizes IL-15 Activity in Vivo", Journal of Immunology, 177(9):6072-6080.
Sukumar (Nov. 4, 2015) "Modulating Immunometabolism of Tumor Specific Mouse and Human Lymphocytes to Enhance T Cell Based Therapy for Cancer", Journal for ImmnoTherapy of Cancer, 02, 2(Suppl 3): 2 pages.
Tai et al. (Sep. 15, 2010) "The Role of HER2 in Cancer Therapy and Targeted Drug Delivery", Journal of Controlled Releease, 146(3):264-275.
Tamura et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, Feb. 2000, vol. 164, pp. 1432-1441.
Tay et al., (Jul. 26, 2016) "TriKEs and BiKEs Join CARs on the Cancer Immunotherapy Highway", Human Vaccines & Immunotherapeutics, 12(11):2790-2796.
Terawaki et al. (Jul. 2007) "Specific and High-affinity Binding of Tetramerized PD-L 1 Extracellular Domain to PD-1-expressing Cells: Possible Application to Enhance T Cell Function", International Immunology, 19(7):881-890.
Thaventhiran et al. (2012) "T Cell Co-Inhibitory Receptors: Functions and Signalling Mechanisms", Journal of Clinical & Cellular Immunology, S12:12 pages.
Theobald et al. (Dec. 19, 1995) "Targeting P53 as a General Tumor Antigen", PNAS, 92(26)11993-11997.
Thomson et al. (Aug. 1985) "Pigmentation-associated Glycoprotein of Human Melanomas and Melanocytes: Definition With a Mouse Monoclonal Antibody", Journal of Investigative Dermatology, 85(2):169-174.
Tietze et al. (Mar. 29, 2012) "Delineation of Antigen-Specific and Antigen-Nonspecific CD8+ Memory T-Cell Responses after Cytokine-Based Cancer Immunotherapy", Blood, 119(13):3073-3083.
Tokuriki et al., "Stability effects of mutations and protein evolvability," Current Opinion in Structural Biology, 2009, vol. 19, pp. 596-604.
Tomalia (1993) "StarburstCascade Dendrimers: Fundamental Building Blocks for a New Nanoscopic Chemistry Set", Aldrichimica Acta, 25(4):89-101.
Tonegawa (Apr. 14, 1983) "Somatic Generation of Immune Diversity", Bioscience Reports, 8(1):3-26.
Tough et al. (May 15, 2001) "An IFN-γ-Dependent Pathway Controls Stimulation of Memory Phenotype CD8+ T Cell Turnover in Vivo by IL-12, IL-18, and IFN-γ", Journal of Immunology, 166(10):6007-6011.
Traunecker et al. (Jan. 1989) "Solubilizing the T-Cell Receptor-Problems in Solution", Immunology Today, 10(1):29-32.
Trevisani et al. (Jun. 1992) "Ethanol Elicits and Potentiates Nociceptor Responses via the Vanilloid Receptor-1", Nature Neuroscience, 5(8):546-551.
Trevesani et al. (Jun. 2004) "Ethanol Causes Inflammation in the Airways by a Neurogenic and TRPV1-Dependent Mechanism", Journal of Pharmacalogy and Experimental Therapeutics, 309(3): 1167-1173.

(56) References Cited

OTHER PUBLICATIONS

Tyagi et al. (Jan. 2004) "Urodynamic and Immunohistochemical Evaluation of Intravesical Capsaicin Delivery using Thermosensitive Hydrogel and Liposomes", The Journal of Urology, 171 (1):483-489.
Urlaub et al. (Jul. 1980) "Isolation of Chinese Hamster Cell Mutants Deficient in Dihydrofolate Reductase Activity", PNAS, 77(7):4216-4220.
Valencia et al. (Mar. 15, 2013) "In Vitro Selection of Proteins with Desired Characteristics Using mRNA-display", Methods, 60(1):32 pages.
Valitutti (May 11, 1995) "Serial Triggering of Many T-Cell Receptors by a Few Peptide-MHC Complexes", Nature, 375(6527):148-151.
Van Den Bergh et al. (2015) "Interleukin-15: New Kid on the Block for Antitumor Combination Therapy", Cytokine and Growth Factor Reviews, 26:15-24.
Verbist et al. Functions of IL-15 in Anti-Viral Immunity: Multiplicity and Variety. Cytokin. Sep. 2012; 59(3):467-478.
Villinger et al. (Sep. 3, 3004) "IL-15 is Superior to IL-2 in the Generation of Long-Lived Antigen Specific Memory CD4 and CD8 T Cells in Rhesus Macaques", Vaccine, 22(25-26):3510-3521.
Vincent et al. (Aug. 1, 2013) "Tumor Targeting of the IL-15 Superagonist RU by an anti-GD2 Antibody Strongly Enhances Its Antitumor Potency", International Journal of Cancer, 133(3):757-765.
Vincent et al. (Nov. 2013) "Antitumor Activity of an Immunocytokine Composed of an Anti-GD2 Antibody and the IL-15 Superagonist RLI", OncoImmunology, e26441, 2(11):3 pages.
Vincent et al. (Oct. 2011) "Development of Two IL 15 Immunocytokines Targeting Either GD2- or CD20-tumoral Bearing Cells", Cytokine, 56(1):1 page.
Wahl et al. (1987) "Molecular Hybridization of Immobolized Nucleic Acids: Theoretical Concepts and Practical Considerations", Methods in Enzymology, 152:399-407.
Waldmann et al., IL-15 Receptor, 2000, pp. 1521-1528.
Waldmann, Thomas A., "The biology of interleukin-2 and interleukin-15: implications for cancer therapy and vaccine design," Nature Reviews Immunology, vol. 6 Issue 8 (2006):595-601.
Wang et al. (Aug. 15, 2009) "Structural Basis of the CD8αβ/MHC Class I Interaction: Focused Recognition Orients CD8β to a T Cell Proximal Position", The Journal of Immunology, 183(4):2554-2564.
Ward et al. (Nov. 2009) "*E. coli* Expression and Purification of Human and Cynomolgus IL-15", Protein Expression and Purification, 68(1):42-48.
Wei et al. (2001) "The Sushi Domain of Soluble IL-15 Receptor a Is Essential for Binding IL-15 and Inhibiting Inflammatory and Allogenic Responses In Vitro and In Vivo", The Journal of Immunology, 167:277-282.
Weidanz et al. (Dec. 1, 1996) "Display of Functional αβ Single-Chain T-Cell Receptor Molecules on the Surface of Bacteriophage", Journal of Immunological Methods, 221 (1-2):59-76.
Weidle et al. (2013) "The Emerging Role of New Protein Scaffold-based Agents for Treatment of Cancer", Cancer Genomics and Proteomics, 10(4):155-168.
Weiner (Sep. 2007) "Building Better Magic Bullets—Improving Unconjugated Monoclonal Antibody Therapy for Cancer", Nature Reviews Cancer, 7:701-706.
Wells (Sep. 18, 1990) "Additivity of Mutational Effects in Proteins", Biochemistry, 29(37):8509-8517.
Wen et al. (2008) "Targeting Activity of a TCR/IL-2 Fusion Protein Against Established Tumors", Cancer Immunology Immunother, 57(12):1781-1794.
Whitlow et al. (Apr. 1991) "Single-Chain Fv Proteins and their Fusion Proteins", Methods: A Companion to Methods in Enzymology, 2(2):97-105.
Wong et al. (2011) "Interleukin-15: Interleukin-15 Receptor α Scaffold for Creation of Multivalent Targeted Immune Molecules", Protein Engineering, Design & Selection, 24(4):373-383.

Wong et al. (May 1, 2012) "Efficacy and mechanism-of-action of a novel superagonist IL-15:IL-15Rα/Fc fusion complex in murine multiple myeloma syngeneic mouse models (46.44)", The Journal of Immunology, 188(Suppl 1):04 pages.
Wong et al. (Nov. 1, 2013) "The IL-15-based superagonist ALT-803 promotes the antigen-independent conversion of memory CD8+ T cells into innate-like effector cells with antitumor activity", Oncoimmunology, 2(11): e26442-3 pages.
Wooldridge et al. (Jul. 29, 2005) "Interaction between the CD8 Coreceptor and Major Histocompatibility Complex Class I Stabilizes T Cell Receptor-Antigen Complexes at the Cell Surface", The Journal of Biological Chemistry, 280:27491-27501.
Wu, IL-15 Agonists: The Cancer Cure Cytokine. J Mol Genet Med. Feb. 28, 2014; 7(85):1-6.
Xiao et al. "Antitumor Efficacy of Intravesical BCG, Gemcitabine, Interferon-α and Interleukin-2 as Mono- or Combination-Therapy for Bladder Cancer in an Orthotopic Tumor Model," Clinical Medicine Insights: Oncology, 2011, vol. 5, pp. 315-323.
Xiong et al., "Efficient inhibition of human B-cell lymphoma xenografts with an anti-CD20 + anti-CD3 bispecific diabody," Cancer Letters, 2002, vol. 177, pp. 29-39.
Xu et al. (May 15, 2013) "Efficacy and Mechanism-of-Action of a Novel Superagonist Interleukin-15: Interieukin-15 Receptor αSu/Fc Fusion Complex in Syngeneic Murine Models of Multiple Myeloma", Therapeutics, Targets and Chemical Biology, 73(10):3075-3085.
Xuan et al. (Apr. 8, 2010) "Targeted Delivery of Interferon-Alpha via Fusion to Anti-CD20 Results in Potent Antitumor Activity against B-Cell Lymphoma", Blood, 115(14):2864-2871.
Yang et al. (Nov.-Dec. 2008) "Clinical-Scale Lentiviral Vector Transduction of PBL for TCR Gene Therapy and Potential for Expression in Less Differentiated Cells", Journal of Immunotherapy, 31 (9):830-839.
Yu et al. (Apr. 17, 2012) "Simultaneous Inhibition of Two Regulatory T-Cell Subsets Enhanced Interleukin-15 Efficacy in a Prostate Tumor Model", Proceedings of the National Academy of Sciences of the United States of America, 109(16):6187-6192.
Yu et al. (Dec. 15, 2010), e-Published (Oct. 5, 2010) "Simultaneous Blockade of Multiple Immune System Inhibitory Checkpoints Enhances Antitumor Activity Mediated by Interleukin-15 in a Murine Metasttc Colon Croinoma Model", Clinical Cancer Research, 16(24):1-16 pages.
Yu et al., "Antitumor Effects of Recombinant BCG and Interleukin-12 DNA Vaccines on Xenografted Murine Bladder Cancer," Urology, Mar. 2004, vol. 63(3), pp. 596-601.
Zah et al. (Jun. 2016) "T Cells Expressing CD19/CD20 Bispecific Chimeric Antigen Receptors Prevent Antigen Escape by Malignant B Cells", Cancer Immunology Research, 4(6):498-508.
Zhang et al. (May 1998) "Potent and Selective Stimulation of Memory-Phenotype CD8+ T Cells in Vivo by IL-15", Immunity, 8(5):591-599.
Zhang et al. (May 5, 2009) "Interleukin-15 Combined with an Anti-CD40 Antibody Provides Enhanced Therapeutic Efficacy for Murine Models of Colon Cancer", Proceedings of the National Academy of Sciences of the United States of America, 106(18):7513-7518.
Zhao et al. (Nov. 1, 2007) "High-Affinity TCRs Generated by Phage Display Provide CD4+ T Cells with the Ability to Recognize and Kill Tumor Cell Lines", The Journal of Immunology, 179(9):5845-5854.
Zheng et al. (Jan. 15, 2006) "An Antagonist Mutant IL-15/Fc Promotes Transplant Tolerance", Transplantation, 81(1):109-116.
Zhu et al. (Mar. 1, 2006) "Visualization of p53264-272/HLA-A*0201 Complexes Naturally Presented on Tumor Cell Surface by a Multimeric Soluble Single-Chain T Cell Receptor", Journal of Immunology, 176(5):3223-3232.
Zhu et al. (Sep. 15, 2009) "Novel Human Interleukin-15 Agonists", Journal of Immunology, 183(6):3598-3607.
International Search Report and Written Opinion for PCT International Application No. PCT/US2008/005918, mailed on Sep. 4, 2008, 6 pages.
International Preliminary Report on Patentability for International (PCT) Patent Application No. PCT/US2008/005918, dated Nov. 17, 2009 5 pages.

(56) References Cited

OTHER PUBLICATIONS

Supplementary European Search Report for Application No. PCT/US2008/005918, dated Feb. 4, 2011, 8 pages.
Official Action (with English translation) for Chinese Patent Application No. 201810135797.6, dated Mar. 1, 2021 13 pages.
Official Action (with English translation) for Chinese Patent Application No. 201810136797.6, dated Nov. 10, 2021 6 pages.
Extended European Search Report dated Feb. 4, 2011 issued for Application No. 08743432.0.
Partial European Search Report for Application No. 11178091.2, dated Sep. 22, 2011, 5 pages.
European Search Report issued Sep. 22, 2011 and mailed on Oct. 12, 2011, for European Patent Application No. 11178091.2.
European Search Report for Application No. 11178091.2, dated Nov. 30, 2011, 10 pages.
Official Action for U.S. Appl. No. 16/654,958, dated May 28, 2021 16 pages.
Final Action for U.S. Appl. No. 16/654,958, dated Oct. 27, 2021 9 pages.
Notice of Allowance for U.S. Appl. No. 16/654,958, dated Dec. 9, 2021 7 pages.
Notice of Allowance for U.S. Appl. No. 16/654,958, dated May 11, 2022 7 pages.
Official Action for U.S. Appl. No. 17/716,986, dated Oct. 27, 2022 20 pages.
Notice of Allowance for U.S. Appl. No. 17/716,986, dated Mar. 15, 2023 11 pages.
Official Action for U.S. Appl. No. 16/659,311, dated May 11, 2021 13 pages.
Notice of Allowance for U.S. Appl. No. 16/659,311, dated Sep. 21, 2022 9 pages.
Final Action for U.S. Appl. No. 16/659,311, dated Nov. 9, 2021 16 pages.
Official Action for U.S. Appl. No. 16/659,311, dated May 24, 2022 14 pages.
"History of Changes for Study: NCT02138734, a Study of Intravesical Bacillus Calmette-Guerin (BCG) in Combination With ALT-803 in Patients With BCG-naïve Non-Muscle Invasive Bladder Cancer" Clinical Trials, (first posted on May 15, 2014), 9 pages.
Alaoui-Ismaili et al., "Design of second generation therapeutic recombinant bone morphogenetic proteins," Cytokine Growth Factor Reviews, 2009, vol. 20(5-6), pp. 501-507).
Bernier et al., "Pharmacological chaperone action on G-protein-coupled receptors," Current Opinion in Pharmacology, 2004, vol. 4, pp. 528-533.
Bhattacharya et al., "Impact of genetic variation on three dimensional structure and function of proteins," PLoS ONE, 2017, vol. 12(3), pp. e0171355, 22 pages.
Burkett et al., "IL-15Rα expression on CD8+ T cells is dispensable for T cell memory," Proceedings of the National Academy of Sciences (PNAS), Apr. 15, 2003, vol. 100(8), pp. 4724-4729.
Guo et al., "Protein tolerance to random amino acid change," PNAS USA, 2004, vol. 101(25), pp. 9205-9210.
Guo et al., "Immunobiology of the IL-15-IL-15Rα Complex as an Antitumor and Antiviral Agent," Cytokine Growth Factor Rev., Dec. 2017, vol. 38, pp. 10-21, 31 pages.
Ulloa-Aguirre et al., "Pharmacologic Rescue of Conformationally-Defective Proteins: Implications for the Treatment of Human Disease," Traffic, 2004, vol. 5, pp. 821-837.
Wolchok et al., "Nivolumab plus Ipilimumab in Advanced Melanoma," New England Journal of Medicine, Jun. 2, 2013, vol. 369(2), pp. 122-133.
Official Action (with English translation) for Chinese Patent Application No. 201810135797.6, dated Mar. 7, 2022 4 pages.
Byers, "What Can Randomized Controlled Trials Tell Us About Nutrition and Cancer Prevention?," CA Journal, vol. 49(6), Nov./Dec. 1999.
Granziero et al., "Adoptive immunotherapy prevents prostate cancer in a transgenic animal model," European Journal of Immunology, 1999, vol. 29, pp. 1127-1138.
Weers et al., "Daratumumab, a Novel Therapeutic Human CD38 Monoclonal Antibody, Induces Killing of Multiple Myeloma and Other Hematological Tumors," The Journal of Immunology, 2011, vol. 186(3), pp. 1840-1848.
Giron-Michel et al., "Membrane-bound and soluble IL-15IL-15Ra complexes display differential signaling and functions on human hematopoietic progenitors," Blood, Oct. 1, 2005; pre-published online in Jun. 2005, vol. 106(7), pp. 2302-2310.
Merck Company Statement, "Merck Announces Generic Name for MK-3475, Merck's Investigational anti-PD-1 Antibody: Pembrolizumab," retrieved Feb. 28, 2024 online from www.merck.com/news/merck-announces-generic-name-for-mk-3475-mercks-investigational-anti-pd-1-antibody-penbrolizumab/, May 30, 2014, 2 pages.
Mishra et al., Molecular Pathways: Interleukin-15 Signaling in Health and in Cancer, Clinical Cancer Research, Apr. 15, 2014, vol. 20(8), pp. 2044-2050.
Reck et al., "Pembrolizumab versus Chemotherapy for PD-L1-Positive Non-Small-Cell Lung Cancer," The New England Journal of Medicine, Nov. 10, 2016, vol. 375(19), pp. 1823-1833.
Shitara et al., "Efficacy and Safety of Pembrolizumab or Pembrolizumab Plus Chemotherapy vs Chemotherapy Alone for Patients with First-line, Advanced Gastric Cancer; The Keynote-062 Phase 3 Randomized Clinical Trial," JAMA Oncology, Sep. 3, 2020, vol. 6(10), pp. 1571-1580.
Vincent et al., "Highly potent anti-CD20-RLI immunocytokine targeting established human B lymphoma in SCID mouse," Mabs, Apr. 2014, vol. 6(4), pp. 1026-1037.

\* cited by examiner

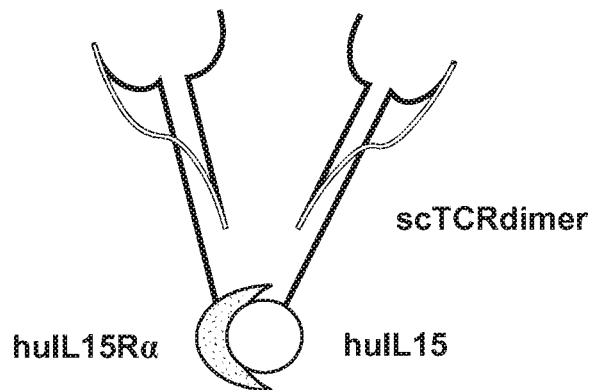
FIG. 1A
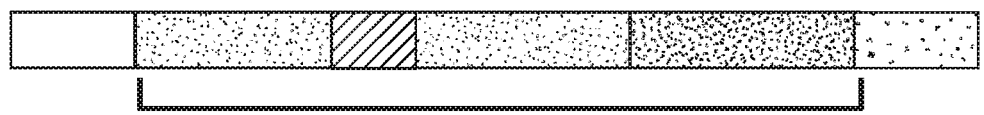
FIG. 1B

FIG. 2B

5'- ACCACCATGGAGACAGACACACTCCTGTTATGGGTACTGCTGCTCTGGGTTCCAGTCCACCGGTCAGT
CAGTGACGCAGCCCGATGCTCGCGTCACTGTCTTCTGAAGGAGCCCTCTCTGCAGTGCAAGTATTC
CTACTCTGGACACCCTTATCTGTTCTGGTATGCCAGTACCCGCAGGGCTGCAGTCAGCTGCTCCTCAAG
TACTATTCAGGAGACCAGTGGTTCAAGGAGTGAATGGCTTCGAGGCTGAGTTCAGCAAGAGTAACTCTT
CCTTCCACCTGCGAAAGCCTGTGTGCAGCGACTGGGACCAAGCTAATTATAAAGCCAGTGTTTGAGCGAGGA
TAGCAACTATCAGTTGATCTGGGCTCTCGGGGCCAAGCTTCTGGGCGGTGTCTGCAATTCAAAAGTCA
GGCAGCGGCGGTGGTTCCGGTGTGAAAGGGCAAGGACAAAAGCAAGATGAGGTGTATCCTGAAAAGGG
TTCAGACTCCAAGATATCTGGTATTCTCAGCAAATAAGAACAATGAGTTTAAATTTTGATTAACTTTCAGAAT
CAAGAAGTTCTTCTTCAGAAATTCAGTCCCTCGAGGCAGGACTCCAGCACTGTACCTCTGCCAGTCTGTCAGG
GCAGCCTAGAAATTCAGTCCCTCGAGGCAGGACTCCAGACTGTACCTCTGCCAGCAGTCTGTCAGG
GGGCGGCACAGAGAAGTTTTTCTTTGGTAAAGGAACCAGAGACTCACAGTTGTAGAGGAACAAGGTGTTC
CCACCCGAGTCGCTGTGTTCTTCCCTGACCACCGTCGGTGAGCTGAGCTGGAAGGCCACACTGGTGT
GCCTGGCCACAGGCTTCTCCCCTGAGCCCGCCACCTTCTGGCCAGAACCCCTCAACGACCCGTCTGCCTGAGC
TGGGGTCAGAGGGTCTCGGAGAATGACGAGTGGAACAACGGGAAATGTAAGACTTCCGTCACCCAGATCGTCAGCCCGA
AGCCGCTGAGGGTCTCCGGACCGTTAACTGGTGAATGTAAGACTTCCGTCACCCAGATCGTCAGCCCGA
ACGGGCTGAGGGTAGACGCAGATATTGATGACCTACTTTATATACGGAAATGTAAGACTTCCGTCACCCAGATCGTCAGCCCGA
GGCCTGGGGTAGACGCAGTTAACTGGTGAATGTAAGACTTCCGTCACCCAGATCGTCAGCCCGA
ATTCAATCTATGCTGTTTTCTCTTGGAGTTGAATGCTACTTTATTTACAAGTTGATTGTTCACCCCAGTTGCAAAGTAACAG
CAATGAAGTGCTCTTCTCTTGGAGTTGAATGCTACTTTATTTACAAGTTGATTGTTCACTTGATGTTCCCGAGATGCAAGTATTCATGATAC
AGTAGAAAATCTGATCATCCTAGCAAACAAACAGTTTGTCTTCTCTAATGGAATGTAACAGTAACAGAATCTGGATGC
AAAGAATGTGAGGAACTGGAGGAAAAAAATATTAAAGAATTTTTGCAGAGTTTTGTACATATTGTCCAAA
TGTTCATCAACACTTCTTGATAA -3'

FIG. 2C

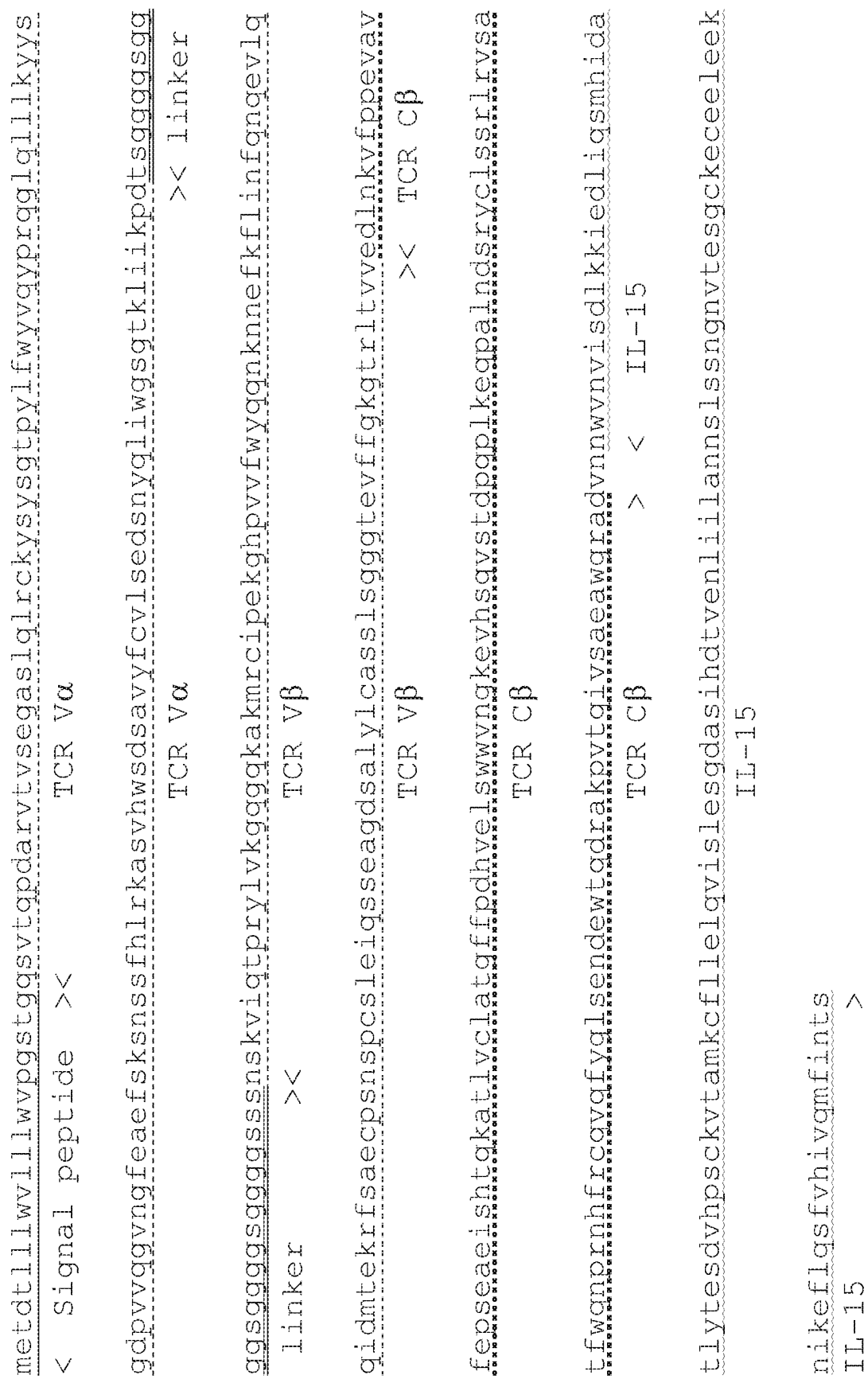

metdtlllwvlllwpgstggsvtqpdarvtvsegaslqlrckysysgtpylfwvvqyprqglqlllkyys
<  Signal peptide  ><       TCR Vα gdpvvqgvngfeaefsksnssfhlrkasvhwsdsavyfcvlsedsnyqliwgsgtkliikpdtsgggsgg
            TCR Vα                                        >< linker ggsgggsgggssnskvigtprylvkgggqkakmrcipekghpvvfwyqnknnefkflinfqnqevlq
linker  ><                               TCR Vβ qidmtekrfsaecpsnspcsleigsseagdsalylcassisgggtevffgkgtrltvvvedlnkvfppevav
                  TCR Vβ                                  >< TCR Cβ fepseaeishtqkatlvclatgffpdhvelswwvngkevhsqvstdpqplkeqpalndsrvclssrlrvsa
                            TCR Cβ tfwqnprnhfrcqvqfyglsendewtqdrakpvtqivsaeawgradvnnwvnvisdkkiedliqsmhida
                      TCR Cβ              >    < IL-15 tlytesdvhpsckvtamkcflleleqlqvislesgdasihdtvenliilannslsissngnvtesgckeceeleek
                                    IL-15 nikeflqsfvhivqmfints
IL-15       >

FIG. 3B

5'-
ACCACCATGGAGACAGACACACTCCTGTTATGGGTACTGCTGCTCTGGGTTCCAGTTCCAGTTGACGCAGCCCGATGC
TCGGGTCACTGTCTCTGAAGGAGCCCTCTCTGCAGATGCAAGTATTCCTACTCTGGACACCTTATCTGTTCTGGTATGTCCAGT
ACCCGCGCCAGGGGCTGCAGCTGCTCCTCAAGTACTATTCAGGAGACCTGGTTCAAGGAGTGAATGCCTTCGAGGCTGAGTTCAGC
AAGAGTAACTCTTCCTTCCACCTGCGGAAAGCCCTCTGTGCACTGGACTCTGTGTACTTCTGTGTTTTGAGCGAGGATAGCAA
CTATCAGTTGATCTGGGGTCTCTGGGGCCAAGCTAATTATAAAGCCAGACACACTAGTGGTGCGCGGTGGTGTTCCGGTG
GCGCGTTCTGGCGGTGGCGGTTCCTCGAGCAATTCAAAAGTCATTCAGATATCTGGTGAAAGGCAAGGACAAAAAGCA
AAGATGAGGTGTATCCCTGAAAAGGGACATCCAGTTGTATTCTGGTATCAACAAGTTTAAATTTTTGATTAACTT
TCAGAATCAAGAAGTTCTTCAGCAGATGACTGAAAAACGATTCTCTGAGTGTCCTTCAAACTCACCTTGCAGCCTAGAAA
TTCAGTCCTCTGAGGCAGAGACTCAGCAGCTGTGCCACTGTAGGGGCGCACAGAGTTCTTTGGTAAAGA
ACCAGACTCACAGTTGTAGAGACAAGTGTTCCCACCCGAGGTCGCTGAGCTGGAGCCATCAGAAGCAGAGATCTCCACAC
CCAAAAGGCCACACTGGCTGTGCCTGGCCAGCGCCCTGACCACGTGGAGCTGAATGGGAAGGAGGTGCACA
GTGGGGTGCCACGACACGCTCAGCAGCCCCTCAATGACTCCAGTTCCGCTCTAGCAGCCTGAGCCAGGGCTCTG
GCCACCTTCTGGCAGAACCCGGTCAAGTCCAGTTGCGAGAATGACGAGTGGACCAGGATAG
GGCCAAACCCGTCACCGAGATCGTCAGCCGAGGCCTGGGTAGAGCAAGACGTTAACGAGCCCAAATCTTCTGACAAACTCACACAT
CTCCACCGTCTCCAACGCGTAACTGGGTGAATGTAAGTGATTTGAAAAAATTGAAGATCTTATTCAATCTATGCATATTGATGCT
ACTTTATATACGGAAAGTGATGTTCACCCCAGTTGCAAAGTAACAGCAATGAAGTGCTTTCTCTTGGAGTTACAAGTTATTTCACTTGA
GTCCGGAGATGCAAGTATTCATGATACAGTAGAAATCTGATCATCCTAGCAAACACAGTTTGTCTTCTAATGGAATGTAACAGAAT
CTGATGCAAAGAATGTGAGGAACTGAGGAGCAAAAAATATTAAAGAATTTTTGCAGAGTTTTGTACATATTGTCCAAATGTTCATCAAC
ACTTCTTGATAA -3' metdtlllwvillwvllwpgstqgsvtqqsvtqpdarvtvseqaslqlrckvsvsqtpvlfwvvqyprqqlqlllkvys
<  Signal peptide  ><              TCR Vα gdpvvggvngfeaefsksnssfhlrkasvhwsdsavyfcvlsedsnyqliwsgtkliikpdtsgggsgq
                        TCR Vα                                    >< linker ggsgggsgggsgggssnskviqtpryylvkgggqkakmrcipekghpvvfwyqqnknnefkflinfqngevlq
linker ><                          TCR Vβ qidmtekrfsaecpsnspcsleigssseagdsalylcasslsgggtevffgkgtrltvvedlnkvfppevav
                    TCR Vβ                                    >< TCR Cβ fepseaeishtqakatlvclatgffpdhvelswwvngkevhsgvstdpqplkeqpalndsryclssrlrvsa
                    TCR Cβ tfwqnprnhfrcqvqfyqlsendewtqdrakpvtqivsaeawgradvnepkssdkthtspppsptrnwvi
                    TCR Cβ                        >  <  linker  >  <IL-15 sdlkkiedligsmhidatlytesdvhpsckvtamkcfllelqvislesgdasihdtvenliilannslssn
                                        IL-15 gnvtesgckeceeleeknikefliqsfvhivqmfints
        IL-15                    >

5'- ACCACCATGGAGACAGACACACTCCTGTTATGGGTACTGCTGCTCTGGGTTCCACCGGTCAGT
CAGTGACGCAGCCCGATGCTCGCGCTGTCACTGTCTCTGAAGGAGCCTCTGCAGCTGAGATGCAAGTATTC
CTACTCTGGACACCTTATCTGTTCTGGTATGTCCAGTACCCGGCAGGGCTGCAGCCTGCTCCTCAAG
TACTATTCAGGAGAGACCCAGTGGTTCAAGGAGTGAATGGCTTCGAGGCTGAGTTCAGCAAGAGTAACTCTT
CCTTCCACCTGCGGAAAGCCTCTGTGCACTGGGACTGGGACCAAGCTAATTATAAAGCCAGTAGTGGTGGGT
TAGCAACTATCAGTTGATCTGGGCTCTGGGCGCCAAGCAAATTCAAAAGTCA
GGCAGCGGCGGTGGTGTTCCGGTGGCCGGTGCTGGAAAGGGCAAGGACAAAAAGCAAAAGATGAGTTTAAATTTTTGATTAACTTTCAGAAT
TTCAGACTTGTATTCTCAGCAAATATAAGAACAATGAGTTTTGATTAACTTTCAAACTCACCTT
ACATCCAGTTGTCTTCAGAAATTCAGTCCTCTGAGGCAGGACTCAGCTGTACCTCTGTGCCAGTCTGTCAGG
GCAGCCTAGAAATTCAGTCCTCTGAGGCAGGACTCAGCTGTACCTCTGTGCCAGTCTGTCAGG
GGCGGCACAGAAGTTTTCTTTGTGAGCCATCCAGAAGCCAGAGATCTCCCACACCCAAAAGGCCACACTGGTGT
CCACCCGAGGTCGCCTGTGTTCTTCCCTGACCACGTGGAGCTGGTGGGTGAATGGACTCCAGATACTGCCTGAGC
GCCTGGCCACAGGCTTCTCGGCCACAGCGTTCAAGGAGCAGCCCCGCAACCACTTCCGCTGTTCAAGTCAGTTCT
TGGGGTGCACTCAGCAGGTCTCCGCCACCTCTGCGAGAACCCCCCCGCAACCCGTCACCCAGATCGTCAGCGCCGA
AGCCGCCTGAGGGTCTCGGAGAATGACGAGTGAACATCACGTGACCCAGGCCAAACCCCCCATGCCCTCACCTGG
GGCCTCTGGGGTAGAGCTTGTACTCCAGGAGCGGTACATTTGTAACTCTGGTTTCAAGCGTAAAGCCGGCA
GTCAAGAGCTACAGCTTGTACTCCAGGAGCGGTACATTTGTAACTCTGGTTTCAAGCGTAAAGCCGGCA
CGTCCAGCAGTGAGTCGTTGAACAAGTGCGCCACTGGACTGGACAACACAGCCCACAGTCTCAA
ATGCATTAGACCCGCAGCTTCATCTCCAGCTCAAACTCCCACAGCCCACAACACAGCAGTCATGAGTCCCG
GGCTCCCAGTCTGATGCCTTCAGACAGAACAGCCTTCAAAATCACCTTCCACAGAACCAAGAACCTTCATGAGTCCTCCC
ACGGCACCCCAGTCTGATGCCTTCAGACAGAACAGCCTTCAAAATCACCTTCCACAGAACCAAGAACTGGAACTTCACAGCCATCCGCCTCTCCCACCAGCCAGG
TGTGTATCCCACAGGGCCACAGCCGACACCACTTGATAA-3'

FIG. 4C metdtlllwvlllwvpgstggsvtgpdarvtvsegaslqlrckvysysgtpylfwyvqyprqglqlllkyys
< Signal peptide >< TCR Vα gdpvvgvngfeaefsksnssfhlrkasvhwsdsavyfcvlsedsnyqliwgstkliikpdtsgggsgg
TCR Vα >< linker ggsgggsgggssnskvigtprylvkgggkakmrcipekghpvvfwygqnknnefkflinfqnqevlq
linker >< TCR Vβ qidmtekrfsaecpsnspcsleiqsseagdsalylcasslsgggtevffgkgtrltvvvedlnkvfppevav
TCR Vβ >< TCR Cβ fepseaeishtqkatlvclatgffpdhvelswwvngkevhsqvstdpqplkeqapalndsryclssrlrvsa
TCR Cβ tfwqnprnhfrcqvqfyqlsendewtqdrakpvtgivsaeaewgradvnitcpppmsvehadiwvksyslys
TCR Cβ >< IL-15RaDE3 reryicnsgfkrkagtsslteccvlnkatnvahwttpslkcirpaasspssnntaattaaivpgsqlmpsks
IL-15RaDE3 pstgtteisshesshgtpsqttaknweltasashqppgvypqghsdtt
IL-15RaDE3 >

FIG. 5B

5'- ACCACCATGGAGACAGAGACACACTCCTGTGTTATGGGTACTGCTGCTCTGGGTTCCAGTTCCACCGGTCAGT
CAGTGACGCAGCCCGATGCTCGCCTCTGAAGGAGAGCCTCTGAAGGAGAGCCTCAGCTGAGATGCAAGTATTC
CTACTCTGGGACACCTTATCTGTTCTGGTATGTCCAGTGCAGGGCTGCAGCTGCAGCTGCTCCTCAAG
TACTATTCAGGAGACCCAGTGGTTCAAGGAGTGAATGGCTTCGAGTGCTTCAGCAAGAGTAACTCTT
CCTTCCACCTGCGGAAAAGCCCTCGTGCACTGGAGCGACTCTGTGCTCTGTGTACTTCTGTTTTGAGCGAGGA
TAGCAACTATCAGTTGATCTGGGACCAAGCTAATTATAAAGCCAGACACTAGTGGTGGCGGT
GGCAGCGGCGGTGGTTCCGGTGCGGCCTCTGGCGCGGTTCTGGCGTTCCTGAGCAATTCAAAAGTCA
TTCAGACTCCAAGATATCTGGTGAAGGACAAAGCAAAGATGAGGTGTATCCCTGAAAAGGG
ACATCCAGTTGTATTCAGCAAATAGACATGAGTTTCTCTGCGAGTGTCCTTCAAACTCACCTT
CAAGAAGTTCTTCAGAAATTCAGTTTTTCTTTGGTAAAGAACCAGACTCACAGTTGTAGAGCAGTCTGTCAGG
GCAGCCTAGAAATCAGTTTTTCTTTGGTAAAGAACCAGACTCACAGTTGTAGAGCAGTCTGTCAGG
GGGCGGCACAGAGGTCGCTGTGTTTGAGCCATCAGAAGCAGAGATCTCCCACACCCAAAAGGCCACACTGGTGT
CCACCCGAGGTCGCTGTGTTTGAGCCATCAGAAGCAGAGATCTCCCACACCCAAAAGGCCACACTGGTGT
GCCTGGCACAGGCACGAGCCTCTTCCCTGACCAGCCCCTCAAGCAGCCCTCAATGACTCCAGATACTGCCGAGC
TGGGGTCAGCACGAGCCTCTCTGCGCCACCTTCTGGCAGAACCACTTCCGTGTCAAGTCCAGTTCT
AGCCGCCTGAGGGTCTCGGCAGAATGACGAGTGGACCCCAGGATAGGGCCAAACCCGTCACCCAGATCGTCAGCCCCGA
ACGGCCTGGGGTAGAGCAGTTAACATCACGTGCCCCCCATGTCCGTGGAACACGCAGACATCTGG
GGCCTGGGGTAGAGCAGTTAACATCACGTGCCCCCCATGTCCGTGGAACACGCAGACATCTGG
GTCAAGAGCTACAGTCCAGGAGCGGTACTCCAGGGAGCGGTACATTTGTAACTCTGGTTTCAAGCGTAAAGCCGGCA
CGTCCAGCCTGACGGAGTGCGTGTTTGAACAAGGCCACGAATGTCGCCCACTGGACAACCCCCCCAGTCTCAA
ATGCATTAGA -3'

FIG. 5C metdtlllwvlllwvpgstggsvtqpdarvtvsegaslqlrckysysgtpylfwyvqyprgqlqlllkyys
< Signal peptide ><                        TCR Vα gdpvvqgvngfeaefsksnssfhlrkasvhwsdsavyfcvlsedsnyqliwsgtkliikpdtsgggsgg
                    TCR Vα                               >< linker ggsgggsgggssnskviqtpylvkgqgkakmrcipekghpvvfwyqqnknnefkflinfqnqevlq
linker     ><                                   TCR Vβ qidmtekrfsaecpsnspcsleiqsseagdsalylcasslsgggtevffgkgtrltvvedlnkvfppevav
                      TCR Vβ                                 >< TCR Cβ fepseaeishtqkatlvclatgffpdhvelswwvngkevhsqvstdpqplkeqpalndsryclssrlrvsa
                                          TCR Cβ tfwqnprnhfrcqvqfyqlsendewtqdrakpvtqivsaeawgradvnitcpppmsvehadiwvksvslvs
                              TCR Cβ         >   <         IL-15RaSushi Rervicnsgfkrkagtssltecvlnkatnvahwttpslkcir
               IL-15RaSushi           >

FIG. 6B

5'-
ACCACCATGGGAGACAGAGACACACTCCCTGTTATGGGTACTGCTGCTCTGGGTTCCAGTTCCACGGTCAGTCAGTGACCGCAGCCCGATGC
TCGGCGTCACTGTCTCTGAAGGAGCCTCTGCAGCTGAGATGCAAGTATTCCTGGGACACTTGTTCTGTTCTGAGGCTGTATGTCCAGT
ACCCGCGGCAGGGCTGCAGTGCTCCTCAAGTACTATTCCAGGAGACCCAGTGGTTCAAGGAGTGAATGGCTTCGAGGCTGAGTTCAGC
AAGAGTAACTCTTCCTGCACCTGGGCTGCAGTCTCTGGGACCAAGCTAATTATAAAGCCAAGCTAGTGGTGGCCAGCGGGTGGTTCCGGTG
CTATCAGTTGATCTGGGCGTCTCTGGGACCAAGCTAATTATAAAGCCAAGCTAGTGGTGGCCAGCGGGTGGTTCCGGTG
GCGCGGTTCTGGCGGTGCCGAAAGGTGTATCCCTGAAAGTTCTTCAGCAGAAGACATCCAGAGACTCAGAATATCTGAAAGGGCAAGACAAAAAGCA
AAGATGAGGTGTATCCCTGAAAGTTCTTCAGCAGAAGACATTGACTACCCTGTGCCCAGTCTGTGTCCCACGAAGTTTCTTGGTAAAGGA
TCAGAATCAAGAAGTTCTTCAGCAGAAGACTGTACCCTGTGCCCAGTCTGTGTCCCACAGAAGTTTCTTGGTAAAGGA
TTCAGTCCTCTGAGGCAGGAGACTGTACCCTGTGCCCAGTCTGTGTCCCACAGAAGTTTCTTGGTAAAGGA
ACCAGACTCACAGTTGTAGAGAGACCTGGAACAAGGTGTTCCACACCGAGTGTTTGAGCCATGGAGCTGAGTGGGTGAATGGGAAGGAGGTGCACA
CCAAAAGGCCACACTGGTGTGCCTGGCCACAGGCCCCTCAAGGAGCCAGCCCCTCAAGACTACTCCGAGGCCCTGAGCCGCCCTGAGGGTCTCG
GTGGGGGTCAGCACACGGACCCCCGCAGAACCCCCGCAACCACTTCCGCTGTCAAGTTCCAGTGGAGAATGACGAGTGACCCAGGATAG
GCCACCCTTCTGGCAGAAACCCGTCACCGAGATCGTCAGCGCCCAGAGGCCAGACGCAGACAGACAGACATCTTCTGACAAAAACTCACACAT
GGCCAAACCCGTCACCGAGATCGTCAGCGCCCAGAGGCCAGACGCAGACAGACAGACATCTTCTGACAAAAACTCACACAT
CTCCACCGTCCAAGCGTACCGTACATCACGTGCCCCCCCATGTCCGTGAACACGCCAGACATCTGGTCAAGAGCTACAGCTTGTACTCC
AGGGAGCGGTACATTGTAACTCTGTTTCAAGCGTAAAGCCCGGCCACGTCCAGCCTGGACGGAGTGCGTGTTGAACAAGGCCACGAATGT
CGCCCCACTGGACAACCCCCCAGTCTCAAATGCATTAGATGATAA    -3'

FIG. 6C metdtlllwvlllwpgstgqsvtqpdarvtvsegaslqlrckysysgtpylfwvvqyprqglqlllkyys
< Signal peptide ><              TCR Vα gdpvvqgvngfeaefsksnssfhlrkasvhwsdsavyfcvlsedsnyqliwgstkliikpdtsgggsgg
                             TCR Vα                   >< linker ggsgggsgggssnskviqtprylvkgggkakmrcipekghpvvfwyqqnknnefkflinfqnqevlq
< linker      ><                              TCR Vβ qidmtekrfsaecpsnspcsleigsseagdsalylcasslsgggtevffgkgtrltvvvedlnkvfppevav
                               TCR Vβ                            >< TCR Cβ fepseaeishtqkatlvclatgffpdhvelswwvngkevhsqvstdpqplkeqpalndsryclssrlrvsa
                             TCR Cβ tfwqnprnhfrcqvqfyglsendewtqdradrakpvtqivsaeawgradvnepkssdkthtsppsptritcppp
                             TCR Cβ                          > < linker   > < msvehadiwvksyslvsreryicnsgfkrkagtssltecvlnkatnvahwttpslkcir
                      IL-15RaSushi                          >

FIG. 14A

NWVNVISDLKKIEDLIQSMHIDATLYTESDVHPSCKVTAMKCFLLELQVISLESGDASI
HDTVENLIILANNSLSSNGNVTESGCKECEELEEKNIKEFLQSFVHIVQMFINTS

FIG. 14D c264scTCR-hmt-IL15D8A gene

5'-
ACCACCATGGAGAGACAGACACACTCCCTGTTATGGGTACTGCTGCTCTGGGTTCCAGTTCCAGTGGTCTCAGTCAGTGACGCAGCCCGATGC
TCGCGGTCACTGTCTCTGAAGGAGCCTCTGCAGCGGAGATGCAAGTATTCCTACTGGGAGATGCAAGTATTCCTACTCTGTTCTGGTATGTCCAGT
ACCCGGGCAGGGCTGCAGTCTGCTCCTCAAGTACTATTCAGGAGAGTAGCCCCTCGTGTCCAGCGGAGACTGGATGGCTTCGAGGCTGAGTTCAGC
AAGAGTAACTCTTCCTTCCACTGGCGAAAAGCCCTCTGGGACCAAGCTAATTATAAAGCCAGTACTAGTGGCGCAGCGGGTGGTGTTCCGGTG
CTATCAGTTGATCTGGGCGGTGGCGGTTCCTCGACCAGTCATTCAGAGTCAAAAGTCATTCAGACTCCAAAATACACCACAAATCAGAACAAGCA
GCGCGGTTCTGGCGGTGGCGGTTCCCTGAAAAGGCAGACATCTGAAAGGAGGACATCTGAAAAGGAGGACATCTGAAAGAGTTTAAATTTTTGATTAACTT
AAGATGAGGTGTATCCCTGAAAGAGTTCTTCAGCGAAAATAGACATTCTCTGCGAAAACGATTCTCTCTGCAGTGTCCTTCAAACTCACCTTGCAGCCTAGAAA
TCAGAATCAAGAAGTTCTTCAGCAGCCTGCAGTACTAGCACATGACTGAAACGATTCTCTGCGAGTGTCCTTCAAACTCACCTTGCAGCCTAGAAA
TTCAGTCCCCTCGAGGCAGAAGTTGTAGAGACCTGGAGGAGCACCTGAACAAGGTGCTCCACCAGTGTCCCACCAGCCATCAGAAGCAGAAGAGATCTCCCACAC
ACCAGACTCACAGTTGTAGAGACCTGAACAAGGTGTTCCCACAGCCTGTGTGTGGTGGTGTGGTGAAGGAGGTGCACA
CCAAAAGGCCACACTGGTGTGCCTGGCCACCAGCCCCCTGAAGCAGCCCCCTGAACCACTCCCTGTCAAGTCCCAGTTCCAGTTCTACGGGCCTGT
GTGGGTCTTCTGGCCAGACCCCACCAGATCGTAACGTGTAACGCTTAACCAAGCCAGGCCAGAATGACGAGTGACAAATCTTCTGACAAAACTCACACAT
GGCCAAACCCGTCTCCACCGATCTCTCAAGCGCGTCTAATGGTGAATGTAATAAGTGCTTTGAAAAAAATTGAAGATCTTATTCAATCTATGCATATGATGCT
CTCCACCGTCTCCACCGATCTCTCAAGCGCGTAACTGGTGAATGTAATAAGTGCTTTGAAAAAAATTGAAGATCTTATTCAATCTATGCATATGATGCT
ACTTTATATACGGAAAGTGATGTTCACCCAGTTGCAAAGTAACAGCAAGTGAAGTGCTTTCTCTGGAGTTACAAGTTATTTCACTTGA
GTCCCGAGATGCAAGTCAAGTACGATATTCATGATGATCATCCTCCTAGCAAAAACAGTTTGTCTTCAATCATCCTAATGGAATGTAACAGAAT
CTGGATGCAAGAATGTGAGGAACTGAAGAATTGAAGAATGTCAGAGTTTTGCAGAGTTTTGTACATATTGTCCAAATGTTCATCAAC
ACTTCTTGATAA
-3'

FIG. 14E c264scTCR-hmt-IL15D8N gene

5'-
ACCACCATGGAGACAGACACACTCCTGTTATGGGTACTGCTGCTCTGGGTTCCAGGTTCCAGTCAGTGACGCAGCCCGATGC
TCGCGTCACTGTCTCTGAAGGAGCCCTCTGCAGTGAGATGCAAGTATTCCTACTCTGGACACCTTATCTGTCTTCTGGTATGTCCAGT
ACCCGCGGCAGGGCTGCAGTGCTCCTCAAGTACTATTCAGGAGAGACCAGTGGTTCAAGGAGTGAATGCTTCGAGGCTGAGTTCAGC
AAGAGTAACTCTTCCTTCCACTGGGGCTCTGGGACCAAGCTCGAGCAGCTAATTATAAAGCCTAATGCAGCAACTAGTGGTGGCAGCGGCGGTGGTTCCGGTG
CTATCAGTTGATCTGGGCTCTGGGACCAAGCTCGAGCAGCTAATTATAAAGCCTAATGCAGCAACTAGTGGTGGCAGCGGCGGTGGTTCCGGTG
GCGGCGGTTCTGGCGGTGGCTCCCTGAAAGGAGTGTACCTGAAAGGAGTGACATCAGCACATCAGTGTATTCTGTGACTGAACAAAGTCATTGATTCAATTT
AAGATGAGGTGTACCCTGAAAGGAGTGACATCAGCACATCAGTGTATTCTGTGACTGAACAAAGTGAGTTAATTTTGATTAACTT
TCAGAATCAAGAAGTTCTTCAGCAGGACACTCAGCAAATGACTGAGCAAAACGATTCTCTGAGTGTCCTTCAAACTCACCTTGCAGCCTAGAAA
TTCAGTCCCTCTGAGGCAGGACTCAGAGAGACTGTTCCCCACCTCTGTGCCAGCAGTGGTCGCACACACGAAGCAGAGATCTCCCACAC
ACCAGACTCACAGTTGTAGAGACCTGTTGCCTGGCCTTCTCGAGAACAAGGTCTTCCTGAGCCATCAGAAGCAGAGATCTCCCACAC
CCAAAAGGCCACACTGGTGTGCCTGGCCACAGGCTTCTTCCCTGAAGCCAAGAACCATCAGTGACTTCCTCCAGATGCTCCGCAGCAGAAT
GTGGGCGTCAGCGAGCTGGCCAGACCCGTCCAAACACATTCCGCTCAAGTCCAGTTCCGCTTGTCCAGTAGAGACAGAAT
GCCACCTTCTGGCAGAACCCCGTCTCCAACGCGTAACTGGGTAACTGGGTGAATGTAAAATAATTTGAAAAAATAATTGAAGAACAAATCTTATTCAATCTATGCATATT GATGCT
CTCCACCGTCTCCAACGCGTAACTGGGTGAATGTAAAATAATTTGAAAAAATAATTGAAGAACAAATCTTATTCAATCTATGCATATT GATGCT
ACTTTATATACGGAAAGTGATGTTCACCCAGTTGCAAAGTAACAGCAATGAAGTGCTTCTTCCTTTGGAGTTACAAGTTATTCACTTGA
GTCCGGAGATGCAAGTATTCATGATCACAGTAGAATCCTAGCAAACAATCTGATCATCCGAAACAACAGTTGTGTCTTCTAATGGAATGTAACAGAAT
CTGGATGCAAAGAATGTGAGGAACTGGAAGAACAATATTAAAGAATTTTGCAGAGTTTTGTACATATGGAAGAATTTTAAAGAATATTAAAGAATTTTTGCAGAGTTTTGTACATATGGAAGAATTTTAAAGAATATTAAAGAATTTTTGCAGAGTTTTGTACATATTGTCCAAATGTTCATCAAC
ACTTCTTGATAA -3'

FIG. 14F c264scTCR-hmt-IL15D8A protein metdtlllwvlllwpgstggsvtqpdarvtvsegaslqlrckysysgtpylfwyvqyprqglqlllkyys  
`< Signal peptide ><`       TCR Vα gdpvvqgvngfeaefsksnssfhlrkasvhwsdsavyfcvlsedsnyqliwgsgtkliikpdtsgggsgq  
                                 TCR Vα                                  `>< linker` ggsggggsggggssnskviqtpryvkgqgqkakmrcipekghpvvfwyqqnknnefkflinfqnqevlq  
`linker ><`       TCR Vβ qidmtekrfsaecpsnspcsleiqsseagdsalylcasslsgggtevfffgkqtrltvvedlnkvfppevav  
                      TCR Vβ                                `>< TCR Cβ` fepseaeishtqkativclatgffpdhvelswwvngkevhsqvstdpqplkeqpalndsryclssrlrvsa  
                                    TCR Cβ tfwqnprnhfrcqvqfyqlsendewtqdrakpvtqivsaeaawgradvnepkssdkthtspppsptrnwvni  
             TCR Cβ                         `>< linker >` sAlkkiedlligsmhidatlytesdvhpsckvtamkcfllelqvislesgdasihdtvenliilannslssn  
*                              IL-15 D8A gnvtesgckeceeleeknikeflqsfvhivqmfints  
           IL-15 D8A             `>`

FIG. 14G c264scTCR-hmt-IL15D8N protein metdtlllwvlllwpgstggsvtqpdarvtvsegaslqirckysysgtpylfwvvqyprgglqlllkyys
<‾‾‾ Signal peptide ‾‾‾><‾‾‾‾‾‾‾‾‾‾‾‾‾‾‾‾‾‾‾‾‾‾‾ TCR Vα gdpvvqgvngfeaefsksnssfhlrkasvhwsdsavyfcvlsedsnyqliwgstkliikpdtsgggggsgg
‾‾‾‾‾‾‾‾‾‾‾‾‾‾‾‾‾‾‾‾‾‾‾‾‾‾‾‾‾ TCR Vα                                        ‾‾‾‾‾‾‾‾‾‾‾‾‾‾‾‾‾‾‾‾‾‾‾‾‾‾‾‾‾><‾‾ linker ggsgggsggggsssnskviqtpryllvkgggqkakmrcipekghpvvfwyqqnknnefkflinfqnqevlq
 linker ‾‾‾><‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾ TCR Vβ qidmtekrfsaecpsnspcsleiqsseagdsalylcasslsgggtevffgkgtrltvvedlnkvfppevav
‾‾‾‾‾‾‾‾‾‾‾‾‾‾‾‾‾‾‾‾‾‾‾‾‾‾‾ TCR Vβ ‾‾‾‾‾‾‾‾‾‾‾‾‾‾‾‾‾‾‾‾‾‾‾‾‾‾><‾‾‾‾‾‾‾‾‾‾ TCR Cβ fepseaeishtgkativclatgffpdhvelswwvngkevhsqvstdpaplkeqpalndsryclssrlrvsa
‾‾‾‾‾‾‾‾‾‾‾‾‾‾‾‾‾‾‾‾‾‾‾‾‾‾‾‾‾‾‾‾‾‾‾‾‾‾‾‾‾‾‾ TCR Cβ ‾‾‾‾‾‾‾‾‾‾‾‾‾‾‾‾‾‾‾‾‾‾‾‾‾‾‾‾‾‾‾‾‾‾‾‾‾‾‾‾‾‾‾ tfwqnprnhfrcqvqfyqlsendewtqdrakpvtgivsaeawqradvnepkssdkthtspppsptrnwvnvi
‾‾‾‾‾‾‾‾‾‾‾‾‾‾‾‾‾‾‾‾‾‾‾‾‾‾‾‾‾‾‾‾‾ TCR Cβ ‾‾‾‾‾‾‾‾‾‾‾‾‾‾‾‾‾‾‾‾‾‾‾‾‾‾‾‾‾‾‾‾><‾‾ linker ‾‾>< sNlkkiedliqsmhidatlytesdvhpsckvtamkcflllelqvislesgdasihdtvenliilannslssn
  *                                      ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
         IL-15 D8N gnvtesgckeceeleeknikeflqsfvhivqmfints
‾‾‾‾‾‾‾‾‾‾‾‾‾‾‾‾‾‾‾‾‾‾‾‾‾‾‾‾‾‾‾‾‾‾‾‾‾>
  IL-15 D8N

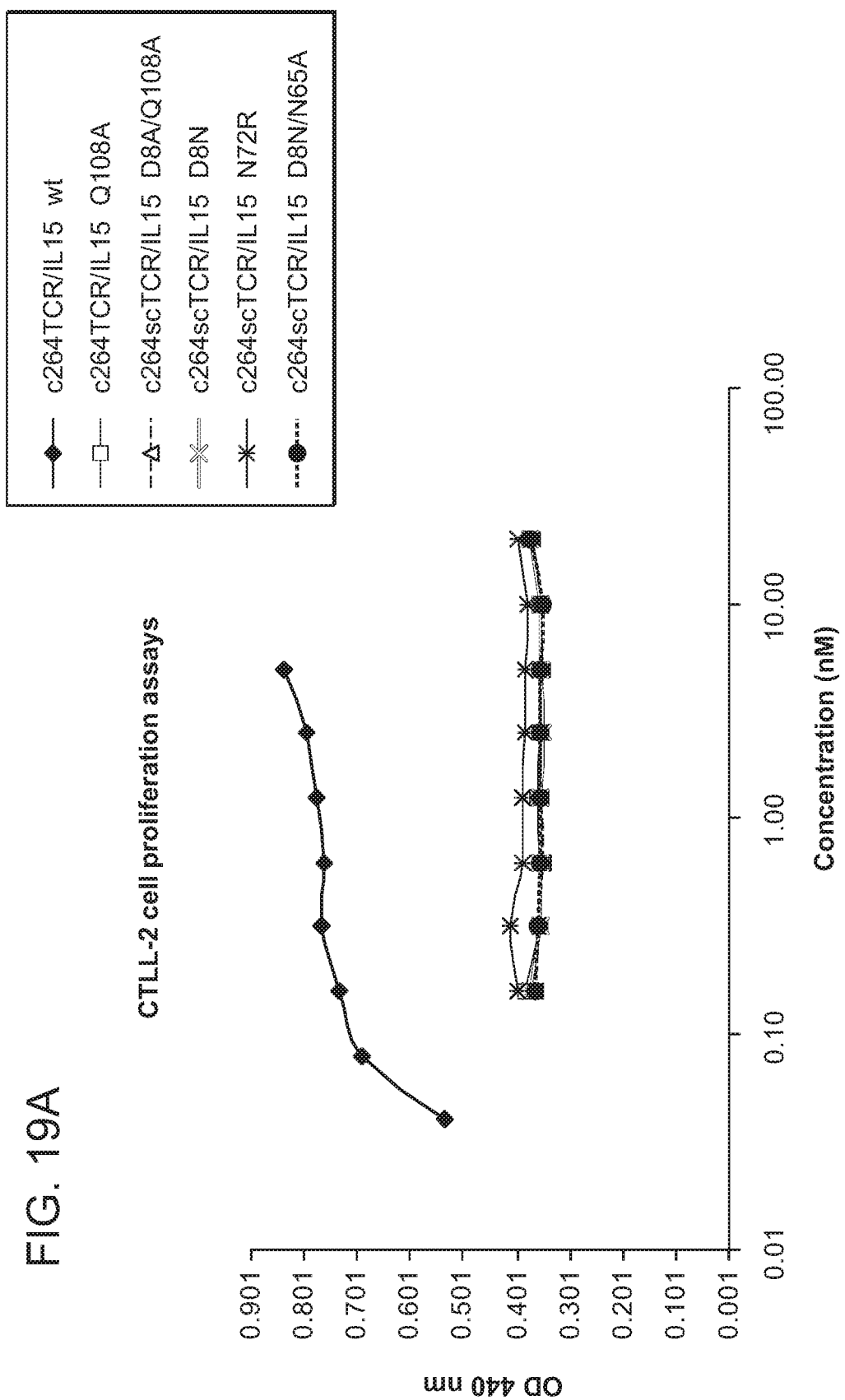

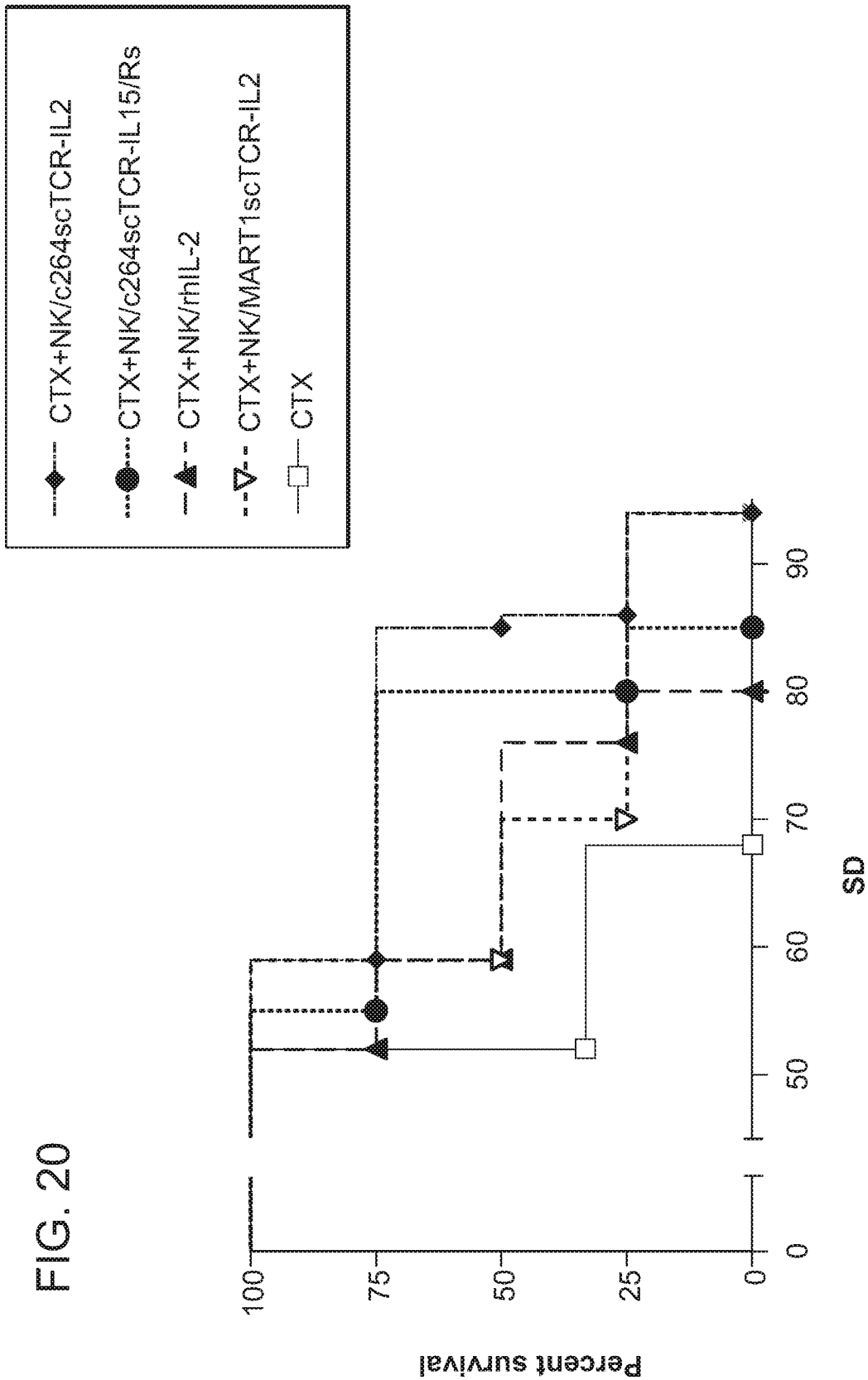

FIG. 21

Table 1

| Mutants | Position | 8 | 61 | 65 | 72 | 108 | IL15Rβγ C receptor binding | IL15Rα binding | Proliferation activity |
|---|---|---|---|---|---|---|---|---|---|
|  | WT aa | D | D | N | N | Q | + | + | + |
| 1 | 8 | N |  |  |  |  | - | + | - |
| 2 | 8 | A |  |  |  |  | - | + | - |
| 3 | 61 |  | A |  |  |  | - | + | - |
| 4 | 65 |  |  | D |  |  | - | + | - |
| 5 | 65 |  |  | A |  |  | - | + | - |
| 6 | 72 |  |  |  | D |  | 3+ | + | 3+ |
| 8 | 72 |  |  |  | R |  | - | + | - |
| 9 | 108 |  |  |  |  | A | - | + | - |
| 10 | 8+65 | N |  | A |  |  | - | + | - |
| 11 | 8+108 | A |  |  |  | A | - | + | - |
| 12 | 8+65 | S |  | R |  |  | - | + | - |

NWVNVISDLKKIEDLIQSMHIDATLYTESDVHPSCKVTAMKCFLLELQVISLESGDASI
HDTVENLIIANNSLSSNGNVTESGCKECEELEEKNIKEFLQSFVHIVQMFINTS

FIG. 22A

AACTGGGGTGAATGTAATAAGTGATTTGAAAAAAATTGAAGATCTTATTCAATCTATGCA
TATTGATGCTACTTTATATACGGAAAGTGATGTTCACCCCAGTTGCAAAGTAACAGCAA
TGAAGTGCTTTCTCTTGGAGTTACAAGTTATTTCACTTGAGTCCGGAGATGCAAGTATT
CATGATACAGTAGAAAATCTGATCATCCTAGCAAACAACAGTTTGTCTTTCTAATGGGAA
TGTAACAGAATCTGGATGCAAAGAATGTGAGGAACTGGAGGAAAAAATATTAAAGAAT
TTTTGCAGAGTTTTGTACATATTGTCCAAATGTTCATCAACACTTCTTGA

FIG. 22B

FUSION MOLECULES AND IL-15 VARIANTS

CROSS-REFERENCE TO RELATED APPLICATIONS

This application is a continuation of U.S. Ser. No. 17/716,986, filed Apr. 8, 2022, now U.S. Pat. No. 11,673,932, which is a continuation of U.S. Ser. No. 16/654,958, filed Oct. 16, 2019, now U.S. Pat. No. 11,365,231, which is continuation application of U.S. Ser. No. 15/254,713, filed Sep. 1, 2016, now U.S. Pat. No. 10,450,359, which is continuation application of U.S. Ser. No. 13/946,438, filed Jul. 19, 2013, now U.S. Pat. No. 9,464,127, which is a continuation of U.S. Ser. No. 12/151,980, filed May 9, 2008, now U.S. Pat. No. 8,492,118, which claims the benefit of U.S. Provisional Application Ser. No. 60/928,900, filed May 11, 2007, the entire contents of each of which are hereby incorporated herein by reference.

GOVERNMENT SUPPORT

Research supporting this application was carried out by the United States of America as represented by the Secretary, Department of Health and Human Services.

SEQUENCE LISTING

The instant application contains a Sequence Listing submitted as an electronic XML file named "PAT000719US011.xml", having a size in bytes of 50,000 bytes, and created on Apr. 24, 2023. The information contained in this electronic file is hereby incorporated by reference in its entirety pursuant to 37 CFR $1.52 (e) (5).

BACKGROUND OF THE INVENTION

T Cell Receptors (TCR) are primary effectors of the immune system that have unique advantages as a platform for developing therapeutics. While antibody therapeutics are limited to recognition of pathogens in the blood and extracellular spaces or to protein targets on the cell surface, T cell receptors can recognize antigens displayed with MHC molecules on the surfaces of cells (including antigens derived from intracellular proteins). Depending on the subtype of T cells that recognize displayed antigen and become activated, T cell receptors and T cells harboring T cell receptors can participate in controlling various immune responses. For instance, T cells are involved in regulation of the humoral immune response through induction of differentiation of B cells into antibody producing cells. In addition, activated T cells act to initiate cell-mediated immune responses. Thus, T cell receptors can recognize additional targets not available to antibodies.

T-cells are a subgroup of cells which together with other immune cell types (polymorphonuclear, eosinophils, basophils, mast cells, B-, NK cells) constitute the cellular component of the immune system. Under physiological conditions T-cells function in immune surveillance and in the elimination of foreign antigen. However, under pathological conditions there is compelling evidence that T-cells play a major role in the causation and propagation of disease. In these disorders, breakdown of T-cell immunological tolerance, either central or peripheral is a fundamental process in the causation of autoimmune disease.

The TCR is believed to play an important role in the development and function of the immune system. For example, the TCR has been reported to mediate cell killing, increase B cell proliferation, and impact the development and severity of various disorders including cancer, allergies, viral infections and autoimmune disorders.

It thus would be desirable to provide novel targeting agents based on T cell receptors, as well as methods for producing and using such agents for therapeutic and diagnostic settings. Accordingly, it would be particularly desirable to provide such molecules that would have certain advantages in comparison to prior art complexes based on antibody targeting.

Moreover, it is desirable to use the TCR to target various effector molecules to the disease site where they can provide therapeutic benefit without the side effects associated with system non-targeted activity. One such is IL-15, a member of the four alpha-helix bundle family of lymphokines. IL-15 plays a multifaceted role in development and control of the immune system. More specifically, IL-15 influences the function, development, survival, and proliferation of CD8+ T cells, NK cells, killer T cells, B cells, intestinal intraepithelial lymphocytes (IEL) and antigen-presenting cells (APC). It has been demonstrated that both IL-15−/−, and IL-15Rα−/− transgenic mice lack peripheral NK and killer T cell populations, certain IEL subsets, and most memory phenotype CD8+T cells, suggesting IL-15 plays role in the development, proliferation or/and survival of these cell types. The IL-15 receptor (R) consists of three polypeptides, the type-specific IL-15R alpha ("IL-15Rα" or "IL-15Ra"), the IL-2/IL-15Rbeta ("IL-2Rβ" or "IL-15Rb"), and the common gamma chain ("γC," or "gC" which is shared by multiple cytokine receptors).

IL-15 signaling can occur through the heterotrimeric complex of IL-15Rα, IL-2Rβ and γC; through the heterodimeric complex of IL-2R13 and γC. A novel mechanism of IL-15 action is that of transpresentation in which IL-15 and IL-15Rα are coordinately expressed by antigen-presenting cells (monocytes and dendritic cells), and IL-15 bound to IL-15Rα is presented in trans to neighboring NK or CD8 T cells expressing only the IL-15RβγC receptor. As a co-stimulatory event occurring at the immunological synapse, IL-15 transpresentation now appears to be a dominant mechanism for IL-15 action in vivo and appears to play a major role in tumor immunosurveillance (Waldmann, T A, 2006, *Nature Rev. Immunol.* 6:595-601). Soluble IL-2Rα subunits, inducing isoforms containing a deletion of exon3 and the so-called "sushi" domain at the N terminus, have been shown to bear most of the structural elements responsible for cytokine binding. Whereas IL-2Rα alone is a low affinity receptor for IL-2 (Kd_10 nM), IL-15Rα binds IL-15 with high affinity (Kd_100 pM). Thus soluble IL-2Rα and IL-15 are able to form stable heterodimeric complexes in solution and these complexes are capable of modulating (i.e. either stimulating or blocking) immune responses via the intermediate or high affinity IL-15R complex (Mortier et al. 2006. *J Biol Chem* 281: 1612-1619; Stoklasek et al. 2006. *J Immunol* 177: 6072-6080; Rubinstein et al. 2006. *Proc Natl Acad Sci USA* 103: 9166-9171).

Given the known effects of IL-15 on the immune system, a number of IL-15-based approaches have been explored to manipulate the immune system for the hosts benefit. While IL-15 administration has been employed to bolster immune responses or augment immune system reconstitution, blockade of IL-15 activity can inhibit autoimmune and other undesirable immune responses (Waldmann, T A, 2006, *Nature Rev. Immunol.* 6:595-601). In fact, one of the limitations with systemic IL-15 treatment is the possible induction of autoimmune disease. Other limitations include the difficulty in produce this cytokine in standard mammalian cell expression systems as well as its very short half-life in vivo. Therefore, there is a need to generate a suitable immunostimulatory therapeutic form of IL-15 that displays a longer in vivo half-life, increased activity binding to immune cells, or enhanced bioactivity. Additionally there is a need for effective IL-15 antagonists. Ideally it would be desirable that such molecules be selectively targeted to the disease site to avoid unwanted systemic toxicities and provide a more effective therapeutic benefit.

SUMMARY OF THE INVENTION

The instant invention provides a number of IL-15 variants and soluble fusion complexes that have therapeutic use and methods for making such proteins. The instant invention provides methods for killing target cells using the soluble fusion complexes of the invention. The IL-15 variants and soluble complexes described herein have potential therapeutic utility.

Accordingly, in one aspect, the invention provides a soluble fusion protein complex comprising at least two soluble fusion proteins, wherein the first fusion protein comprises a first biologically active polypeptide covalently linked to interleukin-15 (IL-15) or functional fragment thereof, and the second fusion protein comprises a second biologically active polypeptide covalently linked to soluble interleukin-15 receptor alpha (IL-15Ra) polypeptide or functional fragment thereof, wherein IL-15 domain of a first fusion protein binds to the soluble IL-15Ra domain of the second fusion protein to form a soluble fusion protein complex.

In one embodiment, one of the first and second biologically active polypeptides comprises a first soluble T-cell receptor (TCR) or functional fragment thereof. In another embodiment, an other of the biologically active polypeptides comprises the first soluble TCR or functional fragment thereof, thereby creating a multivalent TCR fusion protein complex with increased binding activity. In a further embodiment, the other biologically active polypeptide comprises a second soluble TCR or functional fragment thereof, different than the first soluble TCR.

In another embodiment of the aspect, the TCR is specific for recognition of a particular antigen.

In a further embodiment of the aspect, the TCR is a heterodimer comprising a and b chain TCR.

In still another embodiment of the aspect, the TCR comprises a single chain TCR polypeptide. In a further embodiment, the single chain TCR comprises a TCR V-α chain covalently linked to a TCR V-β chain by a peptide linker sequence. In another further embodiment, the single chain TCR further comprises a soluble TCR Cβ chain fragment covalently linked to a TCR V-β chain.

In another embodiment, the single chain TCR further comprises a soluble TCR Ca chain fragment covalently linked to a TCR V-α chain.

In a further embodiment, one or both of the first and second biologically active polypeptides comprises an antibody or functional fragment thereof.

In still another embodiment, the antibody is specific for recognition of a particular antigen. In a further embodiment, the antibody is a single-chain antibody or single-chain Fv. In another particular embodiment, the single-chain antibody comprises an immunoglobulin light chain variable domain covalently linked to immunoglobulin heavy chain variable domain by polypeptide linker sequence.

In one embodiment of the above described aspects, the first biologically active polypeptide is covalently linked to IL-15 (or functional fragment thereof) by polypeptide linker sequence.

In another embodiment of the above described aspects, the second biologically active polypeptide is covalently linked to IL-15Ra polypeptide (or functional fragment thereof) by polypeptide linker sequence.

In another embodiment, the antigen for the TCR domain comprises peptide antigen presented in an MHC or HLA molecule. In a further embodiment, the peptide antigen is derived from a tumor associated polypeptide or virus encoded polypeptide.

In another embodiment, the antigen for the antibody domain comprises a cell surface receptor or ligand.

In a further embodiment, the antigen comprises a CD antigen, cytokine or chemokine receptor or ligand, growth factor receptor or ligand, tissue factor, cell adhesion molecule, WIC/WIC-like molecules, FC receptor, Toll-like receptor, NK receptor, TCR, BCR, positive/negative co-stimulatory receptor or ligand, death receptor or ligand, tumor associated antigen, or virus encoded antigen.

In another embodiment of the above described aspects, the IL-15Ra polypeptide comprises the extracellular domain of the IL-15 receptor alpha capable for binding IL-15. In another embodiment of the above described aspects, the IL-15Ra polypeptide comprise either the IL-15a sushi domain (Wei et al. *Journal of Immunology*, 2001, 167: 277-282) or the IL-15aΔF3 domain (Anderson et al. 1995. *J. Biol. Chem.* 270:29862-29869, Dubois et al. 1999. *J. Biol. Chem.* 274:26978-26984).

In another aspect, the invention provides for an IL-15 variant (also referred to herein as IL-15 mutant) that has a different amino acid sequence that the native (or wild type) IL-15 protein and that binds the IL-15Ra polypeptide and functions as an IL-15 agonist or antagonist. Embodiments of the invention provide an IL-15 variant as a non-fusion protein or as a soluble fusion protein comprising a biologically active polypeptide described above, wherein the IL-15 variant is used in place of the IL-15 domain.

In one embodiment of the above described aspects, the invention features a nucleic acid sequence encoding the first fusion protein of any of the aspects or embodiments as described herein.

In one embodiment of the above described aspects, the invention features a nucleic acid sequence encoding the second fusion protein of any of the aspects or embodiments as described herein.

In one embodiment of the above described aspects, the invention features a nucleic acid sequence encoding the IL-15 variant of any of the aspects or embodiments as described herein.

In a one embodiment, the nucleic acid sequence further comprises a promoter, translation initiation signal, and leader sequence operably linked to the sequence encoding the fusion protein or IL-15 variant. In another embodiment, any of the nucleic acid sequences as described above are contained in a DNA vector.

In another aspect, the invention features a method for making a soluble fusion protein complex of the above-described aspects, the method comprising introducing into a first host cell a DNA vector of the above-described aspects and embodiments that encodes the first fusion protein, culturing the first host cell in media under conditions sufficient to express the first fusion protein in the cell or the media, purifying the first fusion protein from the host cells or media, introducing into a second host cell a DNA vector of the above-described aspects and embodiments encoding the second fusion protein, culturing the second host cell in media under conditions sufficient to express the second fusion protein in the cell or the media, and purifying the second fusion protein from the host cells or media, and mixing the first and second fusion protein under conditions sufficient to allow binding between IL-15 domain of a first fusion protein and the soluble IL-15Ra domain of a second fusion protein to form the soluble fusion protein complex.

In another aspect, the invention features a method for making a soluble fusion protein complex of the above-described aspects, the method comprising introducing into a host cell a DNA vector of the above-described aspects and embodiments, encoding the first fusion protein and a DNA vector as described in the above-described aspects and embodiments, encoding the second fusion protein, culturing the host cell in media under conditions sufficient to express the fusion proteins in the cell or the media and allow association between IL-15 domain of a first fusion protein and the soluble IL-15Ra domain of a second fusion protein to form the soluble fusion protein complex, purifying the soluble fusion protein complex from the host cells or media.

In still another aspect, the invention features a method for making a soluble fusion protein complex of the above-described aspects, the method comprising introducing into a host cell a DNA vector encoding the first and second fusion proteins, culturing the host cell in media under conditions sufficient to express the fusion proteins in the cell or the media and allow association between IL-15 domain of a first fusion protein and the soluble IL-15Ra domain of a second fusion protein to form the soluble fusion protein complex, purifying the soluble fusion protein complex from the host cells or media.

In still other aspects of the above described methods, the DNA vector encoding the IL-15 variant is used in place of the DNA vector encoding the first fusion protein to generate a host cell capable of expressing the IL-15 variant and the IL-15 variant is allowed associate with the IL-15Ra domain of a second fusion protein to form a soluble fusion protein complex.

In another aspect, the invention features a method for making an IL-15 variant of the above-described aspects, the method comprising introducing into a host cell a DNA vector of the above-described aspects and embodiments that encodes an IL-15 variant, culturing the host cell in media under conditions sufficient to express the IL-15 variant in the cell or the media, purifying the an IL-15 variant from the host cells or media.

In another aspect, the invention features a method for killing a target cell, the method comprising contacting a plurality of cells with a soluble fusion protein complex or IL-15 variant of any of the above-described aspects or embodiments, wherein the plurality of cells further comprises immune cells bearing the IL-15R chains recognized by the IL-15 domain of the above-described aspects and the target cells bearing an antigen recognized by at least one of the biologically active polypeptides of the above-described aspects, forming a specific binding complex (bridge) between the antigen on the target cells and the IL-15R chains on the immune cells sufficient to bind and activate the immune cells, and killing the target cells by the bound activated immune cells.

In one embodiment of the method, the target cells are tumor cells or virally infected cells.

In another embodiment of the method, the biologically active polypeptide comprises a TCR.

In still another embodiment of the method, the antigen on the target cells comprises a tumor or virally encoded peptide antigen presented in an MEW or HLA molecule and recognized by the TCR.

In a further embodiment of the method, the immune cells are T-cells, LAK cells or NK cells.

In another aspect, the invention features a method for preventing or treating disease in a patient in which the diseased cells express a disease associated antigen, the method comprising administering to the patient a soluble fusion protein complex or IL-15 variant of any of the above-described aspects or embodiments, comprising a biologically active polypeptide recognizing a disease-associated antigen forming a specific binding complex (bridge) between antigen-expressing diseased cells and IL-15R-expressing immune cells sufficient to localize the immune cells, and damaging or killing the disease cells sufficient to prevent or treat the disease in the patient.

In one aspect, the invention features a method for preventing or treating disease in a patient in which the diseased cells express a disease associated antigen, the method comprising mixing immune cells bearing the IL-15R chains with a soluble fusion protein complex comprising a biologically active polypeptide recognizing a disease-associated antigen, administering to the patient the immune cell-fusion protein complex mixture, forming a specific binding complex (bridge) between antigen-expressing diseased cells and IL-15R-expressing immune cells sufficient to localize the immune cells; and damaging or killing the disease cells sufficient to prevent or treat the disease in the patient.

In another aspect, the invention features a method for preventing or treating an disease in a patient in which the patient's cells express a disease associated antigen, the method comprising administering to the patient a soluble fusion protein complex or IL-15 variant of any of the above-described aspects or embodiments, comprising a biologically active polypeptide recognizing a disease-associated antigen on the patient's cells, localizing soluble fusion protein complex or IL-15 variant on the patient's cells wherein the IL-15 domain of the soluble fusion protein complex or IL-15 variant binds immune cells bearing the IL-15R chains and suppressing the immune response of the immune cells.

In one embodiment of the method, the disease is cancer or viral infection.

In another embodiment of the method, the disease is an immune disorder, autoimmune disease or inflammatory disorder.

In another embodiment of the method, the disease associated antigen is a peptide/WIC complex.

In another embodiment, the invention features a method of stimulating immune responses in a mammal comprising administering to the mammal an effective amount of the soluble fusion protein complex or IL-15 variant of any of the above-described aspects and embodiments.

In another embodiment, the invention features a method of suppressing immune responses in a mammal comprising administering to the mammal an effective amount of the soluble fusion protein complex or IL-15 variant of any of the above-described aspects and embodiments.

DESCRIPTION OF THE DRAWINGS

FIG. 1A and FIG. 1B are schematic drawings. FIG. 1A is a schematic depicting an example of a fusion protein complex containing single chain TCR polypeptides. FIG. 1B is a schematic depicting representative fusion protein constructs comprising the fusion protein complex_(SEQ ID NO: 3).

FIG. 2A, FIG. 2B, and FIG. 2C consist of three panels. FIG. 2A depicts a map of pNEF38-c264scTCR/huIL15 expression vector. FIG. 2B shows the sequence of c264scTCR/huIL15 fusion gene (SEQ ID NO: 4) and FIG. 2C shows the sequence of c264scTCR/huIL15 fusion protein (SEQ ID NO: 5), including the leader sequence.

FIG. 3A, FIG. 3B, and FIG. 3C consist of three panels. FIG. 3A depicts a map of pNEF38-c264scTCR-hinge-huIL15 expression vector. FIG. 3B shows the sequence of c264scTCR-hinge-huIL15 fusion gene (SEQ ID NO: 6) and FIG. 3C shows the sequence of c264scTCR-hinge-huIL15 fusion protein (SEQ ID NO: 7), including the leader sequence.

FIG. 4A, FIG. 4B, and FIG. 4C consist of three panels. FIG. 4A depicts a map of pNEF38-c264scTCR/huIL15RαΔE3 expression vector. FIG. 4B shows the sequence of c264scTCR/huIL15RαΔE3 fusion gene (SEQ ID NO: 8) and FIG. 4C shows the sequence of c264scTCR/huIL15RαΔE3 fusion protein (SEQ ID NO: 9), including the leader sequence.

FIG. 5A, FIG. 5B, and FIG. 5C consist of three panels. FIG. 5A depicts a map of the pNEF38-c264scTCR/huIL15RaSushi expression vector. FIG. 5B shows the sequence of c264scTCR/huIL15RαSushi fusion gene (SEQ ID NO: 10) and FIG. 5C shows the sequence of c264scTCR/huIL15RαSushi fusion protein (SEQ ID NO: 11), including the leader sequence.

FIG. 6A, FIG. 6B, and FIG. 6C consist of three panels. FIG. 6A depicts the pNEF38-c264scTCR-hinge-huIL15RaSushi expression vector. FIG. 6B shows the sequence of c264scTCR-hinge-huIL15RαSushi fusion gene_(SEQ ID NO: 12) and FIG. 6C shows the sequence of c264scTCR-hinge-huIL15RαSushi fusion protein (SEQ ID NO: 13), including the leader sequence.

FIG. 9A is two graphs showing flow cytometric analysis of fusion protein expressing cells. FIG. 9B is a graph showing TCR-based ELISA results for fusion protein production.

FIG. 10A shows cell culture supernatants containing c264scTCR/huIL15 or c264scTCR/huIL15RaSushi. FIG. 10B shows cell culture supernatants containing c264scTCR/huIL15 or c264scTCR/huIL15RαΔF3.

FIG. 11A is a graph showing the SEC chromatography profile of c264scTCR/huIL15. FIG. 11B is a graph showing the SEC chromatography profile of c264scTCR/huIL15RαSushi. FIG. 11C is a graph showing the SEC chromatography profile of c264scTCR/huIL15+c264scTCR/huIL15RαSushi fusion protein complex.

FIG. 12A is a graph illustrating the SEC chromatography profile of c264scTCR/huIL15RαΔE3. FIG. 12B is a graph illustrating the SEC chromatography profile of c264scTCR/huIL15+c264scTCR/huIL15RαΔE3 fusion protein complex.

FIG. 14A, FIG. 14B, FIG. 14C, and FIG. 14D, FIG. 14E, and FIG. 14F, and FIG. 14G consist of four panels. FIG. 14A shows the sequence of mature human IL15 protein (SEQ ID NO:1) and the blue underlined residues are substituted in the IL-15 variants as showed in Table 1. FIG. 14B and FIG. 14C depict the pNEF38-c264scTCR-hinge-huIL15D8A and pNEF38-c264scTCR-hinge-huIL15D8N expression vectors. FIG. 14D and FIG. 14E show the sequence of pNEF38-c264scTCR-hinge-huIL15D8A (SEQ ID NO: 14) and pNEF38-c264scTCR-hinge-huIL15D8N (SEQ ID NO: 15) genes and FIG. 14F and FIG. 14G show the sequence of pNEF38-c264scTCR-hinge-huIL15D8A (SEQ ID NO: 16) and pNEF38-c264scTCR-hinge-huIL15D8N fusion protein (SEQ ID NO: 17), including the leader sequence. The blue underlined nucleotides were changed to generate the indicated IL-15 variants.

FIG. 17A is a graph showing the binding of the dimeric complexes of TCR/IL15RαSushi and TCR/IL15 wt (native form), or TCR/IL15D8N or TCR/IL15D8A variants to cognate peptide/MHC complexes displayed on cells. FIG. 17B is a graph showing the slight background binding of dimeric complexes of TCR/IL15RαSushi and TCR/IL15 wt (native form) to the cells without loaded peptide. No background binding of dimeric complexes of TCR/IL15RαSushi and TCR/IL15D8N or TCR/IL15D8A variants was seen to the cells with not loaded. FIG. 17C is graph (showing flow cytometric analysis of IL-15RβγC-bearing 32Dβ cells stained with dimeric complexes of TCR/IL15RαSushi and TCR/IL15 wt (native form), or TCR/IL15N72D, TCR/IL15D8N or TCR/IL15D8A variants. Enhanced IL-15RβγC binding of the complex containing TCR/IL15N72D and decreased IL-15RβγC binding of complexes containing TCR/IL15D8N or TCR/IL15D8A was observed.

FIG. 18A is analysis showing binding activity of fusion proteins to cognate peptide/MHC complexes. FIG. 18B is analysis showing binding activity of fusion proteins to IL15Rα.

FIG. 19A, FIG. 19B, and FIG. 19C are graphs showing the ability of TCR/IL-15 fusion proteins comprising IL-15 variants to inhibit or enhance growth of IL15R-bearing cells, as determined by cell proliferation assay. FIG. 19A is graph showing the activity of fusion proteins comprising IL-15 variants to inhibit the proliferation of high affinity IL15R (αβγ receptor complex) bearing CTLL-2 cells. FIG. 19B is graph showing the activity of fusion proteins comprising IL-15 variants to inhibit or enhance the proliferation of low affinity IL15R (βγ receptor complex) bearing 32D13 cells. FIG. 19C is graph showing the activity of fusion proteins comprising IL-15 variants to block TCR/IL15 wt-stimulated proliferation of high affinity IL15R (αβγ receptor complex) bearing CTLL-2 cells.

FIG. 20 depicts the effects of in vitro incubation of NK cells with dimeric fusion proteins complexes of TCR/IL15RαSushi and TCR/IL15 on the survival of xenograft tumor-bearing nude mice. Athymic nude mice were injected with human NSCLC A549-A2 cells to allow establishment of lung metastases. Purified NK cells isolated from spleens of allogenic donor mice were incubated in vitro with rhIL-2, MART1scTCR-IL2, c264scTCR-IL2 or c264scTCR-IL15/c264scTCR-IL15Rα and adoptively transferred into the tumor-bearing mice that had been pretreated with cyclophosphamide (CTX), as indicated in the figure legend. The percent survival following treatment was plotted.

FIG. 21 sets forth Table 1 showing the amino acid replacements in the IL-15 variants and the affects of these changes on IL-15 activity.

FIGS. 22A-FIG. 22B set forth the amino acid sequence of IL-15 (SEQ ID NO:1) and the nucleic acid sequence of IL-15 (SEQ ID NO:2), respectively.

DETAILED DESCRIPTION OF THE INVENTION

Figure 2A:
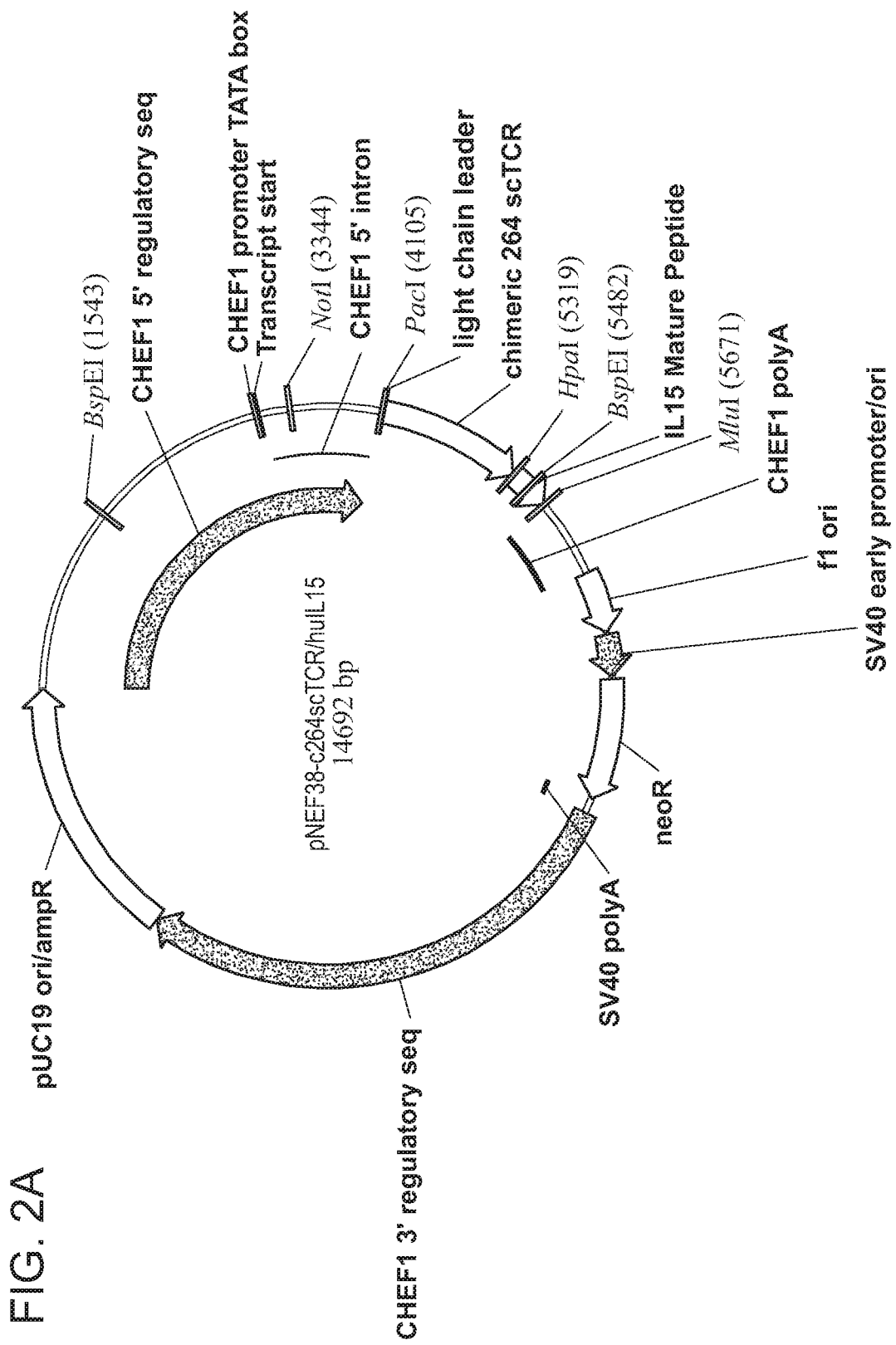

It has been established that the IL-15 stably binds to the extracellular domain of the IL-15Rα and that the resulting complex is capable of modulating (i.e. either stimulating or blocking) immune responses via the intermediate or high affinity IL-15R complex (Mortier, E. et al., 2006, *J. Biol. Chem.*, 281: 1612-1619; Stoklasek, T. et al., 2006, *J Immunol* 177: 6072-6080; Rubinstein, M. P. et al., 2006, *Proc Natl Acad Sci USA* 103: 9166-9171, Waldmann, T. A., 2006, *Nat Rev Immunol* 6: 595-601). In addition, it has been demonstrated that single-chain TCR or antibody polypeptides can be fused to cytokines and other immune effector domains and that such bispecific fusion molecules retain functional activity of both fusion domains (Belmont, H. J. et al., 2006, *Clin Immunol* 121: 29-39; Card, K. F. et al., 2004, *Cancer Immunol Immunother* 53: 345-357; Mosquera, L. A. et al., 2005, *J Immunol* 174: 4381-4388; Penichet, M. L., 1997, *Hum Antibodies* 8: 106-118). Further, it has been shown that multivalent forms of the TCR provide enhanced binding to their ligands (Zhu, X., H. J., 2006, *J Immunol* 176: 3223-3232).

Definitions

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

An "antibody" is any immunoglobulin, including antibodies and fragments thereof, that binds a specific epitope. The term encompasses polyclonal, monoclonal, chimeric and single-chain antibodies as well as bispecific antibodies.

The term "antigen" as used herein is meant any substance that causes the immune system to produce antibodies or specific cell-mediated immune responses against it. A disease associated antigen is any substance that is associated with any disease.

The term "biologically active polypeptide" as used herein is meant to refer to an amino acid sequence such as a protein, polypeptide or peptide; a sugar or polysaccharide; a lipid or a glycolipid, glycoprotein, or lipoprotein that can produce the desired effects as discussed herein, including a TCR or antibody fusion protein complex with antigen binding activity.

The term "cell" as used herein is meant to include any prokaryotic, eukaryotic, primary cell or immortalized cell line, any group of such cells as in, a tissue or an organ. Preferably the cells are of mammalian and particularly of human origin, and can be infected by one or more pathogens. A "host cell" in accord with the invention can be a transfected, transformed, transduced or infected cell of any origin, including prokaryotic, eukaryotic, mammalian, avian, insect, plant or bacteria cells, or it can be a cell of any origin that can be used to propagate a nucleic acid described herein.

The term "conjugate molecule" as it is used herein is meant to refer to a TCR or antibody molecule and an effector molecule usually a chemical or synthesized molecule covalently linked (i.e. fused) by chemical or other suitable method. If desired, the conjugate molecule can be fused at one or several sites through a peptide linker sequence or a carrier molecule. Alternatively, the peptide linker or carrier may be used to assist in construction of the conjugate molecule. Specifically preferred conjugate molecules are conjugate toxins or detectable labels.

The term "effector molecule" as used herein is meant to refer to an amino acid sequence such as a protein, polypeptide or peptide; a sugar or polysaccharide; a lipid or a glycolipid, glycoprotein, lipoprotein or chemical agent that can produce the desired effects as discussed herein, including an IL-15 domain, IL-15 variant or IL-15 receptor such as IL-15Rα, IL-2Rβ or γC, or functional fragments thereof.

The terms "fusion molecule" and "fusion protein" are used interchangeably and are meant to refer to a biologically active polypeptide usually a TCR or antibody and an effector molecule usually a protein or peptide sequence covalently linked (i.e. fused) by recombinant, chemical or other suitable method. If desired, the fusion molecule can be fused at one or several sites through a peptide linker sequence. Alternatively, the peptide linker may be used to assist in construction of the fusion molecule. Specifically preferred fusion molecules are fusion proteins. Generally fusion molecule also can be comprised of conjugate molecules.

The term "host cell" is meant to refer to any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

The term "immune response" as used herein is meant to refer to the process whereby immune cells are stimulated and recruited from the blood to lymphoid as well as non-lymphoid tissues via a multifactorial process that involves distinct adhesive and activation steps. Activation conditions cause the release of cytokines, growth factors, chemokines and other factors, upregulate expression of adhesion and other activation molecules on the immune cells, promote adhesion, morphological changes, and/or extravasation concurrent with chemotaxis through the tissues, increase cell proliferation and cytotoxic activity, stimulate antigen presentation and provide other phenotypic changes including generation of memory cell types. Immune response if also meant to refer to the activity of immune cells to suppress or regulate inflammatory or cytotoxic activity of other immune cells.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

The term "polypeptide" is meant to refer to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides useful in accordance with the present invention in general will be generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis.

The terms "prevent," "preventing," "prevention," "prophylactic treatment" and the like are meant to refer to reducing the probability of developing a disorder or condition in a subject, who does not have, but is at risk of or susceptible to developing a disorder or condition.

The term "single chain antibody" is meant to refer to an antibody based on a single chain format. Single chain antibodies can consist of the minimal binding subunit of antibodies. Single-chain antibodies can combine only those antigen-binding regions of antibodies on a single stably-folded polypeptide chain. As such, single-chain antibodies are of considerably smaller size than classical immuno-globulins but retain the antigen-specific binding properties of antibodies. Single chain antibodies may be linked to a wide range of ligands, for example effector molecules or drug conjugates.

The term "soluble" as used herein is meant that the fusion molecule and particularly a fusion protein that is not readily sedimented under low G-force centrifugation (e.g. less than about 30,000 revolutions per minute in a standard centrifuge) from an aqueous buffer, e.g., cell media. Further, the fusion molecule is soluble if it remains in aqueous solution at a temperature greater than about 5-37° C. and at or near neutral pH in the presence of low or no concentration of an anionic or non-ionic detergent. Under these conditions, a soluble protein will often have a low sedimentation value e.g., less than about 10 to 50 svedberg units.

Aqueous solutions referenced herein typically have a buffering compound to establish pH, typically within a pH range of about 5-9, and an ionic strength range between about 2 mM and 500 mM. Sometimes a protease inhibitor or mild non-ionic detergent is added. Additionally, a carrier protein may be added if desired such as bovine serum albumin (BSA) to a few mg/ml. Exemplary aqueous buffers include standard phosphate buffered saline, tris-buffered saline, or other well known buffers and cell media formulations.

The term "stimulate" or "stimulating" is meant to refer to increase, to amplify, to augment, to boost an immune response. Stimulation can be a positive alteration. An exemplary increase can be e.g., by 5%, 10%, 25%, 50%, 75%, or even 90-100%. Other exemplary increases include 2-fold, 5-fold, 10-fold, 20-fold, 40-fold, or even 100-fold.

The term "suppress" or "suppressing" is meant to refer to decrease, to attenuate, to diminish, to arrest, or to stabilize an immune response. Suppression may be a negative alteration. An exemplary decrease can be e.g., by 5%, 10%, 25%, 50%, 75%, or even 90-100%. Exemplary decreases include 2-fold, 5-fold, 10-fold, 20-fold, 40-fold, or even 100-fold.

The term "T-cell Receptor" (TCR) is meant to refer to polypeptides of a complex of integral membrane proteins that participates in the activation of T cells in response to the presentation of antigen. T cells recognize a peptide bound to the MHC product through the $\alpha\beta$. heterodimeric T cell receptor (TCR). The TCR repertoire has extensive diversity created by the same gene rearrangement mechanisms used in antibody heavy and light chain genes [Tonegawa, S. (1988) *Biosci. Rep.* 8:3-26]. Most of the diversity is generated at the junctions of variable (V) and joining (J) (or diversity, D) regions that encode the complementarity determining region 3 (CDR3) of the $\alpha$ and $\beta$ chains [Davis and Bjorkman (1988) *Nature* 334:395-402]. However, TCRs do not undergo somatic point mutations as do antibodies and, perhaps not coincidentally. TCRs also do not undergo the same extent of affinity maturation as antibodies. TCRs as they occur in nature appear to have affinities that range from $10^5$ to $10^7$ $M^{-1}$ whereas antibodies typically have affinities that range from $10^5$ to $109M^{-1}$ [Davis et al. (1998) *Annu. Rev. Immunol.* 16:523-544; Eisen et al. (1996) *Adv. Protein Chem.* 49:1-56]. While the absence of somatic mutation in TCRs may be associated with lower affinities, it has also been argued that there is not a selective advantage for a TCR to have higher affinity. In fact, the serial-triggering [Valitutti et al. (1995) *Nature* 375:148-151] and kinetic proofreading [Rabinowitz et al. (1996) *Proc. Natl. Acad. Sci. USA* 93:1401-1405] models of T cell activation both suggest that longer off-rates (associated with higher affinity) would be detrimental to the signaling process. It is also possible that higher affinity TCRs might not maintain the peptide specificity required for T cell responses. For example, peptides bound within the MHC groove display limited accessible surface [Bjorkman, P. J. (1997) Cell 89:167-170], which may in turn limit the amount of energy that can be generated in the interaction. On the other hand, raising the affinity of a TCR by directing the energy toward the MHC helices would presumably lead to thymic deletion during negative selection [Bevan, M. J. (1997) Immunity 7:175-178]. The term "TCR" encompasses polyclonal, monoclonal, chimeric, humanized, heterodimeric and single-chain T-cell receptors or functional fragment thereof, including molecule comprising the TCR Vα and Vβ domains. The term "TCR" also encompasses T-cell receptors disclosed in for example, US Provisional Application Entitled "T CELL RECEPTOR FUSIONS AND CONJUGATES AND METHODS OF USE THEREOF", filed Mar. 19, 2008 and US Patent Publication US 2003 01-44474A1.

The term "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

T-Cell Receptors (TCR)

T-cells are a subgroup of cells which together with other immune cell types (polymorphonuclear, eosinophils, basophils, mast cells, B-, NK cells), constitute the cellular component of the immune system. Under physiological conditions T-cells function in immune surveillance and in the elimination of foreign antigen. However, under pathological conditions there is compelling evidence that T-cells play a major role in the causation and propagation of disease. In these disorders, breakdown of T-cell immunological tolerance, either central or peripheral is a fundamental process in the causation of autoimmune disease.

The TCR is composed of at least seven transmembrane proteins. The disulfide-linked (4) heterodimer forms the monotypic antigen recognition unit, while the invariant chains of CD3, consisting of epsilon, gamma, delta, and zeta and eta chains, are responsible for coupling the ligand binding to signaling pathways that result in T-cell activation and the elaboration of the cellular immune responses. Despite the gene diversity of the TCR chains, two structural features are common to all known subunits. Firstly, they are transmembrane proteins with a single transmembrane spanning domain—presumably alpha-helical. Secondly, all the TCR chains have the unusual feature of possessing a charged amino acid within the predicted transmembrane domain. The invariant chains have a single negative charge, conserved between the mouse and human, and the variant chains possess one (TCR-beta) or two (TCR-alpha) positive charges. The transmembrane sequence of TCR-α is highly conserved in a number of species and thus phylogenetically may serve an important functional role. The octapeptide sequence containing the hydrophilic amino acids arginine and lysine is identical between the species.

A T-cell response is modulated by antigen binding to a TCR. One type of TCR is a membrane bound heterodimer consisting of an a and R chain resembling an immunoglobin variable (V) and constant (C) region. The TCR a chain includes a covalently linked V-α and C-α chain, whereas the R chain includes a V-β chain covalently linked to a C-β chain. The V-α and V-β chains form a pocket or cleft that can bind a superantigen or antigen in the context of a major histocompatibility complex (MHC) (known in humans as an HLA complex). See generally Davis Ann. Rev. of Immunology 3: 537 (1985); Fundamental Immunology 3rd Ed., W. Paul Ed. Rsen Press LTD. New York (1993).

Fusions Proteins

The soluble fusion protein and conjugate molecule complexes of the invention comprise at least two soluble fusion proteins, where the first fusion protein comprises a first biologically active polypeptide covalently linked to interleukin-15 (IL-15) or functional fragment thereof; and the second fusion protein comprises a second biologically active polypeptide covalently linked to soluble interleukin-15 receptor alpha (IL-15Ra) polypeptide or functional fragment thereof, and wherein IL-15 domain of a first fusion protein binds to the soluble IL-15Ra domain of the second fusion protein to form a soluble fusion protein complex.

In certain examples, one of the biologically active polypeptides comprises a first soluble TCR or fragment thereof. The other or second biologically active polypeptide comprises the first soluble TCR or functional fragment thereof and thus creates a multivalent TCR fusion protein complex with increased binding activity for cognate ligands compared to the monovalent TCR. Further, the other biologically active polypeptide comprises a second soluble TCR or functional fragment thereof, different than the first soluble TCR. In certain examples, TCRs are produced that have higher affinity, or increased binding affinity for cognate ligands as compared, for example, to the native TCR. If the soluble TCR of the invention as described herein has a higher avidity or affinity for its ligand, then it is useful as a specific probe for cell-surface bound antigen. In certain preferred examples of the invention, the TCR is specific for recognition of a particular antigen.

In exemplary embodiments, TCR is a heterodimer comprising an a chain (herein referred to as a, alpha or a chain) and a R chain (herein referred to as (3, beta or b chain). In other exemplary embodiments, the TCR comprises a single chain TCR polypeptide. The single chain TCR may comprise a TCR V-α chain covalently linked to a TCR V-β chain by a peptide linker sequence. The single chain TCR may further comprise a soluble TCR Cβ chain fragment covalently linked to a TCR V-β chain. The single chain TCR may further comprise a soluble TCR Ca chain fragment covalently linked to a TCR V-α chain.

In a further embodiment, one or both of the first and second biologically active polypeptides comprises an antibody or functional fragment thereof.

As used herein, the term "biologically active polypeptide" or "effector molecule" is meant an amino acid sequence such as a protein, polypeptide or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally-occurring or it can be synthesized from known components, e.g., by recombinant or chemical synthesis and can include heterologous components. A biologically active polypeptides or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electropheresis. Desired effects of the invention include, but are not limited to, for example, forming a TCR fusion protein complex with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same, and contacting the cells with a TCR fusion complex of the invention and then evaluating whether the TCR fusion complex inhibits further development of the cells.

Covalently linking the effector molecule to the TCR peptide in accordance with the invention provides a number of significant advantages. TCR fusion complexes of the invention can be produced that contain a single effector molecule, including such a peptide of known structure. Additionally, a wide variety of effector molecules can be produced in similar DNA vectors. That is, a library of different effector molecules can be linked to the TCR molecule for presentation of infected or diseased cells. Further, for therapeutic applications, rather than administration of an TCR molecule to a subject, a DNA expression vector coding for the TCR molecule linked to the effector peptide can be administered for in vivo expression of the TCR fusion complex. Such an approach avoids costly purification steps typically associated with preparation of recombinant proteins and avoids the complexities of antigen uptake and processing associated with conventional approaches.

As noted, components of the fusion proteins disclosed herein, e.g., effector molecule such as cytokines, chemokines, growth factors, protein toxins, immunoglobulin domains or other bioactive molecules and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein. More specific fusion proteins are in the Examples described below.

Linkers

The fusion complexes of the invention preferably also include a flexible linker sequence interposed between the IL-15 or IL-15Rα domains and the biologically active polypeptide. The linker sequence should allow effective positioning of the biologically active polypeptide with respect to the IL-15 or IL-15Rα domains to allow functional activity of both domains. In embodiments where the biologically active polypeptide is a TCR, the linker sequence positions the TCR molecule binding groove so that the T cell receptor can recognize presenting WIC-peptide complexes and can deliver the effector molecule to a desired site. Successful presentation of the effector molecule can modulate the activity of a cell either to induce or to inhibit T-cell proliferation, or to initiate or inhibit an immune response to a particular site, as determined by the assays disclosed below, including the in vitro assays that includes sequential steps of culturing T cells to proliferate same, and contacting the T cells with a TCR fusion complex of the invention and then evaluating whether the TCR fusion complex inhibits further development of the cells.

In certain embodiments, the soluble fusion protein complex has a linker wherein the first biologically active polypeptide is covalently linked to IL-15 (or functional fragment thereof) by polypeptide linker sequence.

In other certain embodiments, the soluble fusion protein complex as described herein has a linker wherein the second biologically active polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of the TCR molecule for recognition of a presenting antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. In certain embodiments, the IL-15 or IL-15Rα domains are effectively positioned to allow interactions with immune cells to initiate or inhibit an immune reaction, or to inhibit or stimulate cell development.

Preferably the linker sequence comprises from about 7 to 20 amino acids, more preferably from about 8 to 16 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker is preferably predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. For a fusion protein complex that comprise a heterodimer TCR, the linker sequence is suitably linked to the b chain of the TCR molecule, although the linker sequence also could be attached to the a chain of the TCR molecule. Alternatively, linker sequence may be linked to both a and b chains of the TCR molecule. When such a beta peptide chain is expressed along with the a chain, the linked TCR-effector peptide should fold resulting in a functional TCR molecule as generally depicted in FIG. 1. One suitable linker sequence is ASGGGGSGGG (i.e., Ala Ser Gly Gly Gly Gly Ser Gly Gly Gly) (SEQ ID NO: 18), preferably linked to the first amino acid of the b domain of the TCR. Different linker sequences could be used including any of a number of flexible linker designs that have been used successfully to join antibody variable regions together, see Whitlow, M. et al., (1991) *Methods: A Companion to Methods in Enzymology* 2:97-105. In some examples, for covalently linking an effector molecule to a TCR b chain molecule, the amino sequence of the linker should be capable of spanning suitable distance from the C-terminal residue of the TCR beta chain to the N-terminal residue of the effector molecule.

In general, preparation of the fusion protein complexes of the invention can be accomplished by procedures disclosed herein and by recognized recombinant DNA techniques involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, the fusion molecules can be isolated and purified using chaotropic agents and well known electrophoretic, centrifugation and chromatographic methods. See generally, Sambrook et al., *Molecular Cloning: A Laboratory Manual* (2nd ed. (1989); and Ausubel et al., *Current Protocols in Molecular Biology*, John Wiley & Sons, New York (1989) for disclosure relating to these methods.

As used herein, biologically active polypeptides or effector molecules of the invention may include factors such as cytokines, chemokines, growth factors, protein toxins, immunoglobulin domains or other bioactive proteins such as enzymes. Also biologically active polypeptides may include conjugates to other compounds such as non-protein toxins, cytotoxic agents, chemotherapeutic agents, detectable labels, radioactive materials and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-1, IL-17, TGF and TNF cytokine families, and to IL-1 through IL-35, IFN-α, IFN-β, IFN-γ, TGF-β, TNF-α and TNFβ.

In an aspect of the invention, the first fusion protein comprises a first biologically active polypeptide covalently linked to interleukin-15 (IL-15) domain or a functional fragment thereof. IL-15 is a cytokine which affects T-cell activation and proliferation. IL-15 activity in affecting immune cell activation and proliferation is similar in some respects to IL2, although fundamental difference have been well characterized (Waldmann, T A, 2006, *Nature Rev. Immunol.* 6:595-601).

In another aspect of the invention, the first fusion protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Ra polypeptide and functions as an IL-15 agonist or antagonist. Preferably IL-15 variants with agonist activity have super agonist activity. In some embodiments, the IL-15 variant can function as an IL-15 agonist or antagonist independent of its association with IL-15Ra. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some embodiments, the sequence of the IL-15 variant has at least one amino acid change, e.g. substitution or deletion, compared to the native IL-2 sequence, such changes resulting in IL-15 agonist or antagonist activity. Preferably the amino acid substitutions/deletions are in the domains of IL-15 that interact with IL-15Rβ and/or γC. More preferably, the amino acid substitutions/deletions do not affect binding to the IL-15Ra polypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally suitable amino acid substitutions can be conservative or non-conservative changes and insertions of additional amino acids Preferably IL-15 variants of the invention contain one or more than one amino acid substitutions/deletions at position 8, 61, 65, 72, 92, 101, 108, or 111 of the mature human IL-15 sequence; particularly, D8N ("D8" refers to the amino acid and residue position in the native mature human IL-15 sequence and "N" refers to the substituted amino acid residue at that position in the IL-15 variant), D8A, D61A, N65A, N72R or Q108A substitutions result in IL-15 variants with antagonist activity and N72D substitutions result in IL-15 variants with agonist activity.

While in one aspect of the invention the IL-15 variant is a component of a fusion protein complex, in other aspects the IL-15 variant is a non-fusion protein. Preferably the non-fusion form of the IL-15 variant is a soluble cytokine that functions as an IL-15 agonist or antagonist. In some embodiments, the non-fusion IL-15 variant forms a complex with IL-15Ra whereas in other embodiment it acts independently of IL-15Ra.

Chemokines of the invention, similar to cytokines, are defined as any chemical factor or molecule which when exposed to other cells are responsible for any of a number of multiple effects of cellular immunity. Suitable chemokines may include but are not limited to the CXC, CC, C, and $CX_3C$ chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance which has a lethal effect or an inhibitory effect on growth when exposed to cells. More specifically, the effector molecule can be a cell toxin of, e.g., plant or bacterial origin such as, e.g., diphtheria toxin (DT), shiga toxin, abrin, cholera toxin, ricin, saporin, pseudomonas exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; a phosphorescent or chemiluminescent molecules or a label detectable by PET, ultrasound or Mill such as Gd- or paramagnetic metal ion-based contrast agents. See e.g., Moskaug, et al. *J. Biol. Chem.* 264, 15709 (1989); Pastan, I. et al. Cell 47, 641, 1986; Pastan et al., *Recombinant Toxins as Novel Therapeutic Agents*, Ann. Rev. Biochem. 61, 331, (1992); "Chimeric Toxins" Olsnes and Phil, *Pharmac. Ther.*, 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

A protein fusion or conjugate complex that includes a covalently linked IL-15 and IL-15Ra domains has several important uses. For example, the protein fusion or conjugate complex comprising a TCR can be employed to deliver the IL-15/IL-15Ra complex \ to certain cells capable of specifically binding the TCR. Accordingly, the protein fusion or conjugate complex provide means of selectively damaging or killing cells comprising the ligand. Examples of cells or tissue capable of being damaged or killed by the protein fusion or conjugate complexes comprising a TCR include tumors and virally or bacterially infected cells expressing one or more ligands capable of being specifically bound by the TCR. Cells or tissue susceptible to being damaged or killed can be readily assayed by the methods disclosed herein.

The IL-15 and IL-15Ra polypeptides of the invention suitably correspond in amino acid sequence to naturally occurring IL-15 and IL-15Ra molecules, e.g. IL-15 and IL-15Ra molecules of a human, mouse or other rodent, or other mammal.

In some settings it can be useful to make the protein fusion or conjugate complexes of the present invention polyvalent, e.g., to increase the valency of the scTCR. In particular, interactions between the IL-15 and IL-15Ra domains of the fusion protein complex provide a means of generating polyvalent complexes. In addition, the polyvalent fusion protein can made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable dendrimer or other nanoparticle to give a multivalent molecule. Dendrimers are synthetic chemical polymers that can have any one of a number of different functional groups of their surface (D. Tomalia, *Aldrichimica Acta*, 26:91:101 (1993)). Exemplary dendrimers for use in accordance with the present invention include e.g. E9 starburst polyamine dendrimer and E9 combust polyamine dendrimer, which can link cystine residues.

Nucleic Acids and Vectors
Nucleic Acids

The invention further provides nucleic acid sequences and particularly DNA sequences that encode the present fusion proteins. Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See generally Sambrook et al., supra and Ausubel et al. supra.

Included in the invention are methods for making a soluble fusion protein complex, the method comprising introducing into a host cell a DNA vector as described herein encoding the first and second fusion proteins, culturing the host cell in media under conditions sufficient to express the fusion proteins in the cell or the media and allow association between IL-15 domain of a first fusion protein and the soluble IL-15Rα domain of a second fusion protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a TCR chain, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion complex is to be used against pathogens that may have or have capacity to develop serotypes.

To make the vector coding for a TCR fusion complex, the sequence coding for the TCR molecule is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the TCR molecule can be amplified by the polymerase chain reaction (PCR) or other means known in the art. Suitable PCR primers to amplify the TCR peptide gene may add restriction sites to the PCR product. The PCR product preferably includes splice sites for the effector peptide and leader sequences necessary for proper expression and secretion of the TCR-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the TCR protein is isolated, sequence can be ligated to another DNA molecule encoding the effector polypeptide. The nucleotide sequence coding for a TCR molecule may be directly joined to a DNA sequence coding for the effector peptide or, more typically, a DNA sequence coding for the linker sequence as discussed herein may be interposed between the sequence coding for the TCR molecule and the sequence coding for the effector peptide and joined using suitable ligases. The resultant hybrid DNA molecule can be expressed in a suitable host cell to produce the TCR fusion complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the TCR peptide fused to the effector peptide, or a leader sequence, which directs the TCR fusion complex to the cell surface or the culture medium, can be included in the construct or present in the expression vector into which the construct is inserted. An immunoglobulin or CMV promoter is particularly preferred.

In obtaining variant TCR coding sequences, those of ordinary skill in the art will recognize that TCR-derived proteins may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50.degree. C., 6.times.SSC (sodium chloride/sodium citrate buffer) and 0.1% SDS (sodium dodecyl sulfate) indicate about 60-70% homology, hybridization and wash conditions of 50-65.degree. C., 1.times.SSC and 0.1% SDS indicate about 82-97% homology, and hybridization and wash conditions of 52.degree. C., 0.1.times.SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2.ebi.ac.uk.

The components of the fusion protein can be organized in nearly any order provided each is capable of performing its intended function. For example, in one embodiment, the TCR is situated at the C or N terminal end of the effector molecule.

Preferred effector molecules of the invention will have sizes conducive to the function for which those domains are intended. The effector molecules of the invention can be made and fused to the TCR by a variety of methods including well-known chemical cross-linking methods. See e.g., Means, G. E. and Feeney, R. E. (1974) in Chemical Modification of Proteins, Holden-Day. See also, S. S. Wong (1991) in *Chemistry of Protein Conjugation and Cross-Linking*, CRC Press. However it is generally preferred to use recombinant manipulations to make the in-frame fusion protein.

As noted, a fusion molecule or a conjugate molecule in accord with the invention can be organized in several ways. In an exemplary configuration, the C-terminus of the TCR is operatively linked to the N-terminus of the effector molecule. That linkage can be achieved by recombinant methods if desired. However, in another configuration, the N-terminus of the TCR is linked to the C-terminus of the effector molecule.

Alternatively, or in addition, one or more additional effector molecules can be inserted into the TCR fusion or conjugate complexes as needed.

Vectors and Expression

A number of strategies can be employed to express protein fusion complexes of the invention. For example, the TCR gene fusion construct described above can be incorporated into a suitable vector by known means such as by use of restriction enzymes to make cuts in the vector for insertion of the construct followed by ligation. The vector containing the gene construct is then introduced into a suitable host for expression of the TCR fusion peptide. See, generally, Sambrook et al., supra. Selection of suitable vectors can be made empirically based on factors relating to the cloning protocol. For example, the vector should be compatible with, and have the proper replicon for the host that is being employed. Further the vector must be able to accommodate the DNA sequence coding for the TCR fusion complex that is to be expressed. Suitable host cells include eukaryotic and prokaryotic cells, preferably those cells that can be easily transformed and exhibit rapid growth in culture medium. Specifically preferred hosts cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See Sambrook, supra. Stable transformed or transfected cell lines can then be selected. Cells expressing a TCR fusion complex of the invention can be determined by known procedures. For example, expression of a TCR fusion complex linked to an immunoglobulin can be determined by an ELISA specific for the linked immunoglobulin and/or by immunoblotting. Other methods for detecting expression of fusion proteins comprising TCRs linked to IL-15 or IL-15Rα domains are disclosed in the Examples.

As mentioned generally above, a host cell can be used for preparative purposes to propagate nucleic acid encoding a desired fusion protein. Thus a host cell can include a prokaryotic or eukaryotic cell in which production of the fusion protein is specifically intended. Thus host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA*, 77:4216 (1980)), 293 cells (Graham et al., *J Gen. Virol.*, 36:59 (1977)) or myeloma cells like SP2 or NSO (Galfre and Milstein, *Meth. Enzymol.*, 73(B):3 (1981)).

Host cells capable of propagating nucleic acid encoding a desired fusion protein encompass non-mammalian eukaryotic cells as well, including insect (e.g., *Sp. frugiperda*), yeast (e.g., *S. cerevisiae, S. pombe, P. pastoris., K lactis, H. polymorpha*; as generally reviewed by Fleer, R., *Current*

*Opinion in Biotechnology*, 3(5):486496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the TCR coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* alpha-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His.sup.-*S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600.mu.g of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (.lambda.ZAP and pBLUE-SCRIPT SK-1, Stratagene, LaJolla, Calif., pET, Novagen Inc., Madison, Wis. —cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *S. cerevisiae* cells by protoplast transformation or electroporation. Electroporation of *S. cerevisiae* is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium in the presence of the fusion protein to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

An expressed protein fusion complex can be isolated and purified by known methods. Typically the culture medium is centrifuged and then the supernatant is purified by affinity or immunoaffinity chromatography, e.g. Protein-A or Protein-G affinity chromatography or an immunoaffinity protocol comprising use of monoclonal antibodies that bind the expressed fusion complex such as a linked TCR or immunoglobulin region thereof. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

Truncated TCR fusion complexes of the invention contain a TCR molecule that is sufficiently truncated so the TCR fusion complex can be secreted into culture medium after expression. Thus, a truncated TCR fusion complex will not include regions rich in hydrophobic residues, typically the transmembrane and cytoplasmic domains of the TCR molecule. Thus, for example, for a preferred truncated DR1 TCR molecule of the invention, preferably from about residues 199 to 237 of the b chain and from about residues 193 to 230 of the a chain of the TCR molecule are not included in the truncated TCR fusion complex.

The present TCR fusion and conjugate complexes are suitable for in vitro or in vivo use with a variety of cells that are infected or that may become infected by one or more diseases.

Methods

Therapeutic

Included in the invention are methods for preventing or treating disease in a patient in which the diseased cells express a disease associated antigen, the method comprising administering to the patient a soluble fusion protein complex comprising a biologically active polypeptide recognizing a disease-associated antigen, forming a specific binding complex (bridge) between antigen-expressing diseased cells and IL-15R-expressing immune cells sufficient to localize the immune cells, and damaging or killing the disease cells sufficient to prevent or treat the disease in the patient.

Included are methods for preventing or treating disease in a patient in which the diseased cells express a disease associated antigen, the method comprising mixing immune cells bearing the IL-15R chains with a soluble fusion protein complex comprising a biologically active polypeptide recognizing a disease-associated antigen, for example a peptide/WIC complex, administering to the patient the immune cell-fusion protein complex mixture, forming a specific binding complex (bridge) between antigen-expressing diseased cells and IL-15R-expressing immune cells sufficient to localize the immune cells, and damaging or killing the disease cells sufficient to prevent or treat the disease in the patient.

Also included in the invention are methods for killing a target cell, the method comprising contacting a plurality of cells with a soluble fusion protein complex, where the plurality of cells further comprises immune cells bearing the IL-15R chains recognized by the IL-15 domain and the target cells bearing an antigen recognized by at least one of the biologically active polypeptides as described herein, forming a specific binding complex (bridge) between the antigen on the target cells and the IL-15R chains on the immune cells sufficient to bind and activate the immune cells; and killing the target cells by the bound activated immune cells.

Also included in the inventions are methods to increase in vivo half life of IL-15 and/or enhance its ability to stability bind immune cells (e.g. increase cell surface residency time) through generation of a soluble fusion protein complex. For example, evaluation of the pharmacokinetic parameters and cell surface residency time of the fusion protein complex are conducted and compared to IL-15, as described herein. Fusion protein complexes with an increased serum half life or cell surface residency time are preferable as based on their improved therapeutic utility.

Examples of diseases that can be treated include, but are not limited to, neoplasia, including cancer, or viral infection. By "neoplasia" is meant any disease that is caused by or results in inappropriately high levels of cell division, inappropriately low levels of apoptosis, or both. For example, cancer is an example of a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

Also included are methods of stimulating immune responses in a mammal comprising administering to the mammal an effective amount of the soluble fusion protein complex or IL-15 variant as described herein. Also included are methods of suppressing immune responses in a mammal comprising administering to the mammal an effective amount of the soluble fusion protein complex or IL-15 variant as described herein. In the case of immune suppression, a fusion protein complex or IL-15 variant comprising IL-15 antagonists or IL-15 domains that lack the ability to bind the IL-15βγ$_c$ complex may be particularly advantageous.

As an illustration of the use of the fusion protein complex therapeutics, a cultured cell can be infected by a pathogen of a single serotype. The infected cell is then contacted by a specified fusion protein complex in vitro. As discussed previously, the fusion protein complex is configured so that the toxic domain is presented to the infected cell by the association of the TCR. After providing for introduction of the bioactive molecule to the cell (generally less than about 30 minutes), the cells are allowed to cause a desired effect for a time period of about up to about 2 to 24 hours, typically about 18 hours. After this time, the cells are washed in a suitable buffer or cell medium and then evaluated for viability. The time allotted for cell killing or injury by the fusion protein complex will vary with the particular effector molecule chosen. However viability can often be assessed after about 2 to 6 hours up to about 24 hours. As will be explained in more detail below, cell viability can be readily measured and quantified by monitoring uptake of certain well-known dyes (e.g., trypan blue) or fluors.

Cells incubated with the fusion protein complex of the present invention can be assayed for viability by standard methods. In one exemplary approach, cell viability can be readily assayed by measuring DNA replication following or during incubation. For example, a preferred assay involves cell uptake of one or more detectably labeled nucleosides such as radiolabelled thymidine. The uptake can be conveniently measured by several conventional approaches including trichloroacetic acid (TCA) precipitation followed by scintillation counting. Other cell viability methods include well-known trypan blue exclusion techniques or WST-1-based proliferation assays.

The TCR molecules of the fusion complexes of the invention suitably correspond in amino acid sequence to naturally occurring TCR molecules, e.g. TCR molecules of a human, mouse or other rodent, or other mammal.

Accordingly, one treatment method of the invention for inhibition of an autoimmune or inflammatory response would include a fusion protein complex which comprises a T cell receptor or antibody with binding specificity to a disease associated antigen. Preferably, a "truncated" soluble TCR complex is administered, i.e. the TCR complex does not contain a transmembrane portion. The fusion protein complex also comprises an IL-15 variants that functions as an IL-15 antagonist to suppress the unwanted immune response. Follow administration, the TCR or antibody domain targets the fusion protein complex to the disease site where the IL-15 antagonist suppresses the autoimmune or inflammatory response. Such fusion protein complex may particularly useful for treatment of allergies, autoimmune diseases such as multiple sclerosis, insulin-dependent diabetes mellitus and rheumatoid arthritis or transplant rejection. Similar non-targeted approaches could be carried out using antagonist IL-15 variants as non-fusion proteins.

Another treatment method of the invention for induction of an immune response provides for the administration of an effective amount of a protein fusion complexes of the invention in the presence of any costimulatory effector molecule such as a cytokine to thereby induce a desired immune response at the location of the presented antigen which binds the biologically active polypeptide.

Different therapies of the invention also may be used in combination as well as with other known therapeutic agents such as anti-inflammatory drugs to provide a more effective treatment of a disorder. For example, immunosuppressive protein fusion complexes or IL-15 variants can be used in combination with anti-inflammatory agents such as corticosteroids and nonsteroidal drugs for the treatment of autoimmune disorders and allergies.

Compounds of the invention will be especially useful to a human patient who has or is suspected of having a malignant disease, disorder or condition. Compounds of the invention will be particularly useful in targeting particular tumor antigens in human patients. Specific examples of diseases which may be treated in accordance with the invention include cancers, e.g. breast, prostate, etc, viral infections, e.g. HCV, HIV, etc. as well as other specific disorders of conditions mentioned herein.

Without wishing to be bound by theory, it is believed the multiple and distinct covalently linked compounds of this invention (i.e. at least IL-15 in combination with at least one TCR) can significantly enhance efficacy of the IL-15, e.g., by increasing targeting of IL-15 to target antigen in subject individuals.

Moreover, by virtue of the covalent linkage, the conjugates of the invention present the IL-15 and the TCR to the subject cell essentially simultaneously, an effect that may not be readily achieved by administering the same compounds in a drug "cocktail" formulation without covalently linking the compounds.

It also has been reported that treatment with treatment with one drug can in turn sensitize a patient to another drug. Accordingly, the essentially simultaneous presentation to the subject cell of IL-15 and TCR via a conjugate of the invention may enhance drug activity, e.g., by providing synergistic results and/or by enhancing production an immune response.

Diagnostic

High affinity or multivalent TCR proteins specific for a particular pMHC ligand are useful in diagnosing animals, including humans believed to be suffering from a disease associated with the particular pMHC. The fusion protein complexes of the present invention are useful for detecting essentially any antigen, including but not limited to, those associated with a neoplastic condition, an abnormal protein, an autoimmune disease or an infection or infestation with a bacterium, a fungus, a virus, a protozoan, a yeast, a nematode or other parasite.

In one such method for detecting a tumor or virally infected cell or tissue in a subject, wherein the cell or tissue comprises a tumor or virus-associated peptide antigen presented on the cells or tissue in the context of an MHC complex, comprises: a) administering to the subject a soluble fusion protein complex of the invention comprising a soluble TCR under conditions that form a specific binding complex between the presented peptide antigen and the TCR; and b) detecting the specific binding complex as being indicative of a tumor or virally infected cell or tissue comprising the presented tumor or viral-associated peptide antigen.

The fusion protein complexes can also be used in the diagnosis of certain genetic disorders in which there is an abnormal protein produced. Exemplary applications for fusion protein complexes are in the diagnosis and treatment of autoimmune diseases in which there is a known pMHC. Type I diabetes is relatively well characterized with respect to the autoantigens which attract immune destruction. Multiple sclerosis, celiac disease, inflammatory bowel disease, Crohn's disease and rheumatoid arthritis are additional candidate diseases for such application.

The fusion protein complexes of the present invention comprising IL-15 variant polypeptides may be particularly useful in these applications. For example, for a fusion protein complex comprising TCR molecules, interactions between the IL-15 variant domain and the IL-15Ra polypeptide generate multivalent TCR molecules with enhanced antigen binding activity, as disclosed herein. Moreover, the IL-15 variant contains amino acid changes that potentially eliminate binding to cells bearing IL-15Rβγ C receptors, thereby reducing non-specific or non-targeted binding to immune cells. As a results, improved detection of TCR-specific antigens can be achieved with such fusion protein complexes. Additionally fusion protein complexes of the invention can be further multimerized via peptide tags sequences or conjugation to detectable labels, as disclosed herein.

Dosage and Administration

Administration of compounds of the invention may be made by a variety of suitable routes including oral, topical (including transdermal, buccal or sublingual), nasal and parenteral (including intraperitoneal, subcutaneous, intravenous, intradermal or intramuscular injection) with oral or parenteral being generally preferred. It also will be appreciated that the preferred method of administration and dosage amount may vary with, for example, the condition and age of the recipient.

Compounds of the invention may be used in therapy alone or in conjunction with other medicaments such those with recognized pharmacological activity to treat the desired indications. Exemplary medicaments include recognized therapeutics such as surgery, radiation, chemotherapy and other forms of immunotherapy (e.g. vaccines, antibody based therapies). The compounds of this invention can be administered before, during or after such therapies as needed.

While one or more compounds of the invention may be administered alone, they also may be present as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Pharmaceutical compositions of the invention in general comprise one or more fusion protein complex or IL-15 variant of the invention or DNA constructs coding for such compounds together with one or more acceptable carriers. The carriers must be "acceptable" in the sense of being compatible with other ingredients of the formulation and not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Therapeutic compounds of the invention also may be incorporated into liposomes. The incorporation can be carried out according to known liposome preparation procedures, e.g. sonication and extrusion. Suitable conventional methods of liposome preparation are also disclosed in e.g. A. D. Bangham et al., *J. Mol. Biol.*, 23:238-252 (1965); F. Olson et al., *Biochim. Biophys. Acta*, 557:9-23 (1979); F. Szoka et al., *Proc. Nat. Acad. Sci.*, 75:4194-4198 (1978); S. Kim et al., *Biochim. Biophys. Acta*, 728:339-348 (1983); and Mayer et al., *Biochim. Biophys. Acta*, 858:161-168 (1986).

The invention also provides methods for invoking an immune response in a mammal such as a human, including vaccinating a mammal such as a human against an infectious agent or a targeted disorder such as cancer.

These methods comprise administering to a mammal an effective amount of a DNA sequence that comprises a DNA vector that codes for a fusion protein complex or IL-15 variant of the invention. Preparation of expression vectors of fusion protein complexes and IL-15 variants is described above and in the Examples which follow. Methods for administration of plasmid DNA, uptake of that DNA by cells of the administered subject and expression of protein has been reported. See Ulmer, J. B., et al., *Science* (1993) 259: 1745-1749.

DNA vectors that encode fusion protein complexes and IL-15 variants of the invention are suitably administered to a mammal including a human preferably by intramuscle injection. Administration of cDNA to skeletal muscle of a mammal with subsequent uptake of administered expression vector by the muscle cells and expression of protein encoded by the DNA has been described by Ulmer et al. and represents an exemplary protocol [Ulmer, J. B., et al., *Science* 259: 1745-1749]. The optimal dose for a given therapeutic application can be determined by conventional means.

In addition to treatment of human disorders, fusion protein complexes and IL-15 variants of the invention and DNA constructs of the invention that encode such molecules will have significant use for veterinary applications, e.g., treatment of disorders of livestock such as cattle, sheep, etc. and pets such as dog and cats.

It will be appreciated that actual preferred amounts of a given fusion protein complex and IL-15 variant of the invention or DNA construct coding for same used in a given therapy will vary according to the particular active compound or compounds being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests conducted e.g. with regard to the foregoing guidelines and the assays disclosed herein.

EXAMPLES

It should be appreciated that the invention should not be construed to be limited to the examples that are now described; rather, the invention should be construed to include any and all applications provided herein and all equivalent variations within the skill of the ordinary artisan.

Example 1—Design of a Fusion Protein Complex Comprising scTCR/huIL15 and scTCR/huIL15Rα Fusion Proteins It has been established that the IL-15 stably binds to the extracellular domain of the IL-15Rα and that the resulting complex is capable of modulating (i.e. either stimulating or blocking) immune responses via the intermediate or high affinity IL-15R complex (Mortier, E. et al., 2006, *J. Biol. Chem.*, 281: 1612-1619; Stoklasek, T. et al., 2006, *J Immunol* 177: 6072-6080; Rubinstein, M. P. et al., 2006, *Proc Natl Acad Sci USA* 103: 9166-9171, Waldmann, T. A., 2006, *Nat Rev Immunol* 6: 595-601). In addition, it has been demonstrated that single-chain TCR or antibody polypeptides can be fused to cytokines and other immune effector domains and that such bispecific fusion molecules retain functional activity of both fusion domains (Belmont, H. J. et al., 2006, *Clin Immunol* 121: 29-39; Card, K. F. et al., 2004, *Cancer Immunol Immunother* 53: 345-357; Mosquera, L. A. et al., 2005, *J Immunol* 174: 4381-4388; Penichet, M. L., 1997, *Hum Antibodies* 8: 106-118). Further, it has been shown that multivalent forms of the TCR provide enhanced binding to their ligands (Zhu, X., H. J., 2006, *J Immunol* 176: 3223-3232). Therefore a feature of the invention provides for a fusion protein complex comprising at least one fusion protein wherein a first TCR polypeptide is fused to IL-15 and at least one fusion wherein a second TCR polypeptide is fused to the extracellular domain of IL-15Rα, such that the two fusion proteins form a complex through binding interactions between the IL-15 and IL-15Rα domains. In such a fusion protein complex, the TCR polypeptides can be the same or different and in either single-chain or heterodimeric format.

An example of a fusion protein complex containing single-chain TCR polypeptides is shown schematically in FIG. 1A. In this fusion protein complex, the multivalent TCR domains provide increased binding avidity/affinity for their ligands. Exemplary ligands include, but are not limited to, peptide/MHC complexes. The IL-15/IL-15Rα domains provide immunomodulatory activity. Representative fusion protein constructs comprising the fusion protein complex are schematically shown in FIG. 1B. In these constructs the TCR polypeptide is a single-chain TCR (264scTCR) comprised of TCR-Vα and TCR-Vβ-Cβ domains linked by a peptide linker sequence ((G4S)4) (SEQ ID NO: 3). The scTCR polypeptide is fused to either the IL-15 or IL-15Rα domains, directly or via a peptide linker sequence. Proceeding the scTCR polypeptide is a signal peptide (or leader peptide) sequence that permits soluble expression. The signal peptide is subsequently cleaved during protein transport to generate the mature fusion protein. In other examples of the fusion protein complex, an antibody domain can substitute a TCR domain depicted in FIGS. 1A and 1B. Such an antibody can be in a single-chain or heteromultimeric format. For any of the fusion protein complexes described above, sequences can be human or non-human, for example, but not limited to mouse. These sequences can be employed for part or all of the fusion protein domains. In addition, the arrangement of the domains can vary so long as the fusion proteins remain soluble and functional.

Example 2—Construction of the c264scTCR/huIL15 Gene Fusion in an Expression Vector Isolation and characterization of TCR genes for the p53 (aa264-272)-specific TCR were described previously (Belmont, H. J. et al., 2006, *Clin Immunol* 121: 29-39; Card, K. F. et al., 2004, *Cancer Immunol Immunother* 53: 345-357; Mosquera, L. A. et al., 2005, *J Immunol* 174: 4381-4388). To obtain the human IL15 and IL15Rα genes, human PBMC were isolated from 200 mL of blood of a donor (Lot #2238789, Community Blood Bank, Miami, FL) with HIS-TOPAGUE-1077 (Sigma). The cells ($1.5 \times 10^7$) were activated by 30 ng/ml of PMA (Sigma), 200 ng/ml of ionomycin, and 220 ng/ml of recombinant human IL2 in IMDM containing 10% FBS in a $CO_2$ incubator for 10 days. The activated cells ($1 \times 10^7$ per mL) were frozen at −70 C for the further applications. To purify the total RNA from the activated PBMC, RNEASY PLUS MINI (Qiagen) was used according to the manufacturer's protocol. Human IL15 gene containing the coding region and a portion of 5' and 3' flanking regions was amplified from the total RNA with the front primer (SEQ ID NO: 19)
5'-CACCTTGCCATAGCCAGCTCTTC-3' and the back primer (SEQ ID NO: 20)
5'-GTCTAAGCAGCAGAGTGATGTTTG-3' by SUPERSCRIPT III One-Step RT-PCR Platinum Taq HiFi (Invitrogen) according to the following conditions: for RT; 55 C 30 min; 94 C, 2 min; for amplifying cDNA; 94 C, 30 s; 53 C, 30 s; 68 C, 1 min; ×40 cycles; 68 C, 5 min. The 600 bp human IL15 PCR-cDNA product was separated by electrophoresis on a 1% agarose gel and isolated. The cDNA product was purified from agarose with a Qiaquick Gel Extraction Kit (Qiagen). The gene of the mature human IL15 protein was amplified from the 600 bp human IL15 cDNA with the front primer (SEQ ID NO: 21)
5'-TGGTTAACAACTGGGTGAATGTAATAAGTG-3' and the back primer (SEQ ID NO: 22)
5'-ACGCGTTTATCAAGAAGTGTTGATGAACATTTGGAC-3' by PfuUltra (Stratagene) under following PCR conditions: 94 C, 1 min; 63 C, 1 min; 72 C 1 min; ×35 cycles; 72 C, 10 min. The mature human IL15 protein gene was gel-purified and cloned into the shuttle vector, pcDNA3.1 Directional TOPO Expression Vector (Invitrogen), with the TOPO reaction according to the manufacture's protocol. The clone containing the mature human IL15 protein gene insert was identified based on the diagnostic PCR with the front primer (SEQ ID NO: 21)
5'-TGGTTAACAACTGGGTGAATGTAATAAGTG-3' and the back primer (SEQ ID NO: 22)
5'-ACGCGTTTATCAAGAAGTGTTGATGAACATTTGGAC-3' by RedTag (Sigma) under the following condition: 94 C, 1 min; 63 C, 1 min; 72 C, 1 min; ×35 cycles; 72 C, 10 min. The sequence of the correct clone was verified by DNA sequencing with GenomeLab Dye Termination Cycle Sequencing with a QUICK START KIT (Beckman Coulter) according to the manufacturer's protocol. The mature human IL15 protein gene was removed from the shuttle vector by digestion with HpaI and MluI and ligated into an expression vector pNEF38-c264scTCR which had been digested with HpaI and MluI. The pNEF38-c264scTCR expression vector contains the gene fragment encoding an immunoglobulin light chain leader (or secretory signal) sequence linked to the p53 (aa264-272) peptide-specific soluble chimeric single-chain TCR protein (c264scTCR) (Belmont, H. J. et al., 2006, Clin Immunol 121: 29-39). The vector also contains 5' regulatory/enhancer regions, transcription regulatory and promoter regions, translational regulatory/initiation/termination sequences including a Kozak consensus sequence and poly-A termination region, and 3' regulatory regions with putative matrix attachment regulatory elements. The vector also contains DNA sequences allowing selective growth in mammalian cells (SV40 promoter/neoR gene/poly-A) and bacteria (ori/amp gene). Cloning of the DNA fragment encoding mature human IL15 protein into the pNEF38-c264scTCR vector resulted in a c264scTCR/huIL15 fusion gene comprising the following sequence: 3'-immunoglobulin light chain leader—264 TCR V-α—peptide linker—264 TCR V-β—human TCR C-β—human IL-15. The resulting vector (pNEF38-c264scTCR/huIL15), shown in FIG. 2A, was identified based on the diagnostic PCR and reconfirmed by DNA sequencing. The sequences of the c264scTCR/huIL15 fusion gene and protein (including the leader sequence) are shown at FIG. 2B and FIG. 2C, respectively.

Figure 3A:
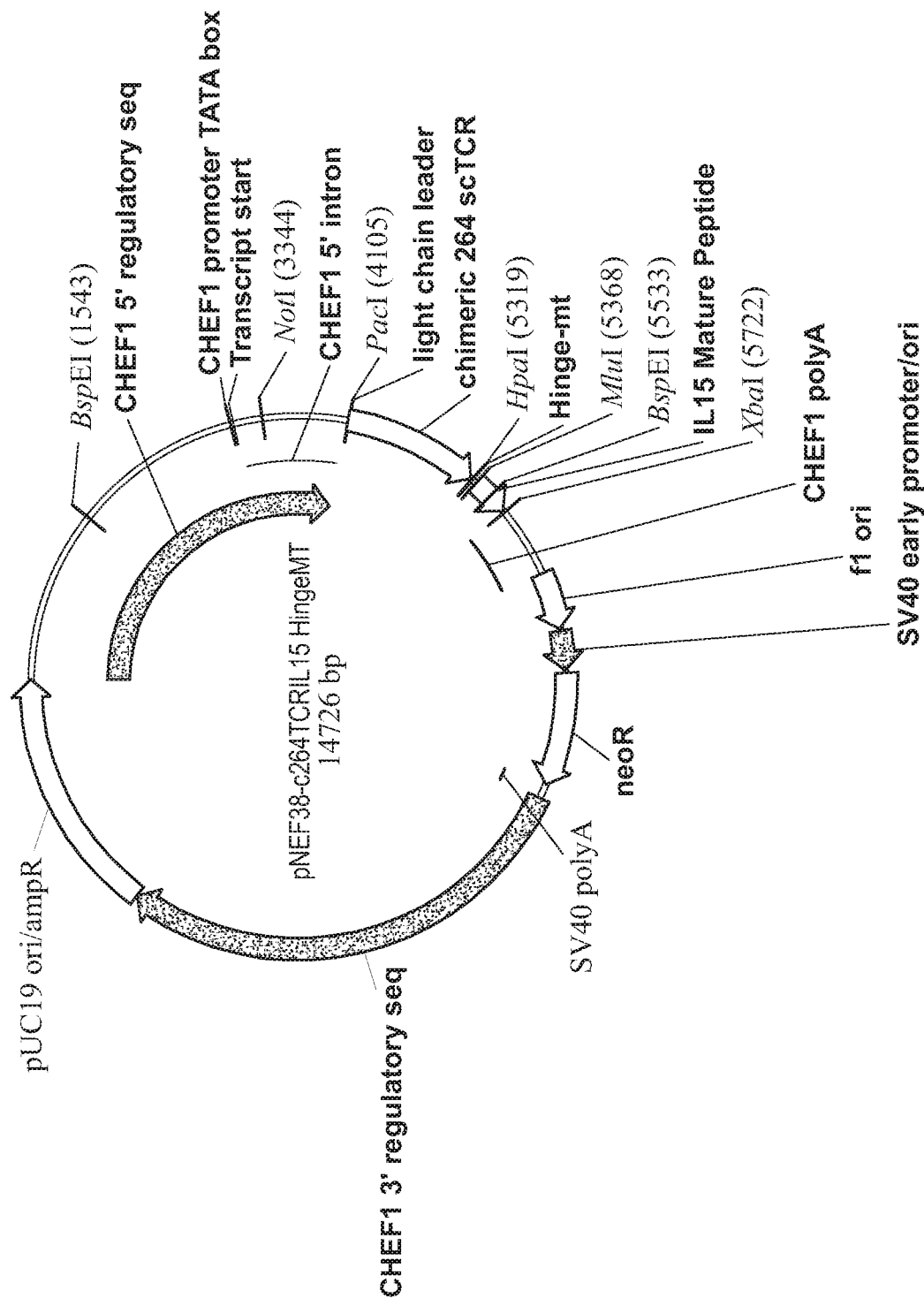
Figure 4A:
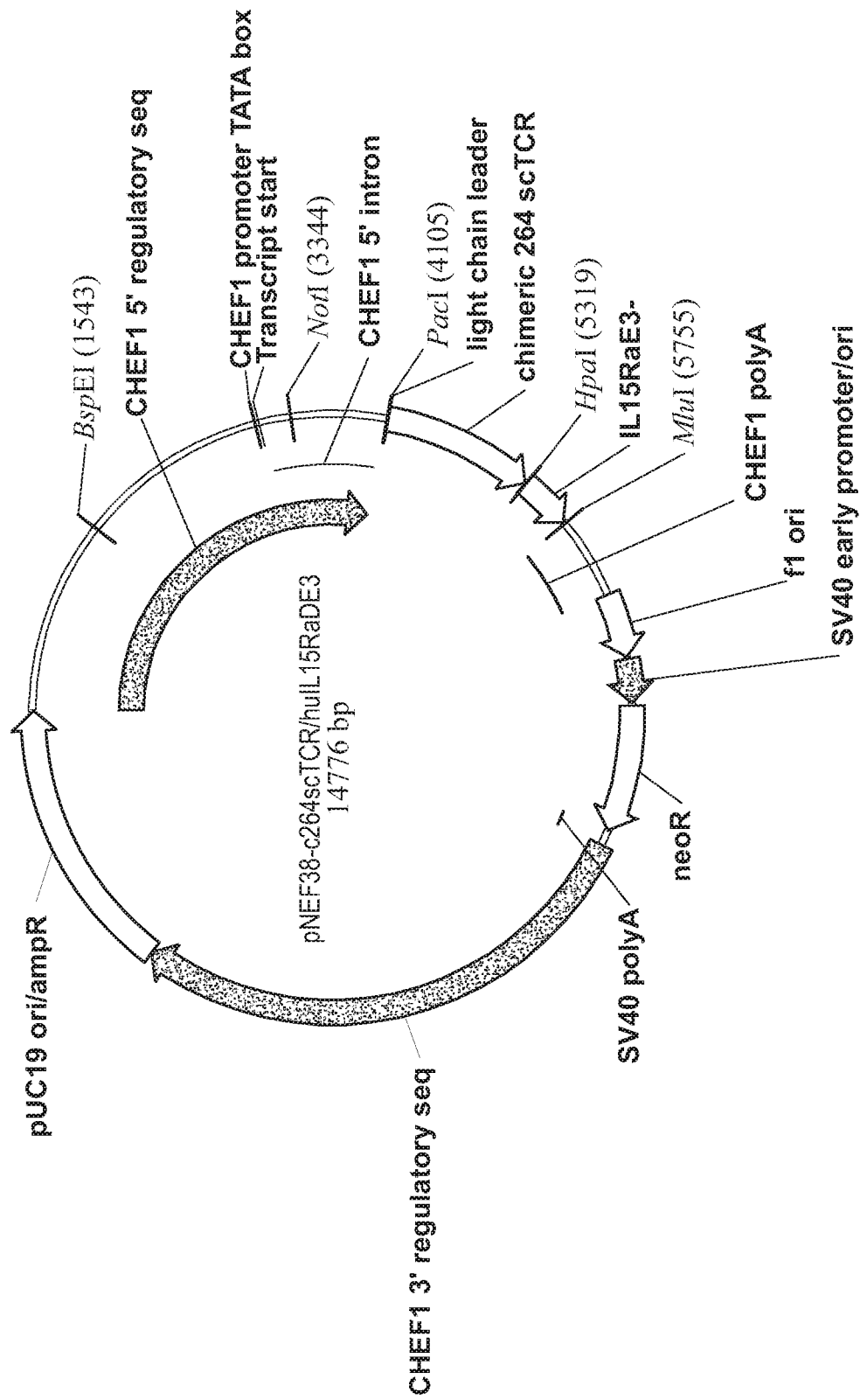

Example 3—Construction of the c264scTCR/huIL15 Gene Fusion Containing a Mutated Human IgG1 Hinge Region in an Expression Vector Construction of the pNEF38-c264scTCR/huIL15 vector was described at Example 2. A mutated hinge region from human IgG1 H chain where three cysteine residues were substituted with three serine residues was used to link c264scTCR and huIL15. The hinge region was mutated and amplified from 264scTCR/IgG1 gene described previously (Mosquera, L. A. et al., 2005, J Immunol 174: 4381-4388) with the front primer (SEQ ID NO: 23)
5'-TGGTGGGTTAACGAGCCCAAATCTTCTG-3' and the back primer (SEQ ID NO: 24)
5'-ATTATTACGCGTTGGAGACGGTGGAGATG-3' by PfuUltra (Stratagene) under following PCR conditions: 94 C, 30 sec; 65 C, 30 sec; 70 C 1 min; ×35 cycles; 72 C, 10 min. The 70 bp mutated human IgG1 hinge PCR-cDNA product was separated by electrophoresis on a 1% agarose gel and isolated. The cDNA product was purified from agarose with a Qiaquick Gel Extraction Kit (Qiagen). The mutated hinge region gene was digested with HpaI and MluI and ligated into pNEF38-c264scTCR which had been digested with HpaI and MluI. The clone containing the mutated hinge region gene insert was identified based on the diagnostic PCR with the front primer (SEQ ID NO: 25)
5'-TGAGTGATCGATACCACCATGGAGACAGACAC-3' and the back primer (SEQ ID NO: 24)
5'- ATTATTACGCGTTGGAGACGGTGGAGATG -3' by RedTag (Sigma) under the following condition: 94 C, 30 sec; 64 C, 30 sec; 70 C 1 min; ×35 cycles; 72 C, 10 min. The huIL15 was amplified from pNEF38-c264scTCR/huIL15 vector described at Example 2 with the front primer (SEQ ID NO: 26)
5'-TGGTGGACGCGTAACTGGGTGAATG-3' and the back primer (SEQ ID NO: 27)
5'-TGGTGGTCTAGAATTATCAAGAAGTGTTGATG -3' by PfuUltra (Stratagene) under following PCR conditions: 94 C, 30 sec; 65 C, 30 sec; 70 C 1 min; ×35 cycles; 72 C, 10 min. The 380 bp huIL15 PCR-cDNA product was separated by electrophoresis on a 1% agarose gel and isolated. The cDNA product was purified from agarose with a Qiaquick Gel Extraction Kit (Qiagen). The huIL15 gene was digested with MluI and XbaI and ligated into pNEF38-c264scTCR containing mutated hinge gene which had been digested with MluI and XbaI. The clone containing the huIL15 gene insert was identified based on the diagnostic PCR with the front primer (SEQ ID NO: 25)
5'-TGAGTGATCGATACCACCATGGAGACAGACAC-3' and the back primer (SEQ ID NO: 27)
5'- TGGTGGTCTAGAATTATCAAGAAGTGTTGATG -3' by RedTag (Sigma) under the following condition: 94 C, 30 sec; 64 C, 2 min; 70 C 2 min; ×35 cycles; 72 C, 10 min. The sequence of the correct clone was verified by DNA sequencing with GenomeLab Dye Termination Cycle Sequencing with a QUICK START KIT (Beckman Coulter) according to the manufacturer's protocol. The pNEF38-c264scTCR expression vector is described above at Example 2. Cloning of the DNA fragment encoding mutated human IgG1 hinge region and mature human IL15 protein into the pNEF38-c264scTCR vector resulted in a c264scTCR-hmt-huIL15 fusion gene comprising the following sequence: 3'-immunoglobulin light chain leader—264 TCR V-α—peptide linker—264 TCR V-β—human TCR C-β—mutated human IgG1 hinge-human IL-15. The resulting vector (pNEF38-c264scTCR-hmt-huIL15), shown in FIG. 3A, was identified based on the diagnostic PCR and reconfirmed by DNA sequencing. The sequences of the c264scTCR-hmt-huIL15 fusion gene and protein (including the leader sequence) are shown at FIG. 3B and FIG. 3C, respectively Example 4—Construction of the c264scTCR/huIL15RαΔE3 Gene Fusion in an Expression Vector The total RNA of PBMC was prepared as described above. Human IL15Rα gene containing coding region and a portion of 5' and 3' flanking regions was amplified from the total RNA of the PBMC with the front primer (SEQ ID NO: 28)
5'-AGTCCAGCGGTGTCCTGTGG-3' and the back primer (SEQ ID NO: 29)
5'-TGACGCGTTTAAGTGGTGTCGCTGTGCCCTG-3' by SUPERSCRIPT III One-Step RT-PCR Platinum Taq HiFi (Invitrogen) according to the following condition: for RT; 55 C, 30 min; 94 C, 2 min; for amplifying cDNA; 94 C, 1 min; 66 C, 1 min; 72 C, 1 min; ×35 cycles; 72 C, 5 min. The 970 bp human IL15 Rα PCR cDNA product was separated by electrophoresis on a 1% agarose gel and isolated. The cDNA was purified from agarose with a Qiaquick Gel Extraction Kit (Qiagen). The human IL15 Rα extracellular domain gene was amplified from the 970 bp human IL15 Rα cDNA with the front primer (SEQ ID NO: 30)
5'-TGGTTAACATCACGTGCCCTCCCCCCATG-3' and the back primer (SEQ ID NO: 29)
5'-TGACGCGTTTAAGTGGTGTCGCTGTGCCCTG-3' by PfuULTRA (Stratagene) under following PCR conditions: 94 C, 1 min; 72 C 2 min; ×35 cycles, 72 C, 10 min. The human IL15 Rα extracellular domain gene was gel-purified and cloned into the shuttle vector, pcDNA3.1 Directional TOPO Expression Vector (Invitrogen), by TOPO reaction according to the manufacturer's protocol. The clone containing the correct human IL15 Rα extracellular domain gene insert was chosen based on diagnostic PCR and reconfirmed by DNA sequencing with the GenomeLab Dye Termination Cycle Sequencing with a Quick Start Kit according to the manufacturer's protocol. The gene was determined to be human IL15 RαΔE3 extracellular domain gene. The human IL15 RαΔE3 extracellular domain gene was removed from the shuttle vector by digestion with HpaI and MluI and ligated into pNEF38-c264scTCR which had been digested with HpaI and MluI. Cloning of the DNA fragment encoding the human IL15 RαΔE3 extracellular domain into the pNEF38-c264scTCR vector resulted in a c264scTCR/huIL15Rα fusion gene comprising the following sequence: 3'-immunoglobulin light chain leader—264 TCR V-α—peptide linker—264 TCR V-β—human TCR C-β—IL15 RαΔE3 extracellular domain. The resulting vector (pNEF38-c264scTCR/huIL15RαΔE3), shown in FIG. 4A, containing the correct IL15 RαΔE3 extracellular domain gene insert was identified based on the diagnostic PCR and reconfirmed by DNA sequencing. The sequences of the c264scTCR/huIL15 RαΔE3 gene and protein are shown at FIG. 4B and FIG. 4C, respectively.

Figure 5A:
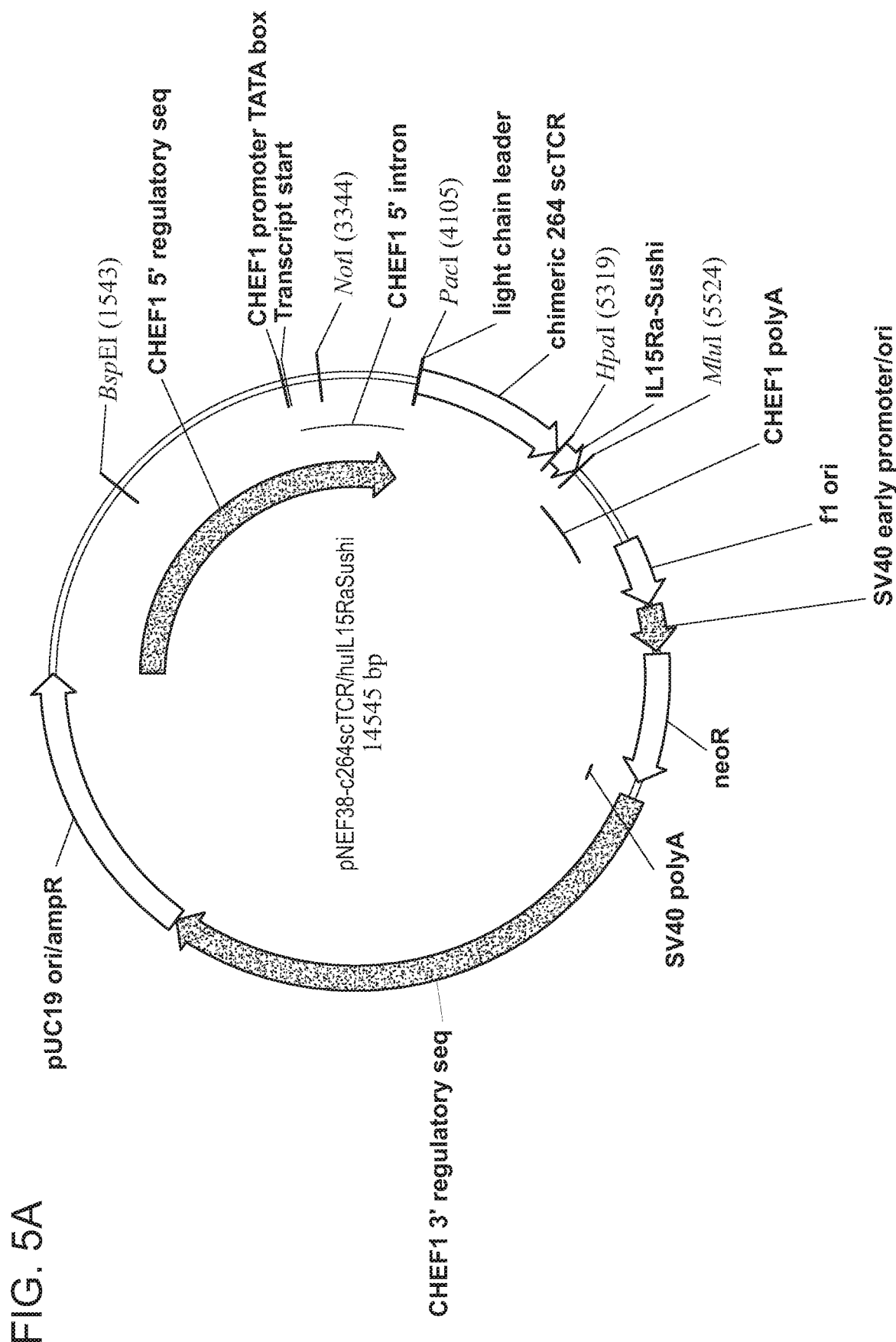

Example 5—Construction of c264scTCR/huIL15RαSushi Gene Fusion in an Expression Vector The total RNA of PBMC was prepared as described above. Human IL15RαSushi gene was amplified from the 970 bp human IL15 Rα cDNA (see Example 3) with the front primer (SEQ ID NO: 30)
5'-TGGTTAACATCACGTGCCCTCCCCCCATG-3' and the back primer (SEQ ID NO: 31)
5'-TTGTTGACGCGTTTATCTAATGCATTTGAGACTGG-3' by PfuULTRA (Stratagene) under following PCR conditions: 94 C, 1 min; 66 C, 1 min; 70 C, 1 min; ×35 cycles; 72 C, 10 min. The PCR product of human IL15RαSushi gene was gel-purified and digested with HpaI and MluI. The gene was ligated into pNEF38-c264scTCR which had been digested with HpaI and MluI. Cloning of the DNA fragment encoding the human IL15RαSushi domain into the pNEF38-c264scTCR vector resulted in a c264scTCR/huIL15Rα fusion gene comprising the following sequence: 3'-immunoglobulin light chain leader—264 TCR V-α—peptide linker—264 TCR V-β—human TCR C-β—human IL15RαSushi. The resulting vector, shown in FIG. 5A, containing the correct human IL15RαSushi gene insert was identified based on the diagnostic PCR and reconfirmed by DNA sequencing. The sequences of the c264scTCR/huIL15 RαSushi gene and protein are shown at FIG. 5B and FIG. 5C, respectively.

Example 6—Construction of c264scTCR/huIL15RαSushi Gene Fusion Containing a Mutated Human IgG1 Hinge Region in an Expression Vector Construction of the pNEF38-c264scTCR/huIL15RαSushi vector was described above. A mutated hinge region from human IgG1 H chain where three cysteine residues were replaced by three serine residues was used to link c264scTCR and huIL15RαSushi. The hinge region was mutated, amplified, ligated, and verified as above. The huIL15RαSushi was amplified from pNEF38-c264scTCR/huIL15RαSushi vector described above with the front primer (SEQ ID NO: 32)
5'-TAATAAACGCGTATCACGTGCCCTC-3' and the back primer (SEQ ID NO: 33)
5'-TGGTGGTCTAGATTATCATCTAATGCATTTG-3' by PfuUltra (Stratagene) under following PCR conditions: 94 C, 30 sec; 65 C, 30 sec; 70 C 1 min; ×35 cycles; 72 C, 10 min. The 250 bp huIL15RαSushi PCR-cDNA product was separated by electrophoresis on a 1% agarose gel and isolated. The cDNA product was purified from agarose with a Qiaquick Gel Extraction Kit (Qiagen). The huIL15RαSushi gene was digested with MluI and XbaI and ligated into pNEF38-c264scTCR containing mutated hinge gene which had been digested with MluI and XbaI. The clone containing the huIL15 gene insert was identified based on the diagnostic PCR with the front primer

```
                                            (SEQ ID NO: 23)
      5'-TGGTGGGTTAACGAGCCCAAATCTTCTG-3'
``` and the back primer

Figure 6A:
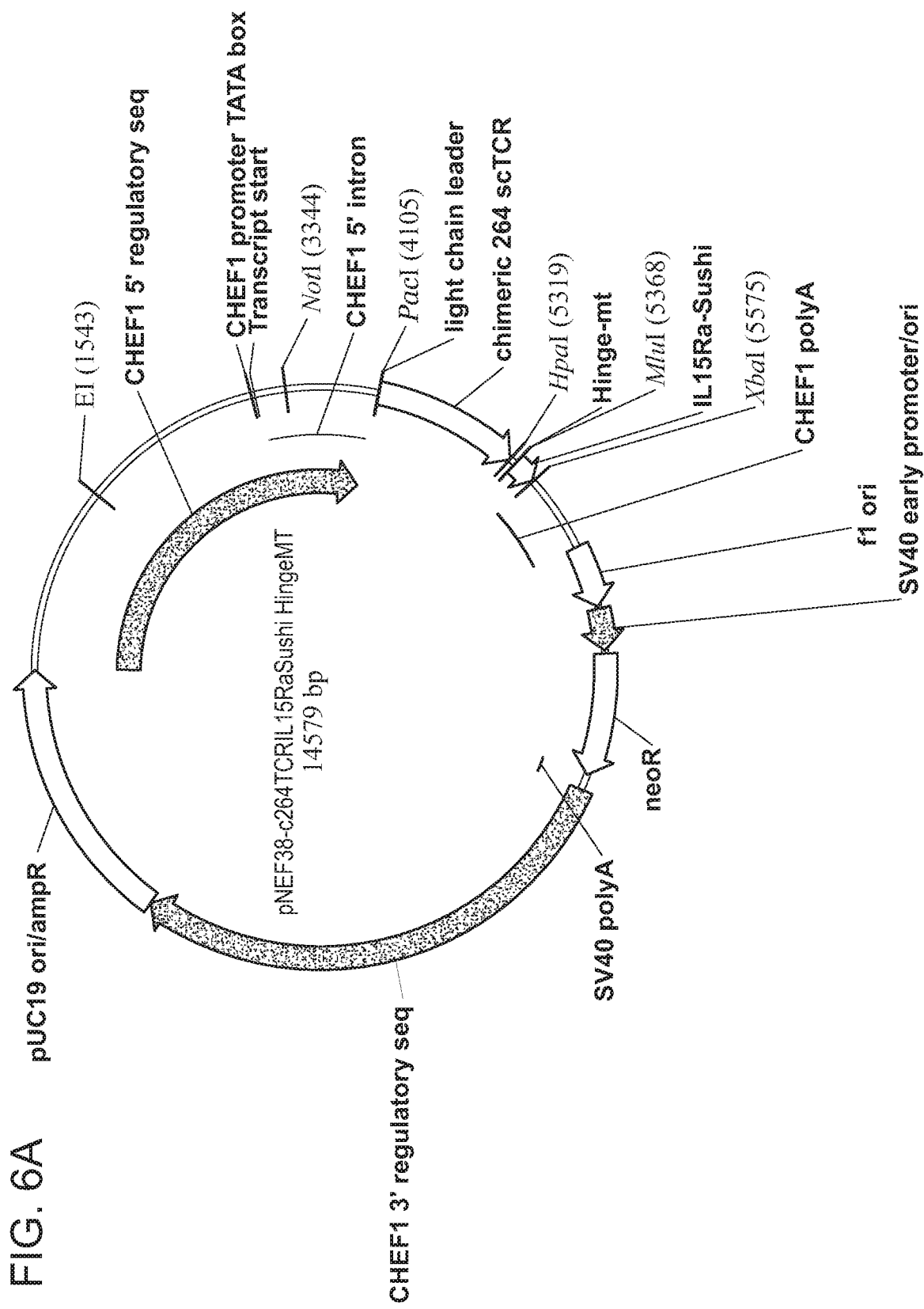

```
                                            (SEQ ID NO: 33)
      5'-TGGTGGTCTAGATTATCATCTAATGCATTTG-3'
``` by RedTag (Sigma) under the following condition: 94 C, 30 sec; 65 C, 1 min; 70 C 1 min; ×35 cycles; 72 C, 10 min. The sequence of the correct clone was verified by DNA sequencing with GenomeLab Dye Termination Cycle Sequencing with a QUICK START KIT (Beckman Coulter) according to the manufacturer's protocol. The pNEF38-c264scTCR expression vector is described above. Cloning of the DNA fragment encoding mutated human IgG1 hinge region and human IL15RαSushi protein into the pNEF38-c264scTCR vector resulted in a c264scTCR-hmt-huIL15RαSushi fusion gene comprising the following sequence: 3'-immunoglobulin light chain leader—264 TCR V-α—peptide linker—264 TCR V-β—human TCR C-β—mutated human IgG1 hinge-human IL15RαSushi. The resulting vector (pNEF38-c264scTCR-hmt-huIL15RαSushi), shown in FIG. 6A, was identified based on the diagnostic PCR and reconfirmed by DNA sequencing. The sequences of the c264scTCR-hmt-huIL15RαSushi fusion gene and protein (including the leader sequence) are shown at FIG. 6B and FIG. 6C, respectively.

Example 7—Construction of the c264scTCR/huIL15RαSushi and c264scTCR/huIL15 Genes in a Single Expression Vector To achieve expression of two fusion proteins of the invention in a single host cell, the genes encoding c264scTCR/huIL15RαSushi and c264scTCR/huIL15 were cloned into a single expression vector. The c264scTCR/huIL15RαSushi gene was amplified from the template described in Example 5 by PfuUltra (Stratagene) with the front primer 5'-TGAGTGTCCGGAACCACCATGGAGACAGACAC-3' (SEQ ID NO: 34) and the back primer 5'-TTGTTGGCGGCCGCTTATCATCTAATGCATTT-GAG-3' (SEQ ID NO: 35) under the following condition: 94 C, 1 min; 68 C, 1 min; 72 C, 2 min; ×35 cycles; 72 C, 10 min. The PCR product of c264scTCR/huIL15RαSushi gene was gel-purified, digested with BspEI and NotI and ligated into the pSUN34R1 expression vector which had been digested with BspEI and NotI. The pSUN34R1 expression vector contains two sites for cloning genes-of-interest as well as 5' regulatory/enhancer regions, transcription regulatory and promoter regions, translational regulatory/initiation/termination sequences including a Kozak consensus sequence and poly-A termination region, and intron and 3' regions with regulatory elements. This vector also contains DNA sequences allowing selective growth in mammalian cells (SV40 promoter/neoR gene/poly-A) and bacteria (ori/amp gene). The vector containing the correct c264scTCR/IL15RαSushi gene insert was identified based on the diagnostic PCR and reconfirmed by DNA sequencing. The c264scTCR/huIL15 gene was amplified from the template described in Example 2 by PfuUltra (Stratagene) with the front primer

```
                                            (SEQ ID NO: 25)
      5'-TGAGTGATCGATACCACCATGGAGACAGACAC-3'
``` and the back primer

Figure 7:
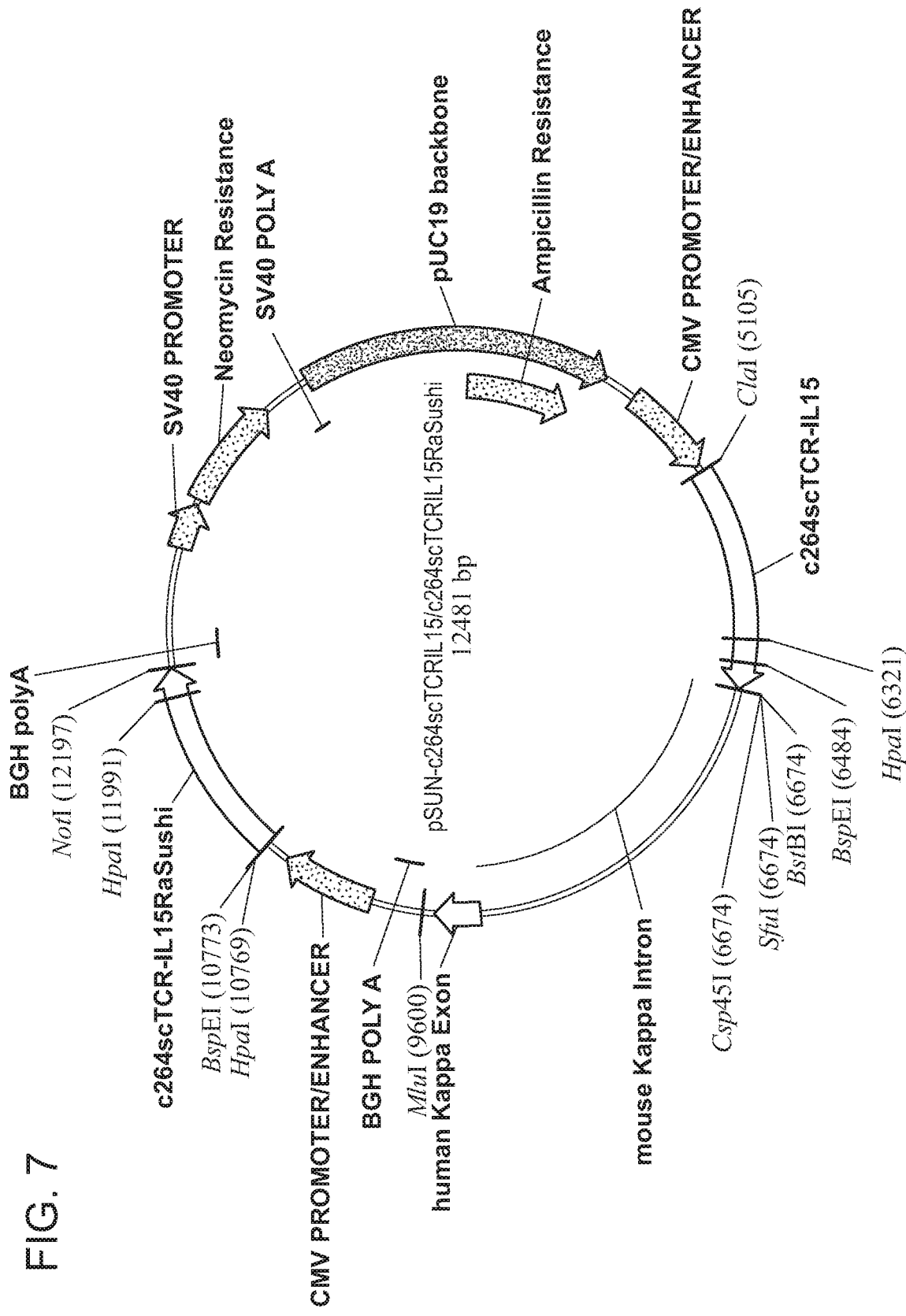
FIG. 7 is a map of pSun-c264scTCRIL15/c264scTCRIL15RaSushi expression vector.

```
                                            (SEQ ID NO: 36)
      5'-TGAGTGTTCGAATTATCAAGAAGTGTTGATGAAC-3'
``` under the following condition: 94 C, 1 min; 65 C, 1 min; 72 C, 2 min; ×35 cycles; 72 C, 10 min. The PCR product of c264scTCR/huIL15 gene was gel-purified, digested with ClaI and Csp45I and ligated into pSUN34R1-c264scTCR/huIL15RαSushi expression vector which had been digested with ClaI and Csp45I. The resulting vector (pSun-c264scTCRIL15/c264scTCRIL15RaSushi), shown in FIG. 7, containing the correct c264scTCR/huIL15 gene insert was identified based on the diagnostic PCR and reconfirmed by DNA sequencing. This vector contains both c264scTCR/huIL15RαSushi and c264scTCR/huIL15 genes.

Example 8—Construction of c264scTCR/huIL15RαΔE3 and c264scTCR/huIL15 Genes in a Single Expression Vector The c264scTCR/huIL15RαΔF3 fusion gene was amplified from the template described in Example 4 by PfuUltra (Stratagene) with the front primer

```
                                            (SEQ ID NO: 34)
      5'-TGAGTGTCCGGAACCACCATGGAGACAGACAC-3'
``` and the back primer

Figure 8:
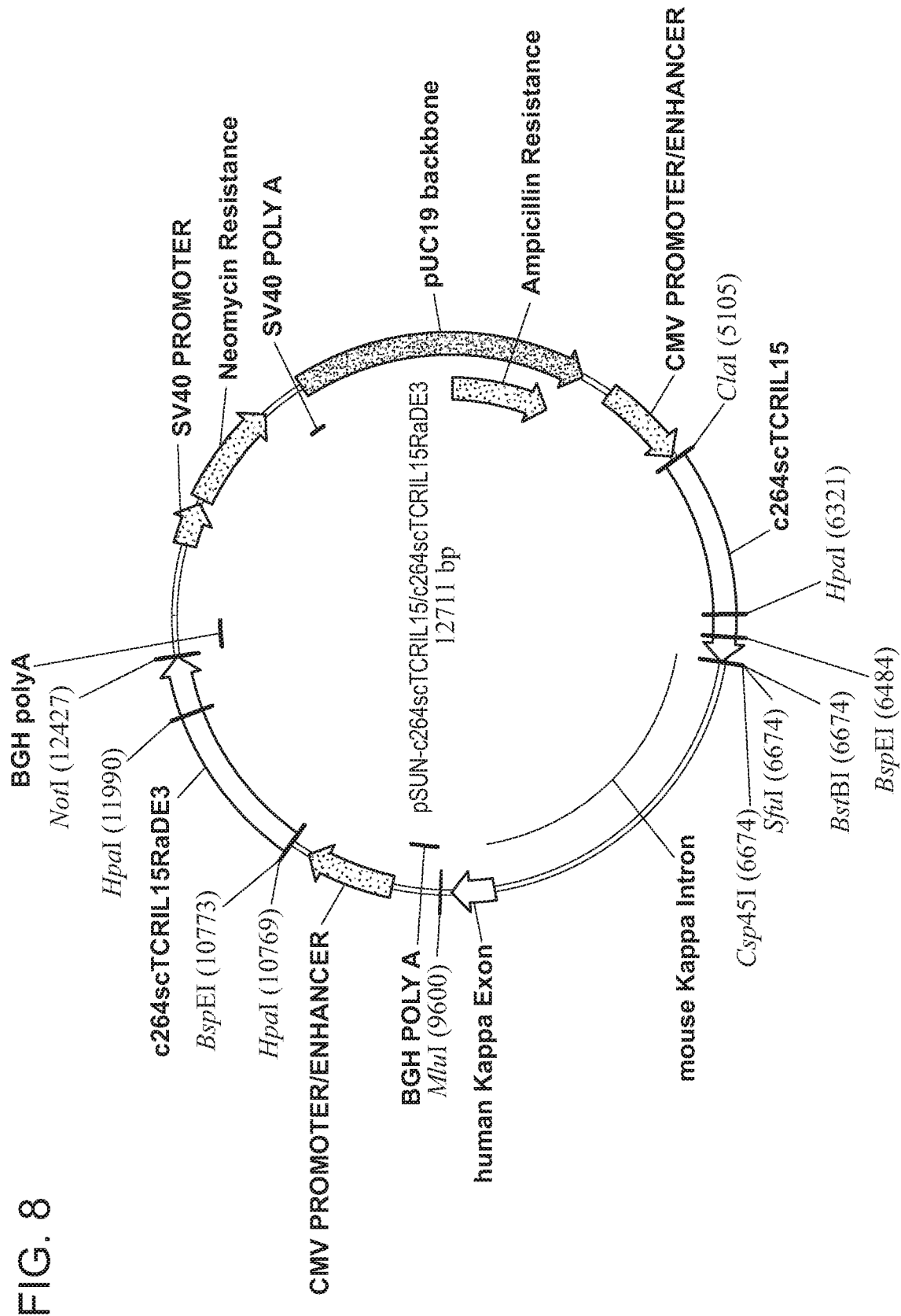
FIG. 8 is a map of pSun-c264scTCRIL15/c264scTCRIL15RaDE3 expression vector.

```
                                            (SEQ ID NO: 37)
      5'-TTGTTGGCGGCCGCTTATCAAGTGGTGTCGCTG-3'
``` under the following condition: 94 C, 1 min; 68 C, 1 min; 72 C, 2 min; ×35 cycles; 72 C, 10 min. The PCR product of c264scTCR/huIL15R αΔE3 gene was gel-purified, digested with BspEI and NotI and ligated to the expression vector pSUN34R1 which had been digested with BspEI and NotI. The vector containing the correct c264scTCR/huIL15R αΔE3 gene insert was identified based on the diagnostic PCR and reconfirmed by DNA sequencing. The c264scTCR/huIL15 gene was amplified and cloned into the expression vector as described on Example 7. The resulting vector (pSun-c264scTCRIL15/c264scTCRIL15RaDE3), shown in FIG. 8, containing the correct c264scTCR/huIL15 gene insert was identified based on the diagnostic PCR and reconfirmed by DNA sequencing. This vector contains both c264scTCR/huIL15R αΔE3 and c264scTCR/huIL15 genes.

Figure 9A:
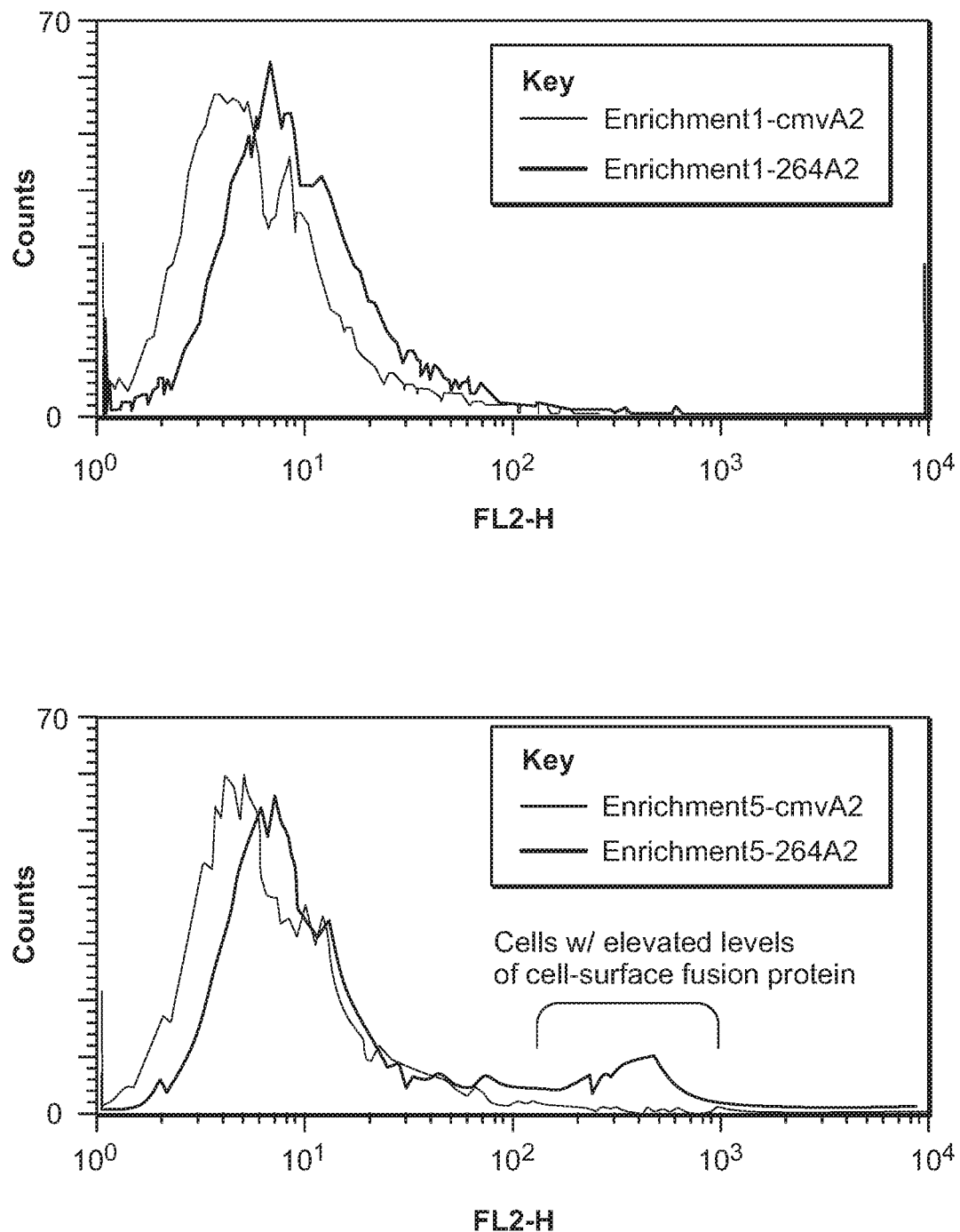
FIG. 9A and FIG. 9B set forth characterization of transfected cells expressing TCR/IL15Rα fusion protein.
Figure 9B:
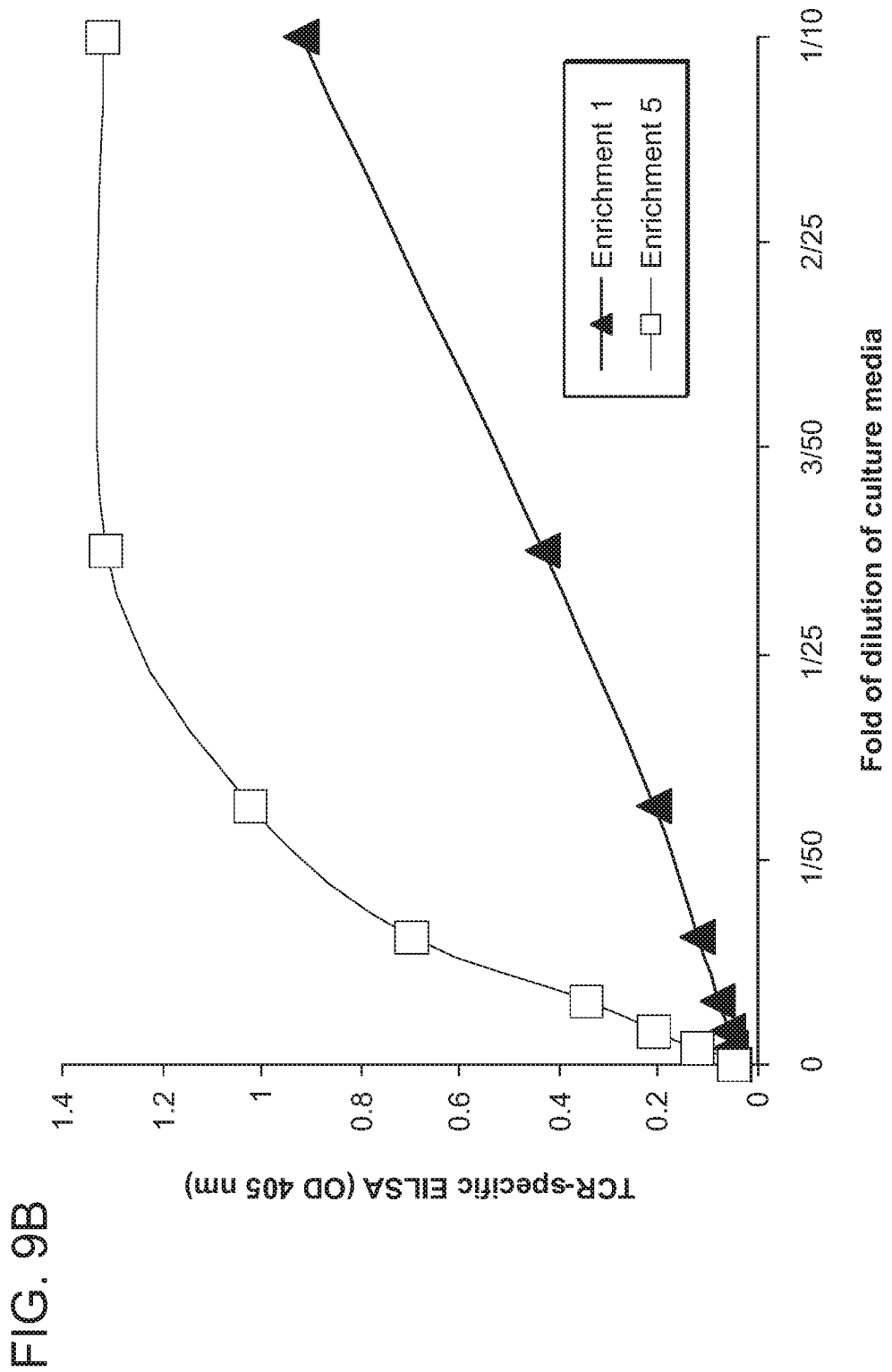

Example 9—Generation of Transfected Host Cell Lines Producing Fusion Proteins The expression vectors can be introduced into a variety of host cell lines by several different transformation, transfection or transduction methods. In one such method, CHO-K1 cells (5×10$^4$) were seeded in a 6-well plate and cultured overnight in a CO$_2$ incubator. The cells were transfected with 5 μg of expression vector containing the TCR/IL15 and/or TCR/IL15Rα fusion genes using 10 μL of Mirus TransIT-LT1 reagent (Minis) according to the manufacturer's protocol. The cells were selected with 4 mg/mL of G418 (Invitrogen) one day after the transfection. The G418 resistant cells were expanded and TCR fusion protein expressing cells were enriched by 3-5 rounds of MACS selection as described below. The cells were detached in 10 mM EDTA and washed once with IMDM containing 10% FBS. Cells were resuspended ($10^7$ cells in 100 μL) and incubated with 5 μg of R-Phycoerythrin (PE) conjugated p53 (aa264-272)/HLA-A2 tetramer reagent for 15 min at 4 C. The cells were washed once and incubated with anti-PE antibody conjugated magnetic beads (Miltenyi Biotec) for 15 min at 4 C. The cells were loaded to a magnetic column (in a magnetic field) and the unbound cells were removed with wash buffer (PBS containing 0.5% BSA). The column-bound cells were eluted with IMDM containing 10% FBS after the column had been removed from the magnetic field. This procedure allows enrichment of fusion protein-expressing cells based on the transient display of the soluble fusion protein on the cell surface during the production/secretion process. The cell surface association of the fusion proteins was monitored after each enrichment. Levels of cell surface-bound fusion proteins determined by flow cytometry were compared to levels of soluble fusion proteins present in the cell culture media as determined by ELISA. An example of the comparison is shown in FIGS. 9A and 9B. In this example, CHO-K1 cells transfected with pNEF38-c264scTCR/huIL15RαSushi were enriched by MACS for one to five times and were then seeded ($1\times10^6$ cells/well) on a 6-well plate. After 24 hours, cells were then detached with 10 mM EDTA, washed once with IMDM+10% FBS, and stained (at $2\times10^5$ cells/100 μL of IMDM+10% FBS) with 0.6 μg of PE-conjugated p53 (aa264-272)/HLA-A2 tetramer or same amount of control PE-conjugated CMVpp65 (aa495-503)/HLA-A2 tetramer for 30 min at 4 C. Cells were washed once and analyzed for levels of cell surface associated soluble fusion protein by flow cytometry, as shown in FIG. 9A. The level of soluble fusion protein secreted into the cell culture medium was also determined by TCR-specific ELISA with a capture antibody, anti-human TCR Cβ antibody (BF1), and a detection antibody, biotinylated anti-human TCR Cβ antibody (W4F) described previously (5), as shown in FIG. 9B. The results indicate that the magnetic bead-based enrichment process yielded transfectants that produced increased levels of soluble fusion protein. The enriched transfected cells were then subcloned three times by the limiting dilution and production cell lines were screened based on the level of soluble fusion protein secreted into the culture media (determined by ELISA described above). Production cell lines were expanded and grown in IMDM+10% FBS or serum-free media under conditions (i.e. flasks, spinners, fermenters, bags, bottles) suitable to generate the soluble fusion protein.

In some cases, host cells were co-transfected with different expression vectors to generate transfectants capable of expressing multiple fusion proteins. Transfectants expressing one fusion protein could also be re-transfected with a one or more expression vectors to generate transfectants expressing multiple fusion proteins. Cells were also transfected with an expression vector containing more that one fusion protein genes, as exemplified in Examples 7 and 8, to generate a transfectant expressing multiple fusion proteins. The resulting cells could be used to produce the multi-component fusion protein complexes of the invention as soluble molecules in the cell culture medium.

High levels of fusion protein or fusion protein complex production can also be achieved through cell transfection and selection methods described in U.S. Ser. No. 09/204,979.

Figure 10A:
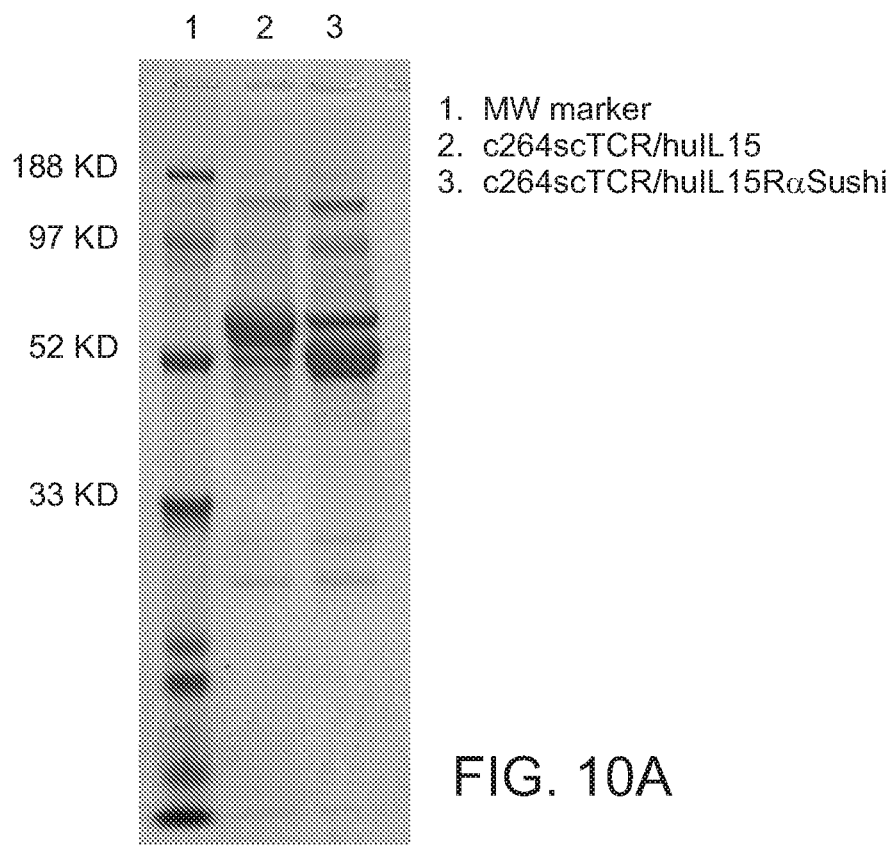
FIG. 10A and FIG. 10B shows analysis of TCR/IL15 and TCR/IL15Rα fusion proteins by reducing SDS PAGE.
Figure 10B:
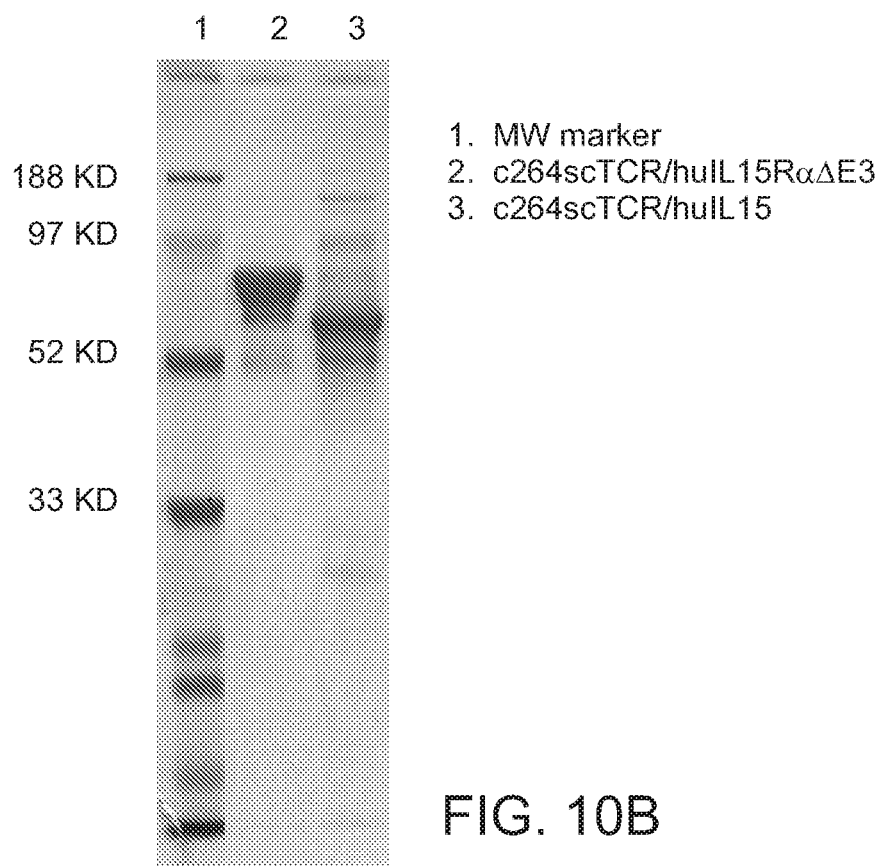

Example 10—Purification of the TCR/IL15 and TCR/IL15Rα Fusion Proteins or Fusion Protein Complexes Soluble fusion proteins or fusion protein complexes of the invention can be purified from the host cells or cell culture media using a variety of methods, including by selective partitioning or solubility in solvents or by separation (i.e. via chromatography) based on charge, hydrophobicity, hydrophilicity, size, and/or selective or semi-selective binding to a ligand. Soluble fusion proteins or fusion protein complexes can be generated from insoluble materials through use of the appropriate protein folding conditions. In one example, c264scTCR/IL15 fusion protein was purified from cell culture media by affinity chromatography using a antibody (BF1) recognizing the human TCR-Cβ domain. Typically, a column containing BF1-conjugated Sepharose was first equilibrated with 20 mM Tris-HCl pH 8.0 (loading buffer) and then loaded at 2 ml/min with pH adjusted cell culture media containing c264scTCR/IL15 fusion protein. The column was then washed with 5 column volumes of the loading buffer to remove unbound proteins, and the c264scTCR/IL15 fusion protein was eluted with 4 column volumes of 0.5M Na-citrate, pH 4. After collection, the eluate was adjusted to pH 8.0 by 2M Tris-HCl pH 8.0. The purified protein was buffer exchanged into PBS and filtered using 0.22 μm filter. The BF1 column was stripped with 50 mM Glycine-HCl pH 3.0, and stored in 20% ethanol at 4 C for further use. The fusion protein could be further purified by ion exchange and/or size exclusion chromatography. Cell culture supernatants containing c264scTCR/IL15, c264scTCR/IL15RαSushi and c264scTCR/IL15RαΔE3 fusion proteins were purified by the above methods and samples of the purified fusion proteins were analyzed by electorphoresis on SDS polyacrylamide gels under reducing conditions and followed by staining with Coomassie brilliant blue. Examples of such gels are shown in FIG. 10. The major protein bands correspond to the correct molecular weights expected based on fusion protein sequences.

Figure 11A:
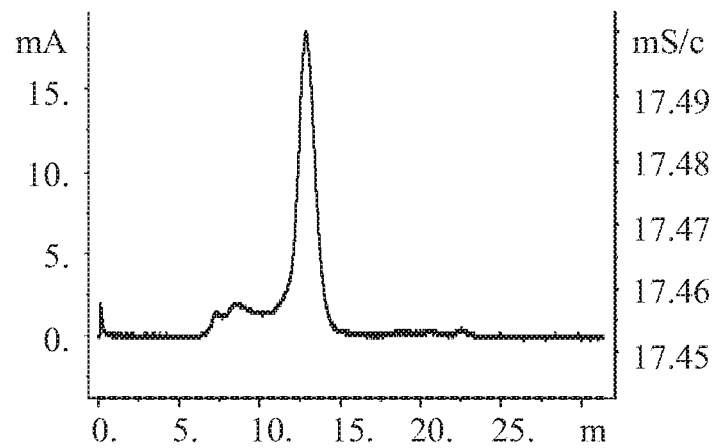
FIG. 11A, FIG. 11B, and FIG. 11C show analysis of TCR/IL15, TCR/IL15Ra and fusion protein complexes by size exclusion chromatography.
Figure 11B:
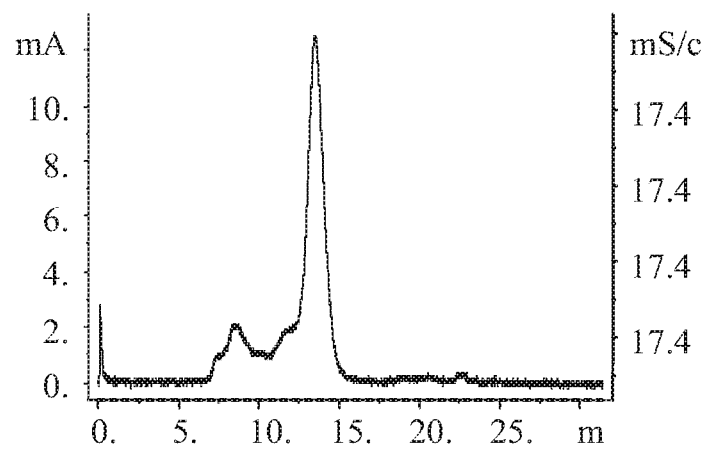
Figure 11C:
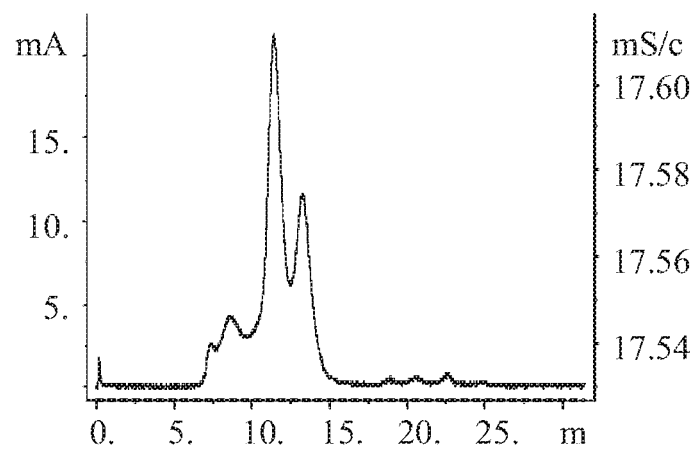

Example 11—Generation of a Fusion Protein Complex of the TCR/IL15 and TCR/IL15Rα Fusion Proteins IL15 specifically binds to the extracellular IL15Rα domain with high affinity (4). Thus a complex of fusion proteins bearing the IL-15 and IL15Rα domains can be formed under a variety of conditions, including within the expression cell or extracellularly with unpurified or purified fusion proteins. In one example, equal molar amounts of purified fusion proteins can be mixed under the appropriate conditions (i.e. 10 min at room temperature) to form a fusion protein complex. Complex formation can be monitored in using a variety of techniques including direct binding assays, competitive binding assays, immunoprecipitation, surface plasma resonance, or analyses based on complex size, activity or other properties. For example, as shown in FIG. 11, size exclusion chromatography can monitor the formation of complexes comprising c264scTCR/huIL15 and c264scTCR/huIL15RαSushi fusion proteins based on molecular weight. In this study, about 100 μg of c264scTCR/huIL15 (0.5 mg/ml) was loaded on a Superdex 200 HR 10/30 column for the analysis. The calculated molecular weight for c264scTCR/huIL15 is about 57 kD. Based on SEC profile (FIG. 11A), the estimated molecular weight is about 98 kD, suggesting that this fusion protein is likely a monomer. Similarly, about 60 μg of c264scTCR/huIL15RαSushi fusion protein (0.3 mg/ml) was loaded on the Superdex column. The calculated molecular weight for c264scTCR/huIL15RαSushi is about 52 kD. Based on SEC profile (FIG. 11B), estimated molecular weight of the fusion protein is about 81 kD, again suggesting this fusion protein is a monomer. Previous SEC analysis of other TCR-based fusion proteins showed similar differences between the calculated monomeric molecular weight and the estimated molecular weight of the glycosylated fusion protein. When the c264scTCR/huIL15 and c264scTCR/huIL15RαSushi fusion proteins were mixed in equal molar amounts and about 126 μg of the mixed proteins (0.63 mg/ml) were loaded on the column, the profile shown in FIG. 11C was obtained. Molecular weights of two major peaks were estimated: one at about 170 kD, which is a heterodimer of the two fusion proteins and another one at about 91 kD, which is likely a mix of monomeric forms of the fusion proteins. Thus, the appearance of the 170 kD species in the mixed c264scTCR/huIL15+c264scTCR/huIL15RαSushi fusion protein preparation is evidence that the fusion protein complex of the invention can be generated.

Figure 12A:
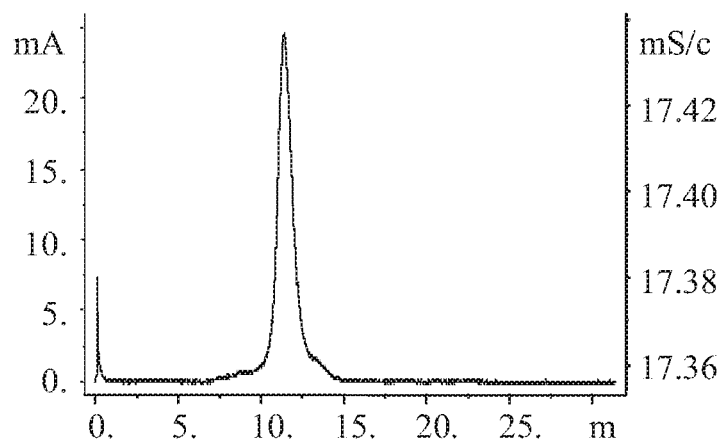
FIG. 12A and FIG. 12B is an analysis of TCR/IL15Rα and fusion protein complexes by size exclusion chromatography.
Figure 12B:
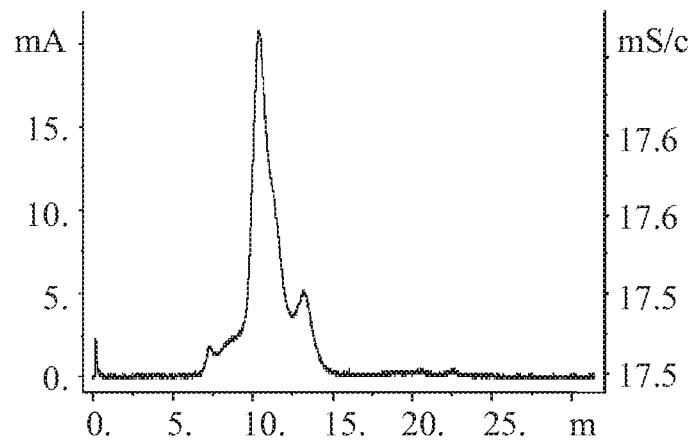

Analysis of the fusion protein complex comprising c264scTCR/huIL15 and c264scTCR/huIL15RαΔE3 fusion proteins was also conducted. About 100 μg of c264scTCR/huIL15RαΔE3 fusion protein (0.5 mg/ml) was loaded on the Superdex column. The calculated molecular weight for c264scTCR/huIL15RαΔE3 is about 60 kD. Based on SEC profile (FIG. 12A), estimated molecular weight of the protein is about 173 KD, suggesting this protein exists as a homodimer. When the c264scTCR/huIL15 and c264scTCR/huIL15RαΔE3 fusion proteins were mixed in equal molar amounts and about 118 μg of the mixed proteins (0.59 mg/ml) were loaded on the column, the profile shown in FIG. 12B was obtained. Molecular weights of two major peaks were estimated: one is >210 kD, which is likely a tetramer composed of two heterodimers and the other is about 93 kD, likely to be c264scTCR/huIL15 monomer. Thus, the appearance of the 170 kD species in the mixed c264scTCR/huIL15+c264scTCR/huIL15RαΔE3 fusion protein preparation is evidence that the fusion protein complex of the invention can be generated.

Figure 13:
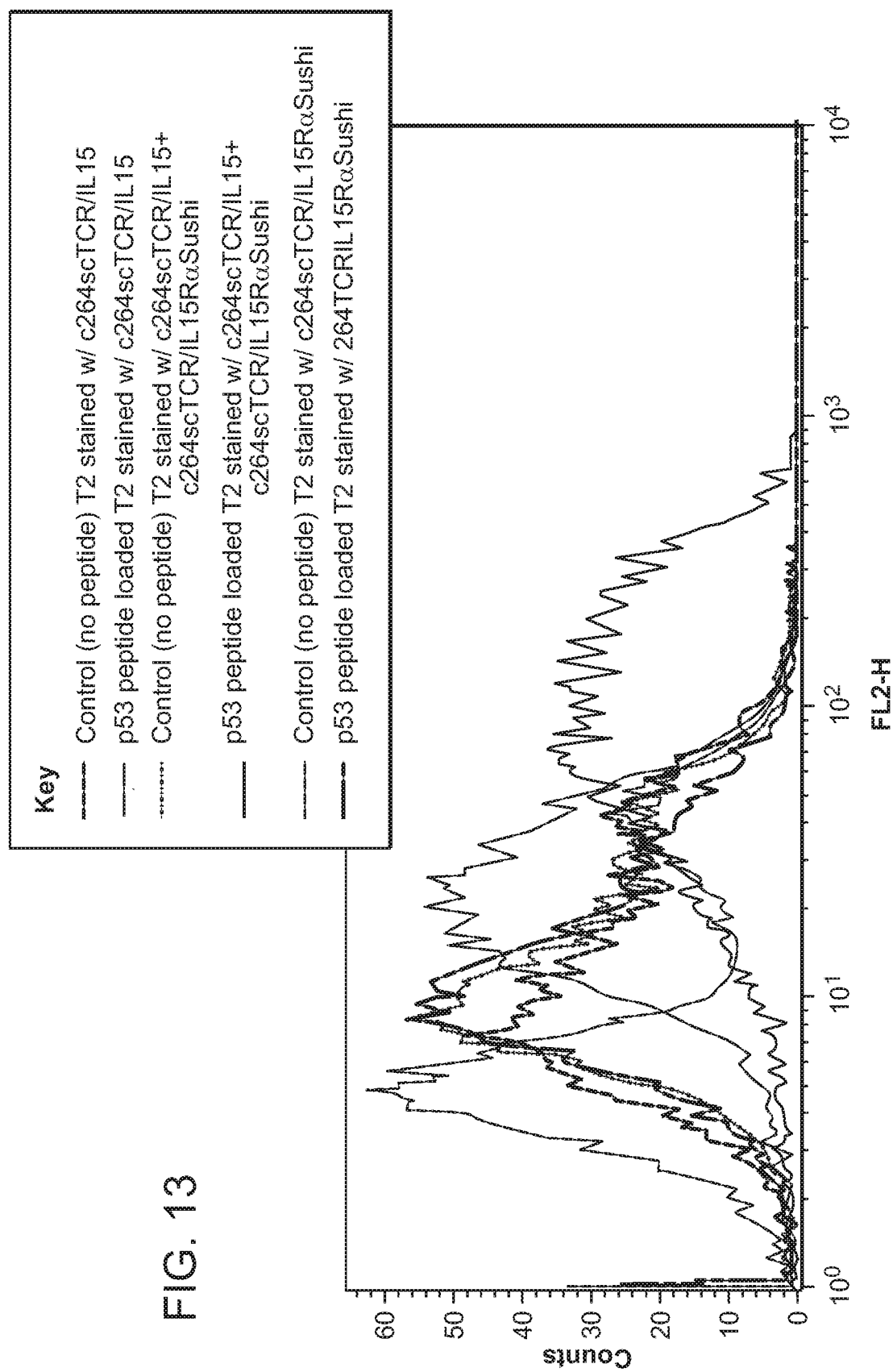
FIG. 13 is a graph showing the binding of TCR/IL15, TCR/IL15Rα and fusion protein complexes to peptide/WIC complexes displayed on cells, as determined by flow cytometry.

Example 12—Fusion Protein Complex of the TCR/IL15 and TCR/IL15Rα Fusion Proteins Exhibits Enhanced Binding for Peptide/MHC Complexes The fusion protein complexes generated as described above were characterized for their ability to bind the TCR-specific antigen, p53 (aa264-272)/HLA-A2.1. To generate cells presenting this antigen, HLA-A2.1-positive T2 cells were loaded with p53 (aa264-272) peptide at 26 C overnight and then stored at $5 \times 10^6$ cells/mL in a liquid nitrogen. T2 cells that were not incubated with peptide serve as controls. The p53 peptide-loaded or control T2 cells were thawed and resuspended in 1 mL of IMDM+10% FBS. The cells ($5 \times 10^5$/100 μL) were then stained for 30 min at RT with 0.5 μg of following fusion proteins: c264scTCR/huIL15, c264scTCR/huIL15RαSushi, c264scTCR/huIL15+c264scTCR/huIL15RαSushi complex. Cells were washed once with washing buffer (PBS containing 0.5% BSA and 0.05% sodium azide) and stained with 0.1 μg of biotinylated mouse monoclonal anti-human TCR Cβ antibody (BF1) in 100 μL of washing buffer for 30 min at RT. Cells were washed once and stained with 0.5 μg of R-Phycoerythrin conjugated streptavidin in 100 μL of washing buffer for 30 min at RT. Cells were washed and resuspended for analysis by flow cytometry. As shown in FIG. 13, each of the fusion proteins was capable of specifically staining p53 peptide-loaded cells. In addition, the c264scTCR/huIL15+c264scTCR/huIL15RαSushi fusion protein complex displayed enhanced specific binding via the multivalent c264scTCR domains to the p53 (aa264-272)/HLA-A2.1 complexes displayed on the T2 cells. In particular, the dimeric fusion protein complex showed better staining of the p53 peptide-loaded T2 cells than the monomeric c264scTCR/huIL15 or c264scTCR/huIL15RαSushi fusion proteins. These data suggest that the multimeric fusion protein complex will provide better antigen recognition properties than monomeric form of the fusion proteins.

Example 13—Generation of huIL-15 Mutant Genes and Construction of c264scTCR-Hmt-huIL15 Mutant Gene Expression Vectors As described above, c264scTCR/huIL15+c264scTCR/huIL15RαSushi polypeptides are able to form a complex through interactions of the IL-15 and IL-15Rα domains and the multivalent fusion protein complex has enhanced binding for peptide/MHC complexes. Such a fusion protein complex has advantages as an antigen-specific or targeted research, diagnostic and therapeutic agent based on the enhanced binding activity. The ability of the IL-15/IL-15Rα domains of the fusion protein to bind cells expressing IL-15 receptors is also an desirable feature as indicated herein. However, there are applications where it is advantageous to increase or decrease the ability of the IL-15/IL-15Rα domains to interact with and/or effect the responses of cells expressing IL15 receptors. For example; it may be desirable to reduce this interaction in the applications (i.e. research and diagnostic uses) where the primary goal is to use the fusion protein complex for specific detection of peptide/MHC complexes. In therapeutic applications, it may also be desirable to generated fusion protein complexes that contain IL-15 domains capable of increasing or decreasing IL-15-mediated responses. To address this issue, mutational analysis was carried out to identify residues in IL-15 that effect its binding to IL-2/15Rβγc complex without effecting its interactions to IL-15Rα. The resulting mutations may create IL-15 variants including antagonists or agonists. In addition to use in the fusion proteins of the invention, the resulting IL-15 antagonists and agonists also may have utility as soluble cytokines (i.e., non-fusion proteins) or as a complex with IL-15Rα domains, for research, diagnostic or therapeutic applications. For example, IL-15 antagonists may be useful in suppressing unwanted immune responses whereas IL-15 agonists may be used to stimulate immune responses in therapeutic strategies to treat various diseases.

Based on a comparison between the amino acid sequence and structure of IL-15 with IL-2, several amino acids were identified that could potentially effect interactions between IL-15 and IL-15Rα, IL-15Rβ and/or γC. As showed in Table 1 and FIG. 14A, IL-15 variants were created where the potential binding sites of the mature human IL-15 protein to IL-15Rβγc receptors, amino acids at positions 8, 61, 65, 72, and 108 (numbering based on mature native human IL-15 sequence), were each substituted or combined with two or more other substitutions. The aspartic acid at position 8 was substituted with alanine or asparagine. The aspartic acid at position 61 was substituted with alanine. The asparagine at position 65 was substituted with alanine or aspartic acid. The asparagine at position 72 was substituted with arginine or aspartic acid. The glutamine at position 108 was substituted with alanine. Both Asp at position 8 and Gln at position 108 were each substituted with an alanine. Both Asp at position 8 and Asn at position 65 were each substituted with an asparagine or alanine. Both Asp at position 8 and Asn at position 65 were each substituted with a serine or arginine. To generate IL-15 mutants, the overlapping PCR was used.

For example, to generate Asp at position 8 with the substitution of alanine or asparagines residues, pNEF38-c264scTCR/huIL15 vector was used as template to amplify two overlapping c-DNA fragments with the front primer for fragment 1

```
                                       (SEQ ID NO: 26)
5'-TGGTGGACGCGTAACTGGGTGAATG-3'
``` and with the back primer for fragment 1

```
                                       (SEQ ID NO: 38)
5'-AGATCTTCAATTTTTTTCAAMKHACTTATTACATTCACCCAG-3'
``` and with the front primer for fragment 2

```
                                       (SEQ ID NO: 39)
5'-ACTGGGTGAATGTAATAAGTDMKTTGAAAAAAATTGAAGATC-3'
``` and with the back primer for fragment 2

```
                                       (SEQ ID NO: 40)
5'-TGGTGGTCTAGATTATCAAGAAGTGTTGATG-3'
``` by PfuUltra (Stratagene) under following PCR conditions: 94 C, 1 min; 66 C, 1.5 min; 72 C 1.5 min; ×35 cycles; 72 C, 10 min. The fragments 1 and 2 PCR-cDNA products were separated by electrophoresis on a 1% agarose gel and isolated. The cDNA product was purified from agarose with a Qiaquick Gel Extraction Kit (Qiagen). The fragments 1 and 2 PCR-cDNA products were fused together with PfuUltra (Stratagene) under following PCR conditions: 94 C, 1 min; 66 C, 1.5 min; 72 C 1.5 min; ×10 cycles. The overlapping PCR-cDNA fragment was amplified with the front primer

```
                                       (SEQ ID NO: 26)
5'-TGGTGGACGCGTAACTGGGTGAATG-3'
``` and with the back primer

Figure 14B:
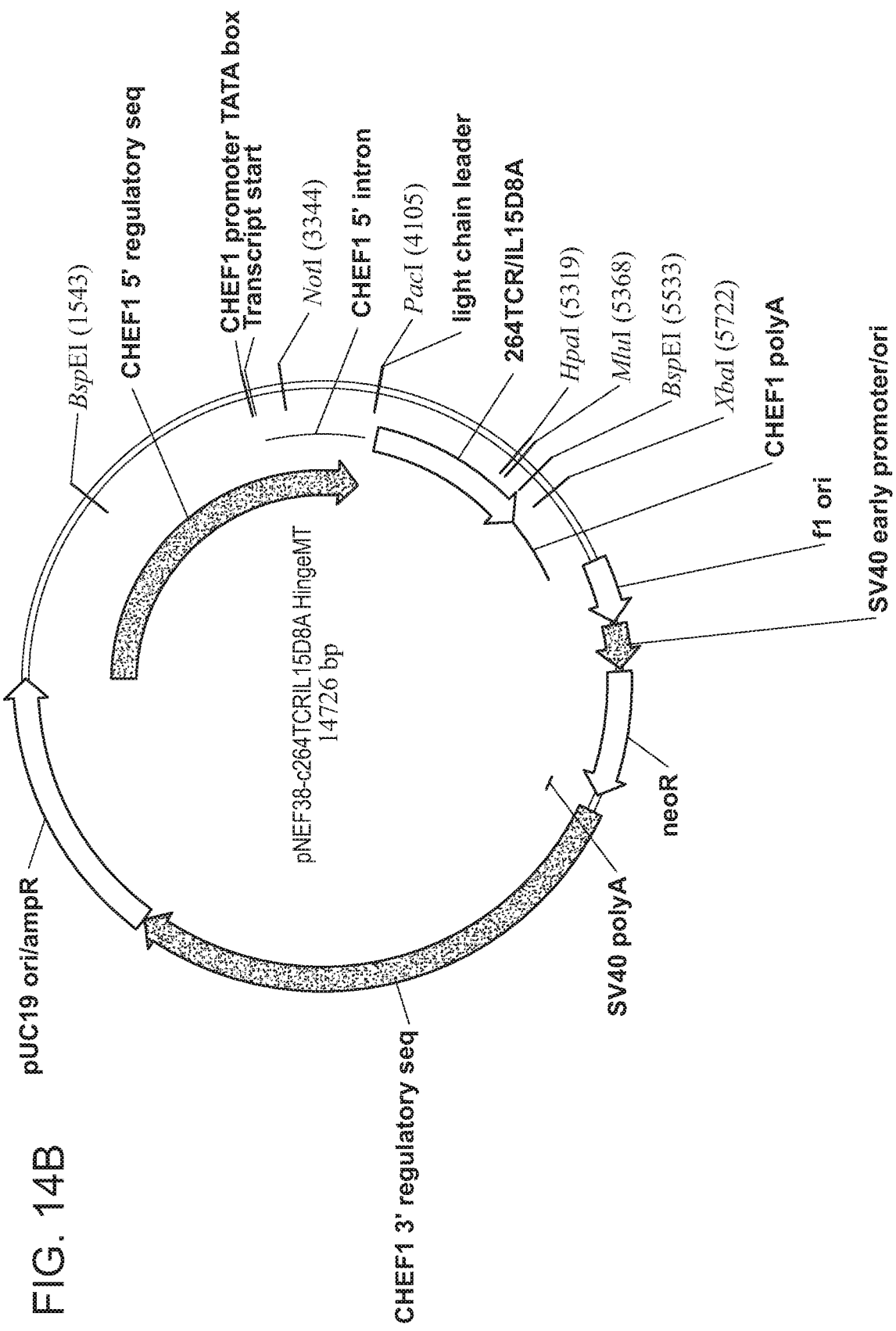
Figure 14C:
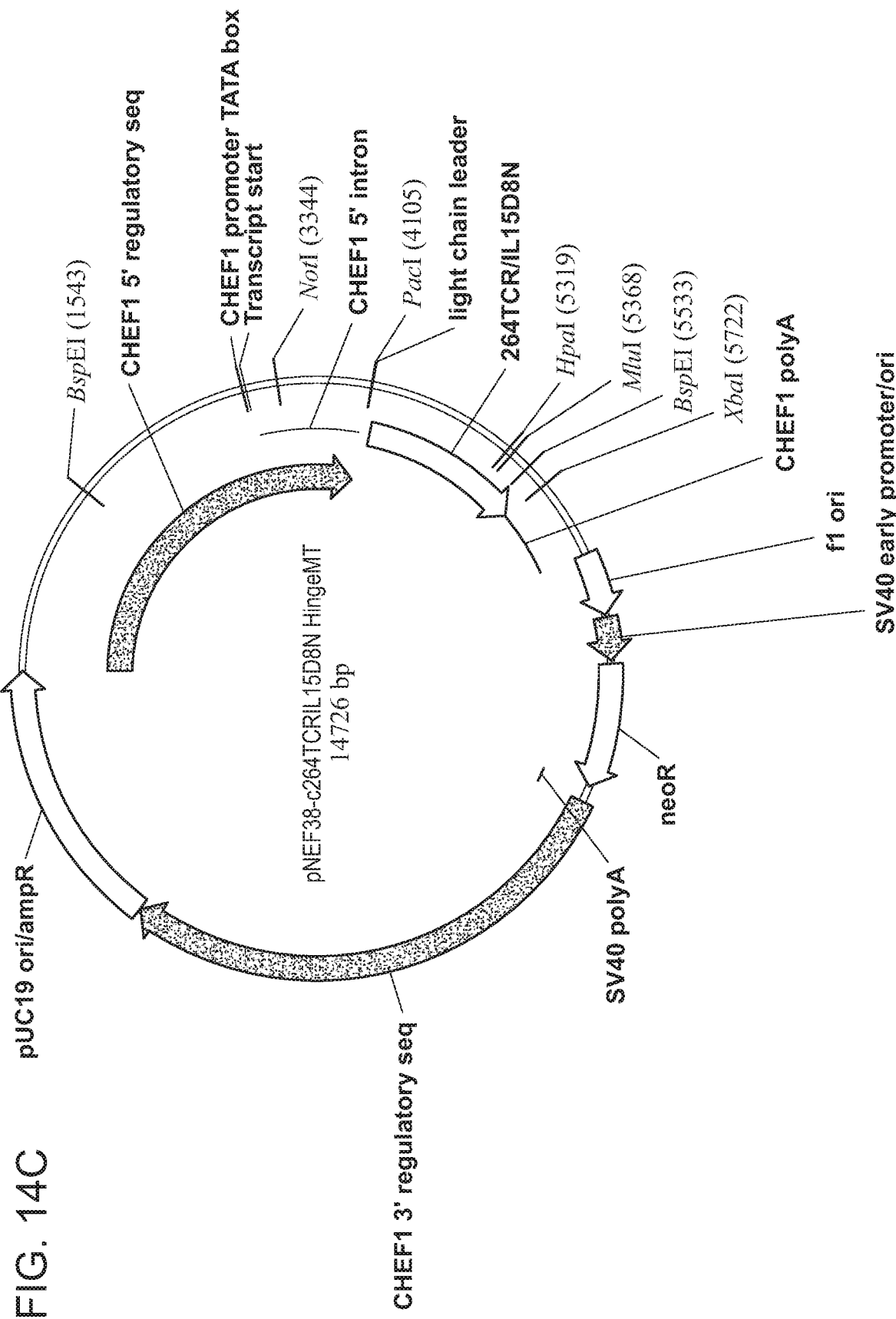

```
                                       (SEQ ID NO: 40)
5'-TGGTGGTCTAGATTATCAAGAAGTGTTGATG-3'
``` by PfuUltra (Stratagene) under following PCR conditions: 94 C, 1 min; 64 C, 1.5 min; 69 C 1.5 min; ×30 cycles; 72 C, 10 min. The huIL-15 mutant PCR-cDNA products were separated by electrophoresis on a 1% agarose gel and isolated. The cDNA product was purified from agarose with a Qiaquick Gel Extraction Kit (Qiagen). The huIL15 mutant gene was digested with MluI and XbaI and ligated into pNEF38-c264scTCR-hmt which had been digested with MluI and XbaI. The clone containing the huIL15 gene at position 8 with a substitution of alanine or asparagine was verified by DNA sequencing with GenomeLab Dye Termination Cycle Sequencing with a QUICK START KIT (Beckman Coulter) according to the manufacturer's protocol. The pNEF38-c264scTCR expression vector is described above. Cloning of the DNA fragment encoding mutated human IL-15 protein into the pNEF38-c264scTCR vector resulted in a c264scTCR-hmt-huIL15D8A or c264scTCR-hmt-huIL15D8N fusion gene comprising the following sequence: 3'-immunoglobulin light chain leader—264 TCR V-α—peptide linker—264 TCR V-β—human TCR C-β—mutated human IgG1 hinge-human IL15D8A or -human IL15D8N. The resulting vector (pNEF38-c264scTCR-hmt-huIL15D8A or pNEF38-c264scTCR-hmt-huIL15D8N), shown in FIG. 14B and FIG. 14C, was confirmed by DNA sequencing. The sequences of the pNEF38-c264scTCR-hmt-huIL15D8A or pNEF38-c264scTCR-hmt-huIL15D8N fusion gene and protein (including the leader sequence) are shown at FIG. 14D and FIG. 14E and at FIG. 14F and FIG. 14G, respectively.

Other mutations were introduced in a similar fashion and expression vector constructed as described above. The expression vectors were introduced into CHO.K1 cells to generated stable transfectants as described in Example 9. Production and purification of the TCR/IL15 fusion proteins and fusion protein complexes comprising IL-15 variants was carried out using similar methods as described in Examples 10 and 11. Generation of IL-15 variants as soluble cytokines can be carried out through a variety of methods known in the art, including production in prokaryotic and eukaryotic expression systems (see for example, WO9527722; Hsu et al. 2005 *J. Immunol.* 175:7226).

Figure 15:
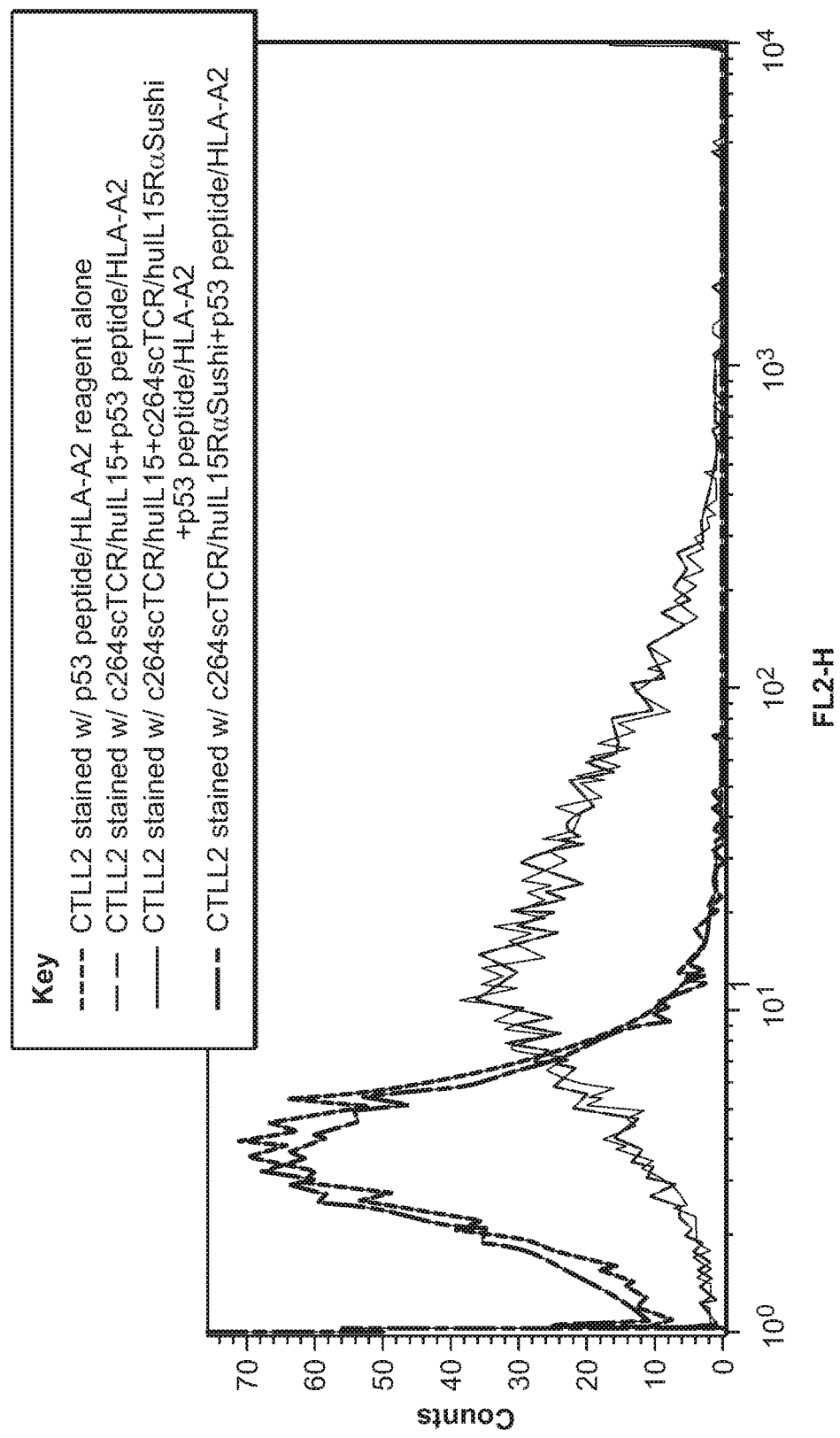
FIG. 15 is a graph showing flow cytometric analysis of IL-15R-bearing CTLL2 cells stained with fusion proteins and complexes following by TCR-specific peptide/MHC reagent.

Example 14—Functional Characterization of the TCR/IL15 and TCR/IL15Rα Fusion Proteins and Fusion Protein Complexes Functional binding of the fusion protein TCR domain was demonstrated based on the ELISA and cell staining methods using p53 (aa264-272)/HLA-A2.1 reagents described in Example 9 and the antigen presenting cell staining methods described in Example 12. The ability of the fusion protein IL15 and IL15Rα domains to interact was demonstrated as described in Example 11. Further the functional activity of the IL15 and IL15Rα domains can be assessed through a variety of methods including binding to IL-2/15Rβγc receptors or modulation of the activity of immune cells bearing IL-15 receptors. In one example, CTLL-2 cells, which express the heterotrimeric IL-15R (αβγc chains), were incubated with 0.5 µg of the individual fusion proteins: c264scTCR/huIL15, 264scTCR/huIL15RαSushi, or c264scTCR/huIL15+c264scTCR/huIL15RαSushi complex for 30 min at RT. Cells were washed once with washing buffer (PBS containing 0.5% BSA and 0.05% sodium azide) and stained with 0.5 µg of R-Phycoerythrin (PE) conjugated p53 (aa264-272)/HLA-A2 tetramer for 30 min at RT. Cells were washed and resuspended for analysis by flow cytometry. As shown in FIG. 15, association of the c264scTCR/huIL15 fusion protein and c264scTCR/huIL15+c264scTCR/huIL15RαSushi complex via their huIL15 domains with the IL-15 receptors on CTLL-2 cells can be detected with PE-conjugated p53 (aa264-272)/HLA-A2 tetramer recognizing the c264scTCR domain of the bound fusion protein. These results indicate that both the IL-15 and TCR domains of the fusion protein/fusion protein complexes are capable of functionally interacting with their cognate ligands.

Figure 16:
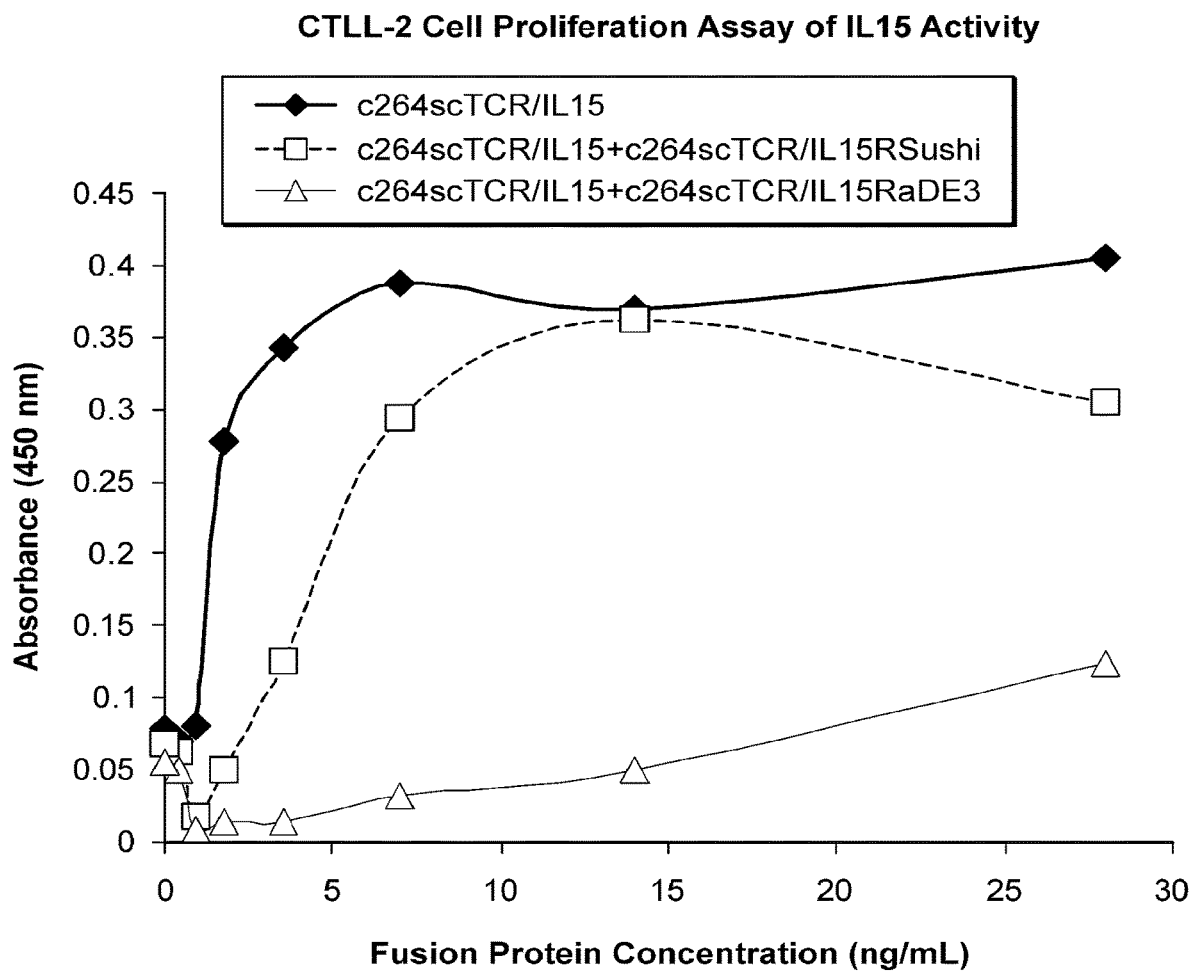
FIG. 16 depicts CTTL-2 cell proliferation assays of IL15 activity for dimeric fusion protein complexes of TCR/IL15RαSushi and TCR/IL15, comprising native and variant forms of IL15, to cognate peptide/MHC complexes displayed on cells loaded with peptide, as determined by flow cytometry.

In addition, CTLL-2 cells are dependent upon cytokines for growth and can respond to recombinant human IL-15. A cell-based WST-1 proliferation assay using CTLL-2 cells was developed to assess the IL-15 biological activity of fusion proteins and fusion protein complexes. WST-1 (Roche) is a reagent that can be converted into formazan by dehydrogenase enzymes found in metabolically active cells. In the WST-1 assay, the quantity of formazan in the culture media measured by the amount of 440-450 nm absorbance is directly proportional to the number of living cells in culture. CTLL-2 cells ($2 \times 10^4$/200 μL) were incubated with the indicated concentrations of fusion proteins (0-28 ng/mL): c264scTCR/huIL15, c264scTCR/huIL15+ c264scTCR/huIL15RαSushi complex or c264scTCR/ huIL15+c264scTCR/huIL15RαΔE3 complex for 3 days in 96-well plates at 37 C in a $CO_2$ incubator. Cells were incubated with 10 μL of WST-1 for 4 hours before harvesting 100 μL of culture medium for 440-450 nm absorbance measurement with a microtiter plate reader. As shown in FIG. 16, c264scTCR/huIL15 fusion protein can support the proliferation of CTLL-2 cells at a concentration as low as 1.8 ng/mL (~31.25 pM), suggesting activation of CTLL-2 cells with c264scTCR/huIL15 fusion protein via the high affinity IL15 receptor. Interestingly, fusion protein complexes also supported CTLL-2 cell proliferation but to a lesser degree suggesting that c264scTCR/huIL15 stimulatory activity was inhibited following complex formation with c264scTCR/huIL15RαSushi or c264scTCR/ huIL15RαΔE3 (by one fold or four fold, respectively). This suggests the binding of c264scTCR/huIL15 to the high affinity IL15 receptor is inhibited by c264scTCR/ huIL15RαSushi or c264scTCR/huIL15RαΔF3 fusion proteins. These results provide evidence that the fusion proteins and fusion protein complexes can activate or suppress responses of immune cells under different conditions.

Similar assays were performed with cell lines expressing only the intermediate affinity IL-15βγ$_c$ receptors, such as 32D13 cell lines (see below). In some cases, it is possible that the biological activity of IL15 in stimulating proliferation of the IL-15R-bearing cells will be enhanced when it is in a complex with the IL15Rα domain (Mortier, E. et al., 2006, *J. Biol. Chem.*, 281: 1612-1619; Stoklasek, T. et al., 2006, *J Immunol* 177: 6072-6080; Rubinstein, M. P. et al., 2006, *Proc Natl Acad Sci USA* 103: 9166-9171). Stimulation of cell proliferation by the c264scTCR/huIL15+c264scTCR/ huIL15RαSushi or c264scTCR/huIL15+c264scTCR/ huIL15RαΔE3 complexes will be assessed and may provide additional evidence that the fusion protein complexes can stimulate or activate immune responses of immune cells.

Figure 17A:
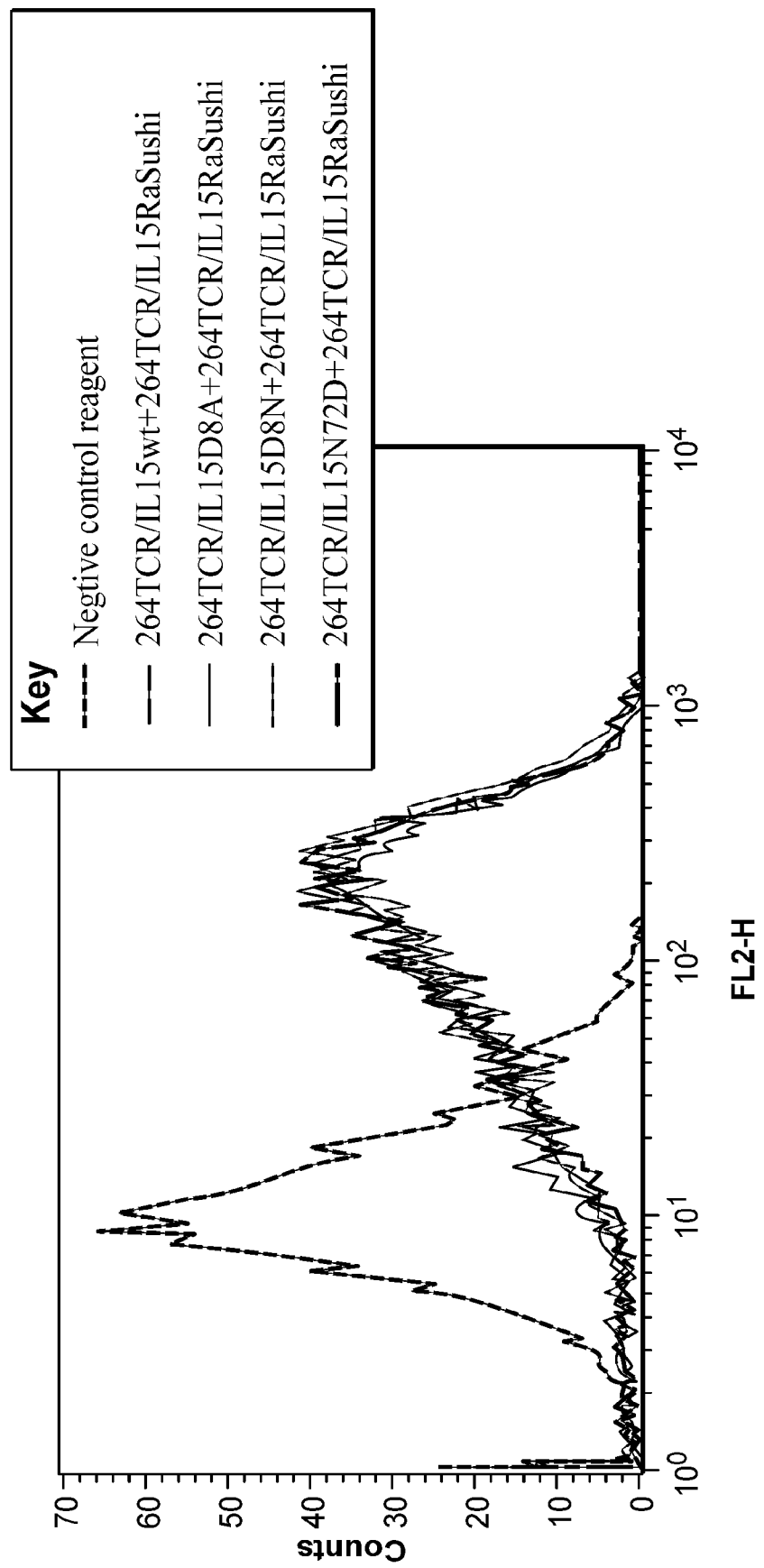
FIG. 17A, FIG. 17B, and FIG. 17C are graphs showing the binding of dimeric fusion protein complexes of TCR/IL15RαSushi and TCR/IL15, comprising native and variant forms of IL15, to cognate peptide/MHC complexes displayed on cells loaded with peptide, as determined by flow cytometry. Background binding of the dimeric fusion proteins complexes on cells with no loaded peptide is also shown.
Figure 17B:
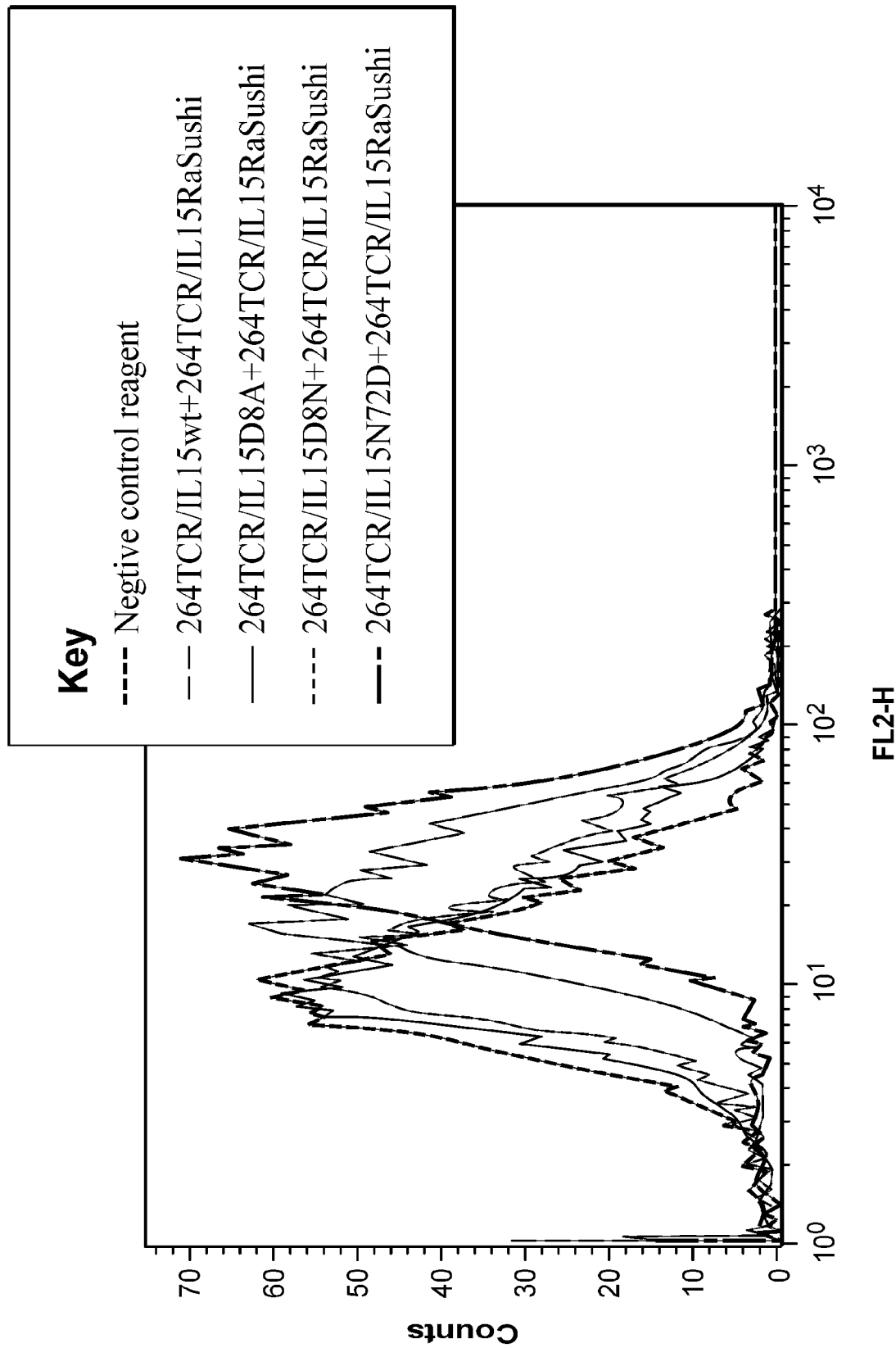
Figure 17C:
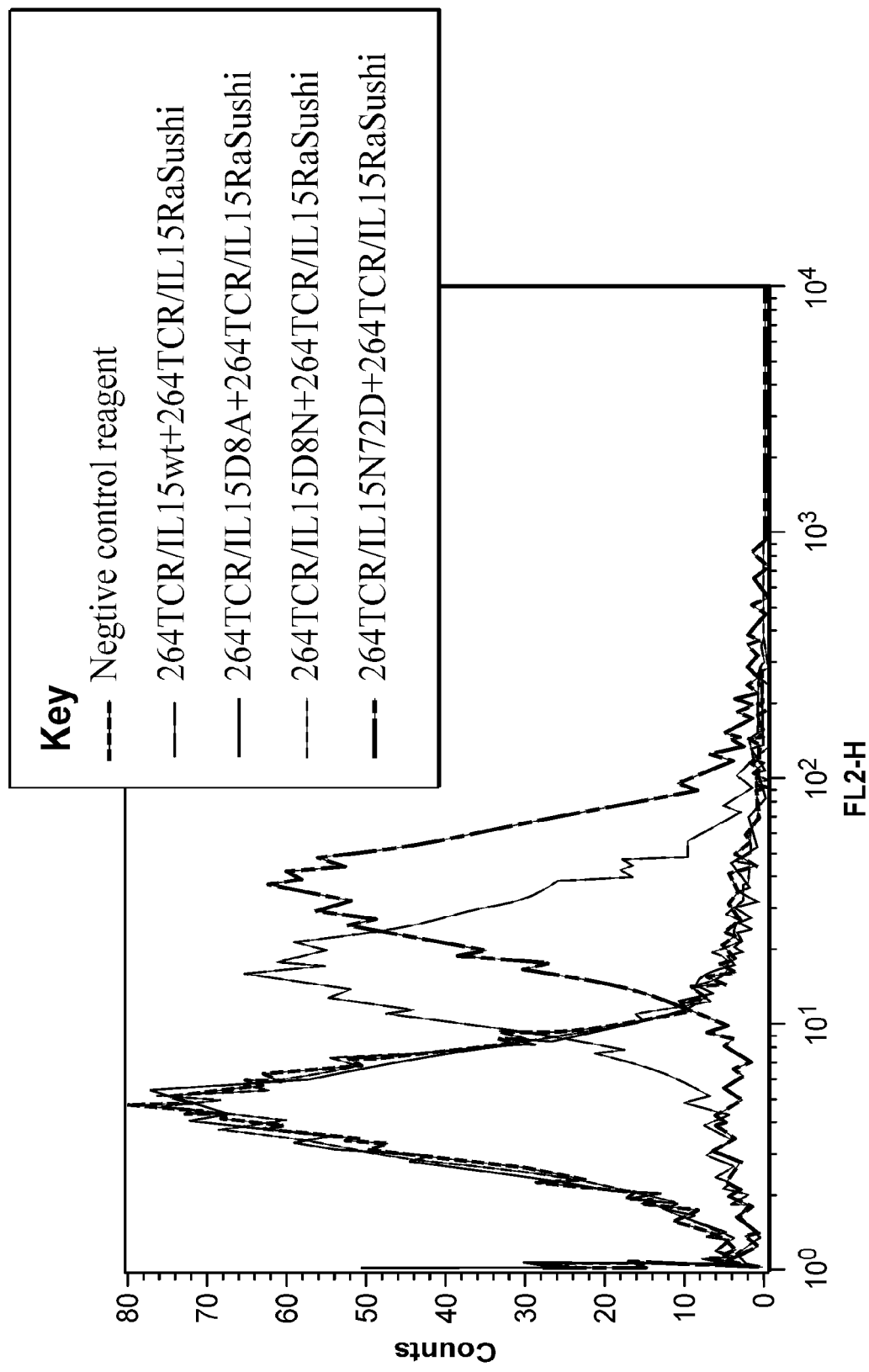

Example 15—Dimeric Fusion Protein Complexes of the TCR/IL15RαSushi and TCR/IL15 Variants Exhibit TCR-Specific Binding to Peptide/MHC Complex but Less Binding to the IL-15Rβγ$_C$ Receptors The fusion protein complexes comprising IL-15 variants as described above were characterized for their ability to bind the TCR-specific antigen, p53 (aa264-272)/HLA-A2.1. To generate cells presenting p53 (aa264-272)/HLA-A2.1, HLA-A2.1-positive T2 cells ($2 \times 10^6$/mL) were loaded with 20 μM p53 (aa264-272) peptide at 37 C in the presence of 1×PLE (Altor Bioscience) for 2-3 hrs. T2 cells that were not incubated with peptide and 32D13 cells expressing IL-2/ 15Rγ$_C$ serve as controls. The p53 peptide-loaded T2 cells, control T2 cells, or 32D13 cells ($2 \times 10^{5/100}$ μL) were then incubated for 30 min at 4 C with 320 nM of following dimeric fusion protein complexes: 1) c264scTCR/huIL15+ c264scTCR/huIL15RαSushi, 2) c264scTCR/huIL15D8A+ c264scTCR/huIL15RαSushi, and 3) c264scTCR/ huIL15D8N+c264scTCR/huIL15RαSushi. These complexes were generated by incubating 160 nM of purified c264scTCRhuIL15 fusion protein and 160 nM of purified c264scTCRhuIL15RαSushi fusion protein at 4 C for 3 hours: Following staining, cells were washed once with washing buffer (PBS containing 0.5% BSA and 0.05% sodium azide) and stained with 0.5 μg of biotinylated mouse monoclonal anti-human TCR Cβ antibody (BF1) in 100 μL of washing buffer for 30 min at 4 C. Cells were washed once and stained with 0.5 μg of R-Phycoerythrin conjugated streptavidin in 100 μL of washing buffer for 30 min at 4 C. Cells were washed and resuspended for analysis by flow cytometry. As shown in FIG. 17A, the c264scTCR/ huIL15D8A+c264scTCR/huIL15RαSushi complex and c264scTCR/huIL15D8N+c264scTCR/huIL15RαSushi complex exhibited equivalent activity as the c264scTCR/ huIL15+c264scTCR/huIL15RαSushi complex for specifically staining p53 peptide-loaded T2 cells. These results indicate that the multivalent scTCR domains are fully functional in each of these fusion complexes. However, as shown in FIG. 17B and FIG. 17C, the mutant c264scTCR/huIL15 fusion protein complexes showed less background staining on control T2 cells (FIG. 17B) and IL-15Rβγ$_c$-positive 32Dβ cells (FIG. 17C) than the wide type c264scTCR/IL15 fusion protein complex. Thus these fusion protein complexes comprising IL-15 variants (D8A and D8N) do not show binding activity to the IL-15Rβγ$_c$ receptors present on the 32D13 cells. Similar studies of IL-15Rβγ$_c$ receptor binding were carried out with other fusion proteins comprising IL-15 variants and are summarized in Table 1. The results indicate that fusion proteins and fusion protein complexes of the invention comprising IL-15 variants retain activity to recognize peptide/MHC complexes and exhibit decreased or increased binding activity for IL-15Rβγ$_c$ receptors.

Figure 18A:
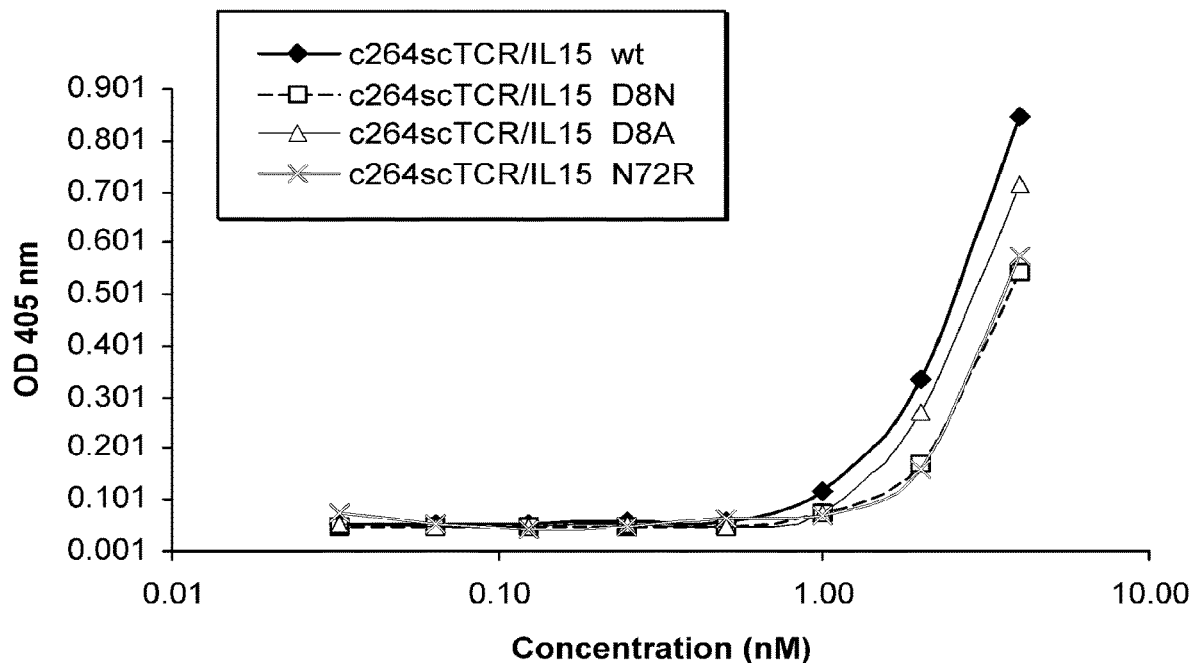
FIG. 18A and FIG. 18B are graphs showing binding activities of wide type, antagonist, and agonist TCR/IL15 fusion proteins to cognate peptide/MHC complexes and IL15Rα as determined by ELISA.
Figure 18B:
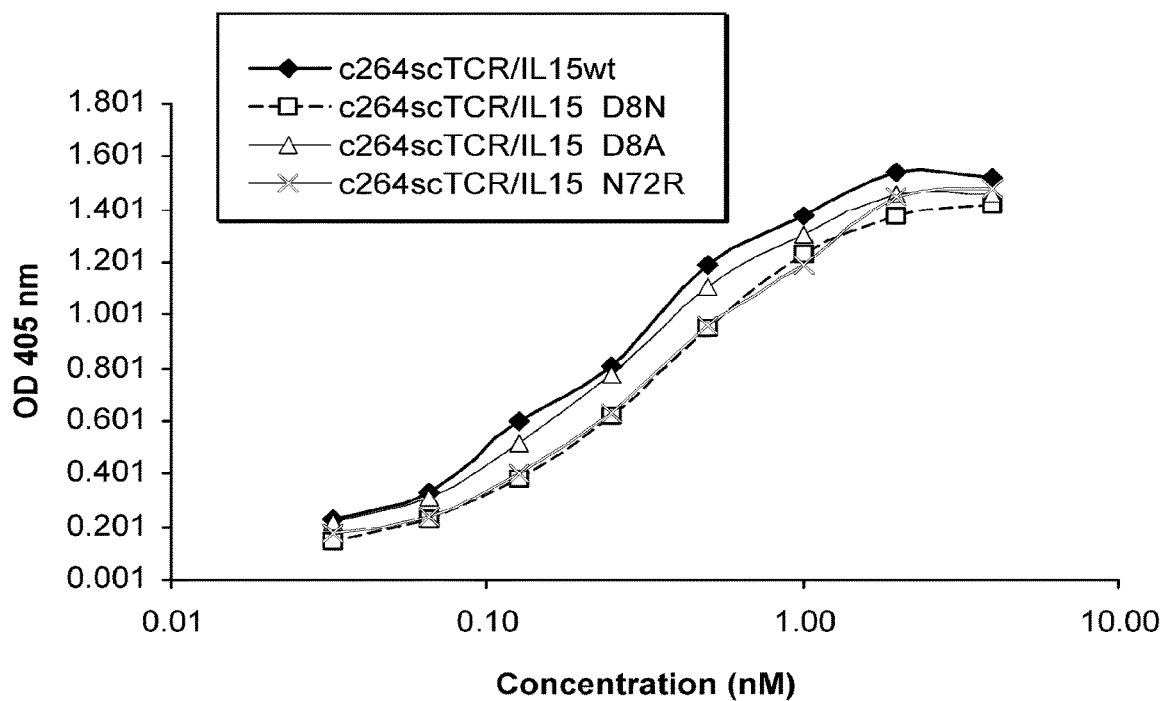

To confirm the above fusion proteins functional TCR and IL-15 domains, peptide/MHC and IL-15Rα binding activity was measured by ELISA analysis. The 96-well microtiter plates were precoated with 20 nM BF1, an anti-TCR Cβ antibody, or 20 nM TCR/IL15RαSushi in carbonated buffer pH 9.1 (sodium bicarbonate 35 mM, $Na_2CO_3$, 17.5 mM, NaCl 50 mM) over 3 hours at 4 C. Plates were washed with washing buffer (Imidazole 40 mM, NaCl 150 mM) for 4 times and blocked with 1% BSA-PBS for 10 minutes. The indicated fusion proteins at a concentration of 0.03-4 nM were added to the plates and incubated at RT for 30 minutes. The plates were washed four times. The BF1 captured fusion proteins were incubated with 1 μg/mL of HRP-conjugated p53/HLA-A2.1 tetramer for 45 minutes at RT and the TCR/IL15RaSushi captured fusion proteins were incubated with 50 ng/mL of biotinylate mouse anti-human IL-15 for 30 minutes at RT. After washing for 4 times, the plate incubated with biotinylate mouse anti-human IL-15 was incubated with 0.25 μg/mL of HRP-streptavidin for 15 minutes. The plates were washed 4 times and incubated with peroxidase substrate ABT for 1-10 minutes and developed for 405 nm absorbance measurement with a microtiter plate reader. As shown at FIG. 18A and FIG. 18B, the fusion proteins shared similar TCR-specific binding activity for p53/HLA-A2 tetramer and equivalent IL-15 binding activity for IL15RαSushi. Similar studies of IL-15Rα binding were carried out with other fusion proteins comprising IL-15 variants and are summarized in Table 1. The results indicate that fusion proteins and fusion protein complexes of the invention comprising IL-15 variants retain activity to recognize peptide/MHC complexes and IL-15Rα receptors.

Figure 19B:
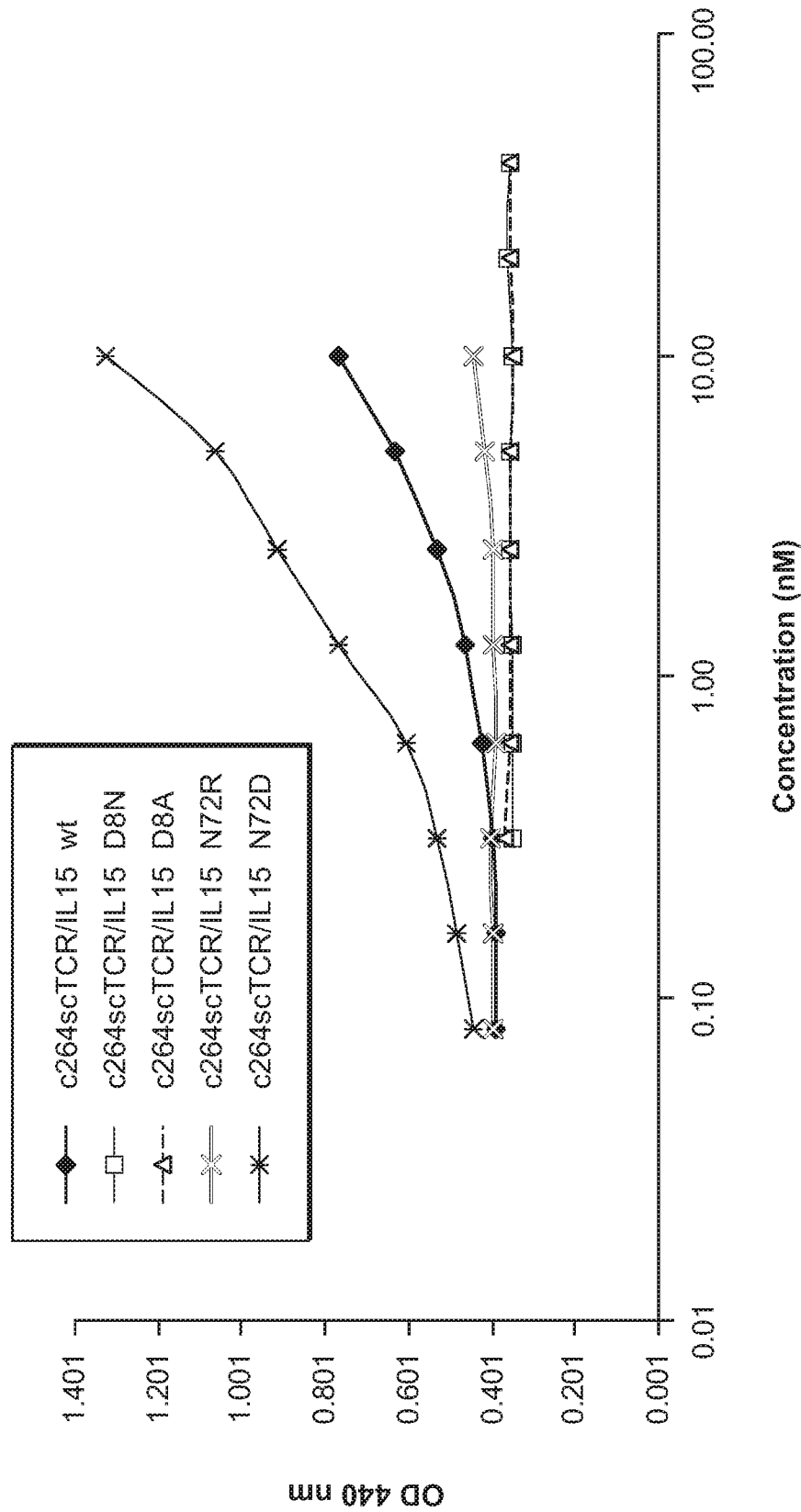

Example 16—Functional Characterization of the TCR/IL15 Mutant Fusion Proteins and Fusion Protein Complexes As indicated above, fusion proteins comprising an IL-15 antagonist or agonist may be a useful as a targeted agents for inhibiting or stimulating IL-15-mediated responses (i.e., T cell or NK cell activity) at the disease site. To determine the IL-15 bioactivity of these fusion proteins to effect immune responses, cell proliferation studies were carried out with CTLL-2 cells expressing the high affinity IL-15R ($\alpha\beta\gamma_c$ chains) and with 32D13 cells expressing the intermediate IL-15R ($\beta\gamma_c$ chains). The cells ($2\times10^4$/200 µL) were incubated with 0.4-40 nM of the above described TCR/IL15 fusion proteins for 3 days in 96-well plates at 37 C in a $CO_2$ incubator. Cells were incubated with 10 µL of WST-1 for 4 hours before harvesting 150 µL of culture medium for 440 nm absorbance measurement with a microtiter plate reader. As shown in FIG. 19A and FIG. 19B, the c264scTCR/huIL15 fusion protein comprising the wild type IL-15 domain can support the proliferation of CTLL-2 and 32D13 cells at a concentration as low as 40 pM or 1 nM respectively. Interestingly, the fusion protein comprising an IL15 variant with an asparagine to aspartic acid substitution at position 72 with an amino acid (c264scTCR/huIL15N72D) was much more active that the fusion protein comprising the wild type IL-15 domain at supporting the proliferation of 32Dβ cell line, showing biological activity at a concentration as low as 80 pM (FIG. 19B). In this respect the fusion protein comprising IL-15 variant (huIL15N72D) showed super agonist activity. In a complex with c264scTCR/IL15RαSushi at one to one ratio, the c264scTCR/huIL15N72D had similar binding ability as c264scTCR/huIL15 wt to p53/HLA-A2.1 complex on T2 cells (FIG. 17A) but exhibited increased binding ability to IL-15Rβ$\gamma_c$ receptors on 32D13 cells (FIG. 17C). In contrast, the fusion proteins comprising IL-15 variants with substitutions at position 8 (c264scTCR/huIL15D8N or c264scTCR/huIL15D8A), position 65 (c264scTCR/huIL15N65A), position 108 (c264scTCR/huIL15Q108A), or a different substitution at position 72 (c264scTCR/huIL15N72R) were less active in supporting proliferation of both CTLL-2 and 32D13 cells compared to c264scTCR/huIL15 wt fusion protein (FIG. 19A and FIG. 19B). Similar studies of IL-15-dependent proliferative activity were carried out with other fusion proteins comprising IL-15 variants and are summarized in Table 1. The data support the hypothesis that mutations at positions 8, 61, 65, 72 and 108 of the IL-15 protein can result in IL-15 antagonists with decreased binding to IL-15R and little or no activity to stimulate immune responses. The results with the position 72 substitutions are unexpected given that one mutant (c264scTCR/huIL15N72R) acted as an IL-15 antagonist whereas a different mutant (c264scTCR/huIL15N72D) showed increased binding to IL-15 R and enhanced activity at stimulate immune responses.

Figure 19C:
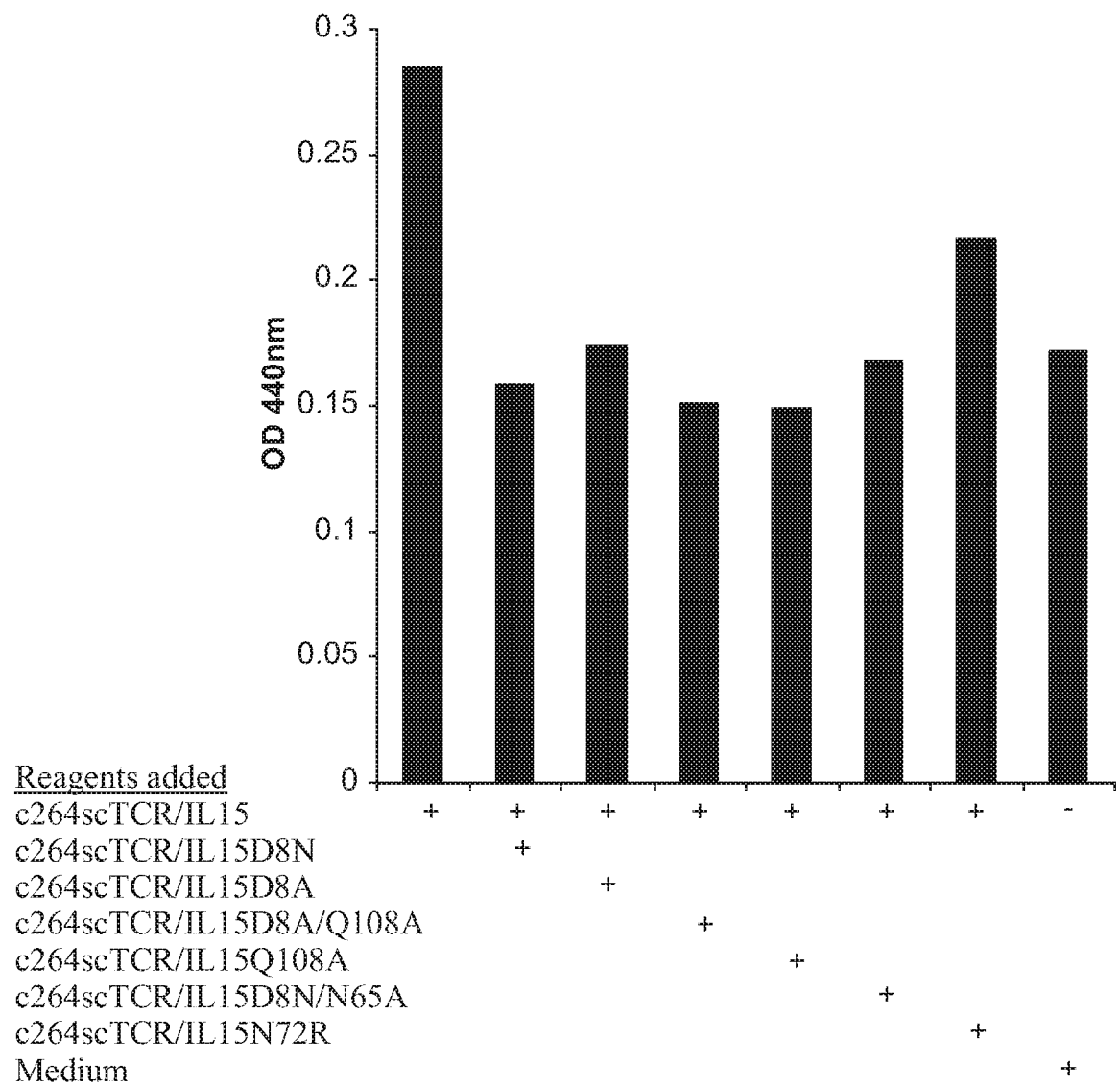

In a typical circumstance, IL-15 is trans-presented by IL15Rα on a dendritic cell surface to IL-15Rβ$\gamma_c$ receptors on memory T, NKT, or NK cell to support cell survival and stimulate immune responses. An antagonist should block the trans-presentation of IL-15 by binding IL15Rα. To evaluate if the antagonist fusion proteins can compete with c264scTCR/huIL15 wt to block its activity to support CTLL-2 cell growth, $4\times10^4$ CTLL-2 cells were incubated with 0.5 nM of c264scTCR/huIL15 wt in the presence or absence of 50 nM (100-fold molar excess) of various c264scTCR/huIL15 mutant fusion proteins at 37 C in a $CO_2$ incubator for 24 hours. Cells were incubated with 10 µL of WST-1 for 4 hours before harvesting 150 µL of culture medium for 440 nm absorbance measurement with a microtiter plate reader. As shown in FIG. 19C, the ability of c264scTCR/huIL15 wt to support proliferation of CTLL-2 cells was totally blocked in the presence of 100-fold more c264scTCR/huIL15D8N, c264scTCR/huIL15D8A, c264scTCR/huIL15D8A/Q108A, c264scTCR/huIL15Q108A, or c264scTCR/huIL15D8N/N65A, and was reduced 62% in the presence of c264scTCR/huIL15N72R fusion protein. It suggested that these fusion proteins were the antagonists to c264scTCR/IL15 fusion protein. This data indicates that c264scTCR/huIL15 mutant fusion proteins were functional antagonist of the IL-15 activity, as expected based on the ability of these proteins to bind IL-15Rα but not IL-15Rβ$\gamma_c$ receptors.

Similar studies will be carried out with the other TCR/IL15 fusion proteins and IL-15 variants described herein to demonstrate IL-15 antagonist and agonist activity. As summarized in Table 1, the substitutions at positions 8, 61, 65, 72, and 108 of IL-15 show the ability to affect the binding of IL-15 to IL-15R (($\beta\gamma_c$ chains). Other substitutions at positions 92, 101, and 111 of IL-15 will also be assessed as potential binding sites for IL-15R interaction. In addition, combinations of changes including substitutions at all or several of these residues may create the effective antagonists or agonists of IL-15. Including the molecules described above, IL-15 variants to be assessed include those with changes at position 8 to alanine, asparagine, serine, lysine, threonine, or tyrosine; position 61 to alanine, asparagine, serine, lysine, threonine, or tyrosine; position 65 to alanine, aspartic acid, or arginine; position 72 to alanine, aspartic acid, or arginine; and positions 92, 101, 108, or 111 to alanine or serine.

Example 17—Cell-Cell Conjugation and Immune Cell Retargeting by the TCR/IL15 and TCR/IL15Rα Fusion Proteins and Fusion Protein Complexes To demonstrate that the fusion proteins or fusion protein complexes can bridge IL-15 receptor-bearing cells with peptide/WIC bearing target cells, T2 cells will be loaded with either p53 (aa264-272) peptide or control CMVpp65 (aa495-503) peptide and then labeled with dihydroethidium. CTLL-2 cells will be labeled with calcein AM and the two labeled cell populations will be mixed and incubated in the presence or absence of the fusion proteins or fusion protein complexes. In the absence of the fusion protein complexes or when the T2 cells were loaded with control peptide, the cells are anticipated to remain as two distinct populations as assessed by flow cytometry. However, when the T2 cells are loaded with p53 (aa264-272) and incubated with the CTLL-2 cells in the presence of fusion proteins or complexes, the appearance of a double staining population of cells would be indicative of conjugation of T2 cells to CTLL-2 cells via the fusion proteins or fusion protein complexes.

Similarly, studies can be conducted to demonstrate that the fusion protein complexes can bridge IL-15 receptor-bearing immune cells with peptide/MHC bearing target cells and direct immune cytotoxicity against the target cells. For example, T2 cells will be loaded with either p53 (aa264-272) peptide or control CMVpp65 (aa495-503) peptide and then labeled with calcein AM. Immune effector cells bearing IL-15 receptors (i.e. activated NK cells or T cells) will be mixed at different ratios and incubated under appropriate conditions (i.e. 37 C for 2-4 hours) in the presence or absence of the fusion protein complex. Cytotoxicity will be assessed based on release of calcein from the T2 target cells into the culture media by standard methods. The specific release of calcein-AM will be measured or compared to the non-specific control of spontaneous released calcein-AM. In the absence of the fusion protein complex or when the T2 cells were loaded with control peptide, low levels of target cell cytotoxicity are expected. However, when the T2 cells are loaded with p53 (aa264-272) and incubated with the immune effector cells in the presence of fusion protein complex, specific lysis of the T2 cells would be an indication that the immune effector cells are retargeted against the p53 peptide-presenting cells via the fusion protein complex. Similar studies will be conducted with tumor cell lines presenting p53 (aa264-272)/HLA-A2.1 complexes as target cells.

Example 18—In Vivo Demonstration of Anti-Tumor Effects of IL-15 Variant Agonists, TCR/IL15 Fusion Proteins and Fusion Protein Complexes To determine if the fusion protein complexes or IL-15 variant agonists have anti-tumor activity in vivo, an experimental xenograft tumor model will be used. Human tumor cell lines expressing p53 (aa264-272)/HLA-A2.1 complexes, such as A375 melanoma, MDA-MB-231 mammary adenocarcinoma, PANC1 pancreatic carcinoma, have been employed in similar animal efficacy studies using other TCR-based fusion proteins (5-7). For example, A375 human melanoma cells will be injected subcutaneously into the flank of nude mice and tumors will be allowed to establish for three days. Tumor bearing mice will be injected intravenously with c264scTCR/huIL15+c264scTCR/huIL15RαSushi complex or an IL-15 variant agonist (dose range—0.1 to 2 mg/kg), or the dose volume equivalent of PBS daily for four or more days. During the study, tumor size will measured and the tumor volumes will be calculated. All mice treated with PBS are expected to develop tumors. Suppression of tumor growth or complete tumor regression in some or all the mice treated with the fusion protein complex or IL-15 variant agonist would be an indication of an antitumor effect of the treatment. Alternative dosing schedules including multi-cycle dosing may also demonstrate the antitumor efficacy of the fusion protein or IL-15 variant agonist. Tumor cell lines lacking p53 (aa264-272)/HLA-A2.1 complexes (such as HT-29 or AsPC-1 (5,9) can be used as controls for antigen specific recognition by the c264scTCR-domain of the fusion protein complex. Alternative fusion protein complexes comprising other TCR domains (i.e. specific to CMVpp65 (aa495-503) peptide (9) could be used as non-tumor targeting controls.

In addition, adoptive cell transfer studies will be carried out in xenograft tumor bearing mice. For example, immune cells bearing the IL-15 receptor, such as naïve or activated (or memory) splenocytes, NK cell or T cells, will be isolated from mice and incubated with c264scTCR/huIL15+c264scTCR/huIL15RαSushi complex or an agonist IL-15 variant under conditions permitting binding to the cells. In some cases the fusion protein complex or an agonist IL-15 variant will be used to activate the immune cells. The IL-15 variant activated cells or fusion protein complex-coated cells will then be transferred into nude mice bearing A375 tumors. Controls will include transfer of the untreated immune cells, the fusion protein complex alone and PBS. Tumor growth will be monitored and all mice treated with PBS are expected to develop tumors. Suppression of tumor growth or complete tumor regression in some or all the mice treated with the IL-15 variant activated cells or fusion protein complex-coated cells would be an indication of an antitumor effect of the treatment. Alternatively, the IL-15 variant or fusion protein complex and immune cells will be administered at the same time, or separately at the same or different times. The immune cells may be autologous or allogeneic in relation with the tumor-bearing host. The number of cells transferred and dosing schedule will be varied to assess and optimize antitumor efficacy. As described above, other tumor lines or fusion protein complexes will be employed to determine the role of antigen targeting in any observed antitumor activity.

Example 19—In Vitro Treatment of Immune Cells with TCR/IL15:TCR/IL15Rα Fusion Protein Complexes Followed by Adoptive Cell Transfer Provide Improved Survival in Xenograft Tumor Animal Model To demonstrate the anti-tumor efficacy of enriched allogenic mouse NK cells preincubated with TCR/IL15:TCR/IL15Rα fusion protein complexes on tumor growth, the following study was carried out using human NSCLC A549A2 tumor cells in an experimental metastasis model in nude mice.

Athymic nude mice (n=4 per group, female, 5-6 week old) were intravenously (IV) injected through the lateral tail vein with the human NSCLC tumor cell line A549-A2 at $5 \times 10^6$ cells/mouse. The A549-A2 cell line represents a transfectant of the p53-positive A549 parental line carrying a vector expressing human HLA-A2.1 cDNA.

Spleens from A2 mice (B6 background) were collected and NK cells were isolated using a NK cell isolation kit from Miltenyi Biotech, Inc. according to the manufacturer's instruction. Briefly, a single cell suspension of splenocytes was prepared by homogenizing the spleens through a metal screen (60 mesh) in HBSS. Red blood cells were lysed in ACK red blood lysing buffer. Cells will be incubated with biotin-antibody cocktail (10 μL for $10^7$ cells) for 10 min at 4-8 C. The number of leukocytes was determined and 30 μL of buffer (PBS pH 7.2, 0.5% BSA and 2 mM EDTA) and 20 μL of anti-biotin MicroBeads per $10^7$ cells was added and the mixture was incubated at 4-8 C for 15 min. The cells were washed in 2 mL buffer and centrifuge at 300×g for 10 min. The cells were resuspended in 500 μL of buffer for loading to the MACS column. The flow through was collected and the purity of the NK cells was determined using FACScan analysis.

In order to activate the cells, NK cells ($5 \times 10^6$) were cultured at 37 C overnight in the presence or absence of c264scTCR/IL15: c264scTCR/IL15Rα fusion protein complex, TCR-IL2 fusion protein or rhIL-2 in T25 flasks in 10 ml RPMI1640 supplemented with 10% FBS. c264scTCR/IL15: c264scTCR/IL15Rα fusion protein complex and TCR-IL2 fusion protein was added at a concentration of 0.8 μg/mL and rhIL-2 was added at 0.2 μg/mL. After overnight incubation, cells were harvested and preincubated in 0.5 mg/mL c264scTCR/IL15: c264scTCR/IL15Rα fusion protein complex or TCR-IL2 fusion protein or 0.125 mg/mL rhIL-2 in 100 μL on ice for 30 min. After wash in PBS (1 mL), cells were resuspended in PBS at $10 \times 10^6$/mL for adoptive transfer.

On day 1, mice were injected i.v. via the tail vein with A549A2 tumor cells ($5 \times 10^6$) to establish pulmonary tumors. Fourteen days post tumor cell injection, mice were randomized and divided into 5 groups (n=4). Mice were treated with cyclophosphamide (CTX) via intraperitoneal injection at a dose of 200 mg/kg on days 14 and 21. NK cells ($1\times10^6$/mouse) preincubated with different fusion proteins or rhIL-2 were injected i.v. on days 16 and 22, and mice receiving PBS served as controls. A summary of the treatment schedule is a follows:

| | CTX | | NK cells | |
|---|---|---|---|---|
| Group | Dose (mg/kg) | Injection (ip) | Dose ($\times10^6$) | Injection (iv) |
| CTX | 200 | Days 14, 21 | 0 | Days 16, 22 |
| CTX + NK/rhIL2 | 200 | Days 14, 21 | 1 | Days 16, 22 |
| CTX + NK/MART-1scTCR-IL2 | 200 | Days 14, 21 | 1 | Days 16, 22 |
| CTX + NK/c264scTCR-IL2 | 200 | Days 14, 21 | 1 | Days 16, 22 |
| CTX + NK/c264scTCR/IL15: c264scTCR/IL15Rα fusion protein complex | 200 | Days 14, 21 | 1 | Days 16, 22 |

Survival of tumor-bearing mice was monitored every day. Mice that became moribund were sacrificed and counted as dead. Mice surviving longer than 100 days post-tumor injection were considered as cured.

Median survivals for mice in the CTX, CTX+NK/rhIL-2, CTX+NK/MART1scTCR-IL2, CTX+NK/c264scTCR-IL2 and c264scTCR/IL15: c264scTCR/IL15Rα fusion protein complex treatment groups are 52, 67.5, 64.5, 85.5, and 80 days, respectively (FIG. 20). Thus, adoptive transfer of c264scTCR/IL15: c264scTCR/IL15Rα-activated NK cells resulted a longer median survival time than observed in tumor-bearing animals treated with chemotherapy alone or with NK cells activated by the non-targeted MARTscTCR-IL2 or rhIL-2. The results from this pilot experiment indicate that activation and targeting mouse NK cells with c264scTCR/IL15: c264scTCR/IL15Rα may provide enhanced antitumor activity.

Example 20—Enhanced Binding of TCR/IL15:TCR/IL15Rα Fusion Protein Complexes to IL-15R Bearing Immune Cells as Evidenced by an Extended Cell Surface Residency Time The cell surface residency time of the fusion protein complexes on the IL-15R-bearing cells may influence the ability of the fusion protein to target or bridge effector cells with the TCR-specific tumor cells. To investigate this, binding of the scTCR/IL-15 fusion proteins, TCR/IL15: TCR/IL15Rα fusion protein complexes and recombinant IL-15 to IL-15RαβγC receptor-bearing CTLL-2 cells and IL-15RβγC receptor-bearing CTLL-2 cells 32D13 cells will be directly compared by flow cytometry. Following incubation with the various proteins, cells will be washed and incubated in media at 37° C. for up to 180 min and the level of proteins remaining on the cell surface was detected with PE-labeled anti-IL-15 mAb. Comparisons between the initial time zero staining and subsequent times will allow determination of the cell surface residency time for each proteins binding to IL-15R. Increased cell surface residency time of the scTCR/IL-15 fusion proteins or TCR/IL15:TCR/IL15Rα fusion protein complexes compared to IL-15 would be an indication of enhanced and more stable receptor binding activity.

Example 21—Increased In Vivo Half Life of TCR/IL15 Fusion Proteins and TCR/IL15:TCR/IL15Rα Fusion Protein Complexes Compared to IL-15 in Mice The pharmacokinetic parameters of c264scTCR/IL-15, c264scTCR/IL15: c264scTCR/IL15Rα complex, recombinant IL-15 or soluble IL-15:IL-15Rα complex will be evaluated in the HLA-A2.1/Kb-transgenic mouse strain. The presence of the HLA-A2.1 domain, for which c264scTCR/IL-2 is restricted, may influence the pharmacokinetics of this fusion protein and should give a more relevant "humanized" view of the pharmacokinetics than other mouse strains. Mice will be injected intravenous with molar equivalent amounts of c264scTCR/IL-15, c264scTCR/IL15: c264scTCR/IL15Rα complex, recombinant IL-15 or soluble IL-15:IL-15Rα complex and blood will be collected at various time points from 5 minutes to two weeks post injection. Serum concentrations of the fusion proteins will be evaluated using ELISA formats, disclosed above. Concentrations of IL-15 were detected with a standard IL-15-specific ELISA.

The in vivo pharmacokinetic parameters of c264scTCR/IL-15, c264scTCR/IL15: c264scTCR/IL15Rα complex, recombinant IL-15 or soluble IL-15:IL-15Rα complex will be determined using curve fitting software (e.g., WinNonlin). Elevated Cmax values, increased serum half life or decreased clearance for the c264scTCR/IL-15 or c264scTCR/IL15: c264scTCR/IL15Rα complex compared to recombinant IL-15 or soluble IL-15:IL-15Rα complex would be an indication that generation of the TCR-IL15 fusion or TCR/IL15:TCR/IL-15Rα complex provides more favorable pharmacokinetics that is observed with IL-15 alone.

Example 22—In Vivo Demonstration of Immunosuppressive Effects of IL-15 Variant Antagonists, TCR/IL15 Fusion Proteins and Fusion Protein Complexes To determine if the fusion protein complexes or IL-15 variant antagonists have immuno-suppressive activity in vivo, an experimental autoimmune arthritis model will be used. It has been demonstrated that autoimmune arthritis can be induced following administration of type II collagen (CII) in HLA-DR4-transgenic mice (Rosloniec et al. 1998. *J Immunol.* 160:2573-8). Additionally, CII-specific T-cells involved in the pathology of this disease have been characterized. The TCR genes from these T-cells will be used to construct the appropriate expression vectors and host cell lines to generate CIIscTCR/IL15 comprising IL-15 variant antagonists and CIIscTCR/IL15RαSushi fusion proteins as described in previous examples. Following induction of arthritis by CII administration, the HLA-DR4-transgenic mice will be injected intravenously with CIIscTCR/IL15- antagonst+CIIscTCR/IL15RαSushi complex or an IL-15 variant antagonist (dose range—0.1 to 2 mg/kg), or the dose volume equivalent of PBS daily for four or more days. During the study, the mouse paw joints will be evaluated and scored for the degree of inflammation on a scale of 0 to 4. All mice treated with PBS are expected to develop arthritis. Suppression of arthritis (e.g. decreased incidence or clinical score) in some or all the mice treated with the fusion protein complex or IL-15 variant would be an indication of an immunosuppressive effect of the treatment. Alternative dosing schedules including multi-cycle dosing may also demonstrate the immunosuppressive efficacy of the fusion protein or IL-15 variant. Alternative fusion protein complexes comprising other TCR domains (i.e. specific to p53 peptide) could be used as non-disease targeting controls to demonstrate specificity of the targeted TCR fusion proteins ability to direct immunosuppressive activity to the disease site.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

1. Mortier, E., A. Quemener, P. Vusio, I. Lorenzen, Y. Boublik, J. Grotzinger, A. Plet, and Y. Jacques. 2006. Soluble interleukin-15 receptor alpha (IL-15R alpha)-sushi as a selective and potent agonist of IL-15 action through IL-15R beta/gamma. Hyperagonist IL-15×IL-15R alpha fusion proteins. *J Biol Chem* 281: 1612-1619.
2. Stoklasek, T. A., K. S. Schluns, and L. Lefrancois. 2006. Combined IL-15/IL-15Ralpha immunotherapy maximizes IL-15 activity in vivo. *J Immunol* 177: 6072-6080.
3. Rubinstein, M. P., M. Kovar, J. F. Purton, J. H. Cho, O. Boyman, C. D. Surh, and J. Sprent. 2006. Converting IL-15 to a superagonist by binding to soluble IL-15R{alpha}. *Proc Natl Acad Sci USA* 103: 9166-9171.
4. Waldmann, T. A. 2006. The biology of interleukin-2 and interleukin-15: implications for cancer therapy and vaccine design. *Nat Rev Immunol* 6: 595-601.
5. Belmont, H. J., S. Price-Schiavi, B. Liu, K. F. Card, H. I. Lee, K. P. Han, J. Wen, S. Tang, X. Zhu, J. Merrill, P. A. Chavillaz, J. L. Wong, P. R. Rhode, and H. C. Wong. 2006. Potent antitumor activity of a tumor-specific soluble TCR/IL-2 fusion protein. *Clin Immunol* 121: 29-39.
6. Card, K. F., S. A. Price-Schiavi, B. Liu, E. Thomson, E. Nieves, H. Belmont, J. Builes, J. A. Jiao, J. Hernandez, J. Weidanz, L. Sherman, J. L. Francis, A. Amirkhosravi, and H. C. Wong. 2004. A soluble single-chain T-cell receptor IL-2 fusion protein retains WIC-restricted peptide specificity and IL-2 bioactivity. *Cancer Immunol Immunother* 53: 345-357.
7. Mosquera, L. A., K. F. Card, S. A. Price-Schiavi, H. J. Belmont, B. Liu, J. Builes, X. Zhu, P. A. Chavaillaz, H. I. Lee, J. A. Jiao, J. L. Francis, A. Amirkhosravi, R. L. Wong, and H. C. Wong. 2005. In Vitro and In Vivo Characterization of a Novel Antibody-Like Single-Chain TCR Human IgG1 Fusion Protein. *J Immunol* 174: 4381-4388.
8. Penichet, M. L., E. T. Harvill, and S. L. Morrison. 1997. Antibody-IL-2 fusion proteins: a novel strategy for immune protection. *Hum Antibodies* 8: 106-118.
9. Zhu, X., H. J. Belmont, S. Price-Schiavi, B. Liu, H. I. Lee, M. Fernandez, R. L. Wong, J. Builes, P. R. Rhode, and H. C. Wong. 2006. Visualization of p53264-272/HLA-A*0201 Complexes Naturally Presented on Tumor Cell Surface by a Multimeric Soluble Single-Chain T Cell Receptor. *J Immunol* 176: 3223-3232.

What is claimed is:

1. A method of treatment for cancer or viral infection in a mammal in need thereof, the method comprising administering an effective amount of a soluble fusion protein complex comprising two soluble proteins, wherein the first soluble protein comprises:
- (a) a fusion protein comprising a first biologically active polypeptide covalently linked to an interleukin-15 (IL-15) polypeptide, or
- (b) an IL-15 polypeptide; and the second soluble protein comprises a fusion protein comprising:
- (c) a second biologically active polypeptide covalently linked to (d) an interleukin-15 receptor alpha (IL-15Ra) polypeptide;

wherein the first and/or second biologically active polypeptides comprise cytokines, chemokines, growth factors or receptor binding domains thereof;

wherein the IL-15 domain of the first soluble protein binds to the IL-15Ra domain of the second soluble protein to form the soluble fusion protein complex; and wherein the first biologically active polypeptide is different than an IL-15Ra polypeptide, and the second biologically active polypeptide is different than an IL-15 polypeptide.

2. The method of claim 1, wherein the first and/or second biologically active polypeptides comprises a cytokine or a binding partner thereof.

3. The method of claim 2, wherein the cytokine comprises TGF-beta (TGF-β), or a binding partner thereof.

4. The method of claim 1, wherein the first biologically active polypeptide is covalently linked to the IL-15 polypeptide by a polypeptide linker sequence.

5. The method of claim 1, wherein the second biologically active polypeptide is covalently linked to the IL-15Ra polypeptide by a polypeptide linker sequence.

6. The method of claim 1, wherein the IL-15Ra polypeptide comprises the extracellular domain of the IL-15 receptor alpha that binds the IL-15 polypeptide.

7. The method of claim 1, wherein the IL-15Ra polypeptide comprises either the IL-15a sushi domain or the IL-15Ra delta E3 (IL-15aΔE3) domain.

8. The method of claim 1 wherein the mammal is suffering from cancer and the administering treats cancer in the mammal.

9. The method of claim 1 wherein the mammal is suffering from a viral infection and the administering treats the viral infection in the mammal.

10. The method of claim 9, wherein the mammal is suffering from a human immunodeficiency virus (HIV) infection.

11. The method of claim 1, wherein at least one of the first and second biologically active polypeptides recognizes a disease-associated antigen.

12. The method of claim 11, wherein the disease-associated antigen is a peptide/MHC complex.

13. The method of claim 1, wherein at least one of the first and second biologically active polypeptides comprises an antibody or binding fragment thereof.

14. The method of claim 1, wherein the administering results in forming a specific binding complex between antigen-expressing diseased cells and IL-15R-expressing immune cells sufficient to localize the immune cells, and sufficiently damaging or killing the disease cells in order to prevent or treat the disease in the mammal.

15. The method of claim 1, wherein at least one of the first and second biologically active polypeptides increases the in vivo half-life of the soluble fusion protein complex.

16. The method of claim 1, wherein the soluble fusion protein complex is administered via oral, topical, nasal, or parenteral route.

17. The method of claim 1, wherein the soluble fusion protein complex is formulated as a pharmaceutical composition for administration to the mammal in need thereof.

* * * * *

SEQUENCE LISTING

```
Sequence total quantity: 40
SEQ ID NO: 1            moltype = AA  length = 114
FEATURE                 Location/Qualifiers
source                  1..114
                        mol_type = protein
                        organism = Homo sapiens
SEQUENCE: 1
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 2            moltype = DNA  length = 345
FEATURE                 Location/Qualifiers
source                  1..345
                        mol_type = genomic DNA
                        organism = Homo sapiens
SEQUENCE: 2
aactgggtga atgtaataag tgatttgaaa aaaattgaag atcttattca atctatgcat  60
attgatgcta ctttatatac ggaaagtgat gttcacccca gttgcaaagt aacagcaatg  120
aagtgctttc tcttggagtt acaagttatt tcacttgagt ccggagatgc aagtattcat  180
gatacagtag aaaatctgat catcctagca aacaacagtt tgtcttctaa tgggaatgta  240
acagaatctg gatgcaaaga atgtgaggaa ctggaggaaa aaaatattaa agaatttttg  300
cagagttttg tacatattgt ccaaatgttc atcaacactt cttga                 345
```

```
SEQ ID NO: 3              moltype = AA  length = 20
FEATURE                   Location/Qualifiers
source                    1..20
                          mol_type = protein
                          organism = synthetic construct
SEQUENCE: 3
GGGGSGGGGS GGGGSGGGGS                                               20

SEQ ID NO: 4              moltype = DNA  length = 1563
FEATURE                   Location/Qualifiers
source                    1..1563
                          mol_type = other DNA
                          organism = synthetic construct
SEQUENCE: 4
accaccatgg agacagacac actcctgtta tgggtactgc tgctctgggt tccaggttcc    60
accggtcagt cagtgacgca gcccgatgct cgcgtcactg tctctgaagg agcctctctg   120
cagctgagat gcaagtattc ctactctggg acaccttatc tgttctggta tgtccagtac   180
ccgcggcagg ggctgcagct gctcctcaag tactattcag agacccagt ggttcaagga    240
gtgaatggct tcgaggctga gttcagcaag agtaactctt ccttccacct gcggaaagcc   300
tctgtgcact ggagcgactc tgctgtgtac ttctgtgttt tgagcgagga tagcaactat   360
cagttgatct ggggctctgg gaccaagcta attataaagc cagacactag tggtggcggt   420
ggcagcggcg gtggtggttc cggtggcggc ggttctggcg gtggcggttc ctcgagcaat   480
tcaaaagtca ttcagactcc aagatatctg gtgaaaggc aaggacaaaa agcaaagatg    540
aggtgtatcc tgaaaagggg acatccagtt gtattctggt atcaacaaaa taagaacaat   600
gagtttaaat ttttgattaa cttttcagaat caagaagttc tcagcaaat agacatgact   660
gaaaaacgat tctctgctga gtgtccttca aactcacctt gcagcctaga aattcagtcc   720
tctgaggcag gagactcagc actgtacctc tgtgccagca gtctgtcagg ggcggcaca    780
gaagtttttt tggtaaagg aaccagactc acagttgtag aggacctgaa caaggtgttc   840
ccaccgagg tcgctgtgtt tgagccatca gaagcagaga tctcccacac ccaaaagct    900
acactggtgt gcctggccac aggcttcttc cctgaccacg tggagctgag ctggtgggtg   960
aatgggaagg aggtgcacag tggggtcagc acggaccccg agcccctcaa ggagcagccc  1020
gccctcaatg actccagata ctgcctgagc agccgcctga gggtctcggc cacctctgg   1080
cagaacccc gcaaccactt ccgctgtcaa gtccagttct acgggctctc ggagaatgac  1140
gagtggaccc aggataggc caaaccgtc acccagatcg tcagcgccga ggcctgggt    1200
agcagacgg ttaacaactg ggtgaatgta taagtgatt tgaaaaaaat tgaagatctt    1260
attcaatcta tgcatattga tgctacttta tatacgaaa gtgatgttca ccccagttgc   1320
aaagtaacag caatgaagtg ctttctcttg gagttacaag ttatttcact tgagtccgga  1380
gatgcaagta ttcatgatac agtagaaaat ctgatcatcc tagcaaacaa cagtttgtct  1440
tctaatggga atgtaacaga atctggatgc aaagaatgtg aggaactgga ggaaaaaaat  1500
attaaagaat ttttgcagag ttttgtacat attgtccaaa tgttcatcaa cacttcttga  1560
taa                                                                1563

SEQ ID NO: 5              moltype = AA  length = 517
FEATURE                   Location/Qualifiers
source                    1..517
                          mol_type = protein
                          organism = synthetic construct
SEQUENCE: 5
METDTLLLWV LLLWVPGSTG QSVTQPDARV TVSEGASLQL RCKYSYSGTP YLFWYVQYPR    60
QGLQLLLKYY SGDPVVQGVN GFEAEFSKSN SSFHLRKASV HWSDSAVYFC VLSEDSNYQL   120
IWGSGTKLII KPDTSGGGGS GGGGSGGGGS GGGGSSNSK VIQTPRYLVK GQGQKAKMRC    180
IPEKGHPVVF WYQQNKNNEF KFLINFQNQE VLQQIDMTEK RFSAECPSNS PCSLEIQSSE   240
AGDSALYLCA SSLSGGGTEV FFGKGTRLTV VEDLNKVFPP EVAVFEPSEA EISHTQKATL   300
VCLATGFFPD HVELSWWVNG KEVHSGVSTD PQPLKEQPAL NDSRYCLSSR LRVSATFWQN   360
PRNHFRCQVQ FYGLSENDEW TQDRAKPVTQ IVSAEAWGRA DVNNWVNVIS DLKKIEDLIQ   420
SMHIDATLYT ESDVHPSCKV TAMKCFLLEL QVISLESGDA SIHDTVENLI ILANNSLSSN   480
GNVTESGCKE CEELEEKNIK EFLQSFVHIV QMFINTS                            517

SEQ ID NO: 6              moltype = DNA  length = 1614
FEATURE                   Location/Qualifiers
source                    1..1614
                          mol_type = other DNA
                          organism = synthetic construct
SEQUENCE: 6
accaccatgg agacagacac actcctgtta tgggtactgc tgctctgggt tccaggttcc    60
accggtcagt cagtgacgca gcccgatgct cgcgtcactg tctctgaagg agcctctctg   120
cagctgagat gcaagtattc ctactctggg acaccttatc tgttctggta tgtccagtac   180
ccgcggcagg ggctgcagct gctcctcaag tactattcag agacccagt ggttcaagga    240
gtgaatggct tcgaggctga gttcagcaag agtaactctt ccttccacct gcggaaagcc   300
tctgtgcact ggagcgactc tgctgtgtac ttctgtgttt tgagcgagga tagcaactat   360
cagttgatct ggggctctgg gaccaagcta attataaagc cagacactag tggtggcggt   420
ggcagcggcg gtggtggttc cggtggcggc ggttctggcg gtggcggttc ctcgagcaat   480
tcaaaagtca ttcagactcc aagatatctg gtgaaaggc aaggacaaaa agcaaagatg    540
aggtgtatcc tgaaaagggg acatccagtt gtattctggt atcaacaaaa taagaacaat   600
gagtttaaat ttttgattaa cttttcagaat caagaagttc tcagcaaat agacatgact   660
gaaaaacgat tctctgctga gtgtccttca aactcacctt gcagcctaga aattcagtcc   720
tctgaggcag gagactcagc actgtacctc tgtgccagca gtctgtcagg ggcggcaca    780
gaagtttttt tggtaaagg aaccagactc acagttgtag aggacctgaa caaggtgttc   840
```

```
ccacccgagg tcgctgtgtt tgagccatca gaagcagaga tctcccacac ccaaaaggcc    900
acactggtgt gcctggccac aggcttcttc cctgaccacg tggagctgag ctggtgggtg    960
aatgggaagg aggtgcacag tggggtcagc acggacccgc agcccctcaa ggagcagccc   1020
gccctcaatg actccagata ctgcctgagc agccgcctga gggtctcggc caccttctgg   1080
cagaaccccc gcaaccactt ccgctgtcaa gtccagttct acgggctctc ggagaatgac   1140
gagtggaccc aggatagggc caaacccgtc acccagatcg tcagcgccga ggctgggggt   1200
agagcagacg ttaacgagcc caaatcttct gacaaaactc acacatctcc accgtctcca   1260
acgcgtaact gggtgaatgt aataagtgat ttgaaaaaaa ttgaagatct tattcaatct   1320
atgcatattg atgctacttt atatacggaa agtgatgttc acccagttg caaagtaaca   1380
gcaatgaagt gctttctctt ggagttacaa gttatttcac ttgagtccgg agatgcaagt   1440
attcatgata cagtagaaaa tctgatcatc ctagcaaaca acagtttgtc ttctaatggg   1500
aatgtaacag aatctggatg caaagaatgt gaggaactgg aggaaaaaaa tattaaagaa   1560
tttttgcaga gttttgtaca tattgtccaa atgttcatca cacttcttg ataa          1614

SEQ ID NO: 7              moltype = AA   length = 534
FEATURE                   Location/Qualifiers
source                    1..534
                          mol_type = protein
                          organism = synthetic construct
SEQUENCE: 7
METDTLLLWV LLLWVPGSTG QSVTQPDARV TVSEGASLQL RCKYSYSGTP YLFWYVQYPR    60
QGLQLLLKYY SGDPVVQGVN GFEAEFSKSN SSFHLRKASV HWSDSAVYFC VLSEDSNYQL   120
IWGSGTKLII KPDTSGGGGS GGGGSGGGGS GGGGSSSNSK VIQTPRYLVK GQGQKAKMRC   180
IPEKGHPVVF WYQQNKNNEF KFLINFQNQE VLQQIDMTEK RFSAECPSNS PCSLEIQSSE   240
AGDSALYLCA SSLSGGGTEV FFGKGTRLTV VEDLNKVFPP EVAVFEPSEA EISHTQKATL   300
VCLATGFFPD HVELSWWVNG KEVHSGVSTD PQPLKEQPAL NDSRYCLSSR LRVSATFWQN   360
PRNHFRCQVQ FYGLSENDEW TQDRAKPVTQ IVSAEAWGRA DVNEPKSSDK THTSPPSPTR   420
NWVNVISDLK KIEDLIQSMH IDATLYTESD VHPSCKVTAM KCFLLELQVI SLESGDASIH   480
DTVENLIILA NNSLSSNGNV TESGCKECEE LEEKNIKEFL QSFVHIVQMF INTS         534

SEQ ID NO: 8              moltype = DNA   length = 1647
FEATURE                   Location/Qualifiers
source                    1..1647
                          mol_type = other DNA
                          organism = synthetic construct
SEQUENCE: 8
accaccatgg agacagacac actcctgtta tgggtactgc tgctctgggt tccaggttcc     60
accggtcagt cagtgacgca gcccgatgct cgcgtcactg tctctgaagg agcctctctg    120
cagctgagat gcaagtattc ctactctggg acaccttatc tgttctggta tgtccagtac    180
ccgcggcagg ggctgcagct gctcctcaag tactattcag gagacccagt ggttcaagga    240
gtgaatggct tcgaggctga gttcagcaag agtaactctt ccttccacct gcggaaagcc    300
tctgtgcact ggagcgactc tgctgtgtac ttctgtgttt tgagcgagga tagcaactat    360
cagttgatct ggggctctgg gaccaagcta attataaagc cagacactag tggtggcggt    420
ggcagcggcg gtggtggttc cggtggcggc ggttctggcg gtggcggttc ctcgagcaat    480
tcaaaagtca ttcagactcc aagatatctg gtgaaaggc aaggacaaaa agcaaagatg    540
aggtgtatcc ctgaaaaggg acatccagtt gtattctgga tcaacaaaa taagaacaat    600
gagtttaaat tttgattaa cttttcagaat caagaagttc ttcagcaaat agacatgact    660
gaaaaacgat tctctgctga gtgtccttca aactcacctt gcagcctaga aattcagtcc    720
tctgaggcag gagactcagc actgtaccc tgtgccagca gtctgtcagg gggcggcaca    780
gaagtttttc ttggtaaagg aaccagactc acagttgtag aggacctgaa caaggtgttc    840
ccacccgagg tcgctgtgtt tgagccatca gaagcagaga tctcccacac ccaaaaggcc    900
acactggtgt gcctggccac aggcttcttc cctgaccacg tggagctgag ctggtgggtg    960
aatgggaagg aggtgcacag tggggtcagc acggacccgc agcccctcaa ggagcagccc   1020
gccctcaatg actccagata ctgcctgagc agccgcctga gggtctcggc caccttctgg   1080
cagaaccccc gcaaccactt ccgctgtcaa gtccagttct acgggctctc ggagaatgac   1140
gagtggaccc aggatagggc caaacccgtc acccagatcg tcagcgccga ggctgggggt   1200
agagcagacg ttaacatcac gtgccctccc ccatgtccg tggaacacgc agacatctgg   1260
gtcaagagct acagcttgta ctccaggag cggtacattt gtaactctgg tttcaagcgt   1320
aaagccggca cgtccagcct gacggagtgc gtgttgaaca aggccacgaa tgtcgcccac   1380
tggacaaccc ccagtctcaa atgcattaga cccgcagctt catctcccag ctcaaacaac   1440
acagcggcca aacagcagc tattgtcccg ggctcccagc tgatgccttc aaaatcacct   1500
tccacaggaa ccacagagat aagcagtcat gagtcctccc acggcacccc ctctcagaca   1560
acagccaaga actgggaact cacagcatcc gcctccacc agccgccagg tgtgtatcca   1620
cagggccaca gcgacaccac ttgataa                                      1647

SEQ ID NO: 9              moltype = AA   length = 545
FEATURE                   Location/Qualifiers
source                    1..545
                          mol_type = protein
                          organism = synthetic construct
SEQUENCE: 9
METDTLLLWV LLLWVPGSTG QSVTQPDARV TVSEGASLQL RCKYSYSGTP YLFWYVQYPR    60
QGLQLLLKYY SGDPVVQGVN GFEAEFSKSN SSFHLRKASV HWSDSAVYFC VLSEDSNYQL   120
IWGSGTKLII KPDTSGGGGS GGGGSGGGGS GGGGSSSNSK VIQTPRYLVK GQGQKAKMRC   180
IPEKGHPVVF WYQQNKNNEF KFLINFQNQE VLQQIDMTEK RFSAECPSNS PCSLEIQSSE   240
AGDSALYLCA SSLSGGGTEV FFGKGTRLTV VEDLNKVFPP EVAVFEPSEA EISHTQKATL   300
VCLATGFFPD HVELSWWVNG KEVHSGVSTD PQPLKEQPAL NDSRYCLSSR LRVSATFWQN   360
PRNHFRCQVQ FYGLSENDEW TQDRAKPVTQ IVSAEAWGRA DVNITPPPM SVEHADIWVK    420
SYSLYSRERY ICNSGFKRKA GTSSLTECVL NKATNVAHWT TPSLKCIRPA ASSPSSNNTA   480
```

```
ATTAAIVPGS QLMPSKSPST GTTEISSHES SHGTPSQTTA KNWELTASAS HQPPGVYPQG   540
HSDTT                                                             545

SEQ ID NO: 10             moltype = DNA  length = 1410
FEATURE                   Location/Qualifiers
source                    1..1410
                          mol_type = other DNA
                          organism = synthetic construct
SEQUENCE: 10
accaccatgg agacagacac actcctgtta tgggtactgc tgctctgggt tccaggttcc   60
accggtcagt cagtgacgca gcccgatgct cgcgtcactg tctctgaagg agcctctctg  120
cagctgagat gcaagtattc ctactctggg acaccttatc tgttctggta tgtccagtac  180
ccgcggcagg ggctgcagct gctcctcaag tactattcag agacccagt ggttcaagga   240
gtgaatggct cgaggctga gttcagcaag agtaactctt ccttccacct gcggaaagcc   300
tctgtgcact ggagcgactc tgctgtgtac ttctgtgttt gagcgagga tagcaactat   360
cagttgatct ggggctctgg gaccaagcta attataaagc cagacactag tggtggcggt   420
ggcagcggcg gtggtggttc cggtggcggc ggttctggcg gtggcggttc ctcgagcaat   480
tcaaaagtca ttcagactcc aagatatctg gtgaaaggca aaggacaaaa agcaaagatg   540
aggtgtatcc ctgaaaaggg acatccagtt gtattctggt atcaacaaaa taagaacaat   600
gagtttaaat ttttgattaa ctttcagaat caagaagttc ttcagcaaat agacatgact   660
gaaaaacgat tctctgctga gtgtccttca aactcacctt gcagcctaga aattcagtcc   720
tctgaggcag gagactcagc actgtacctc tgtgccagca gtctgtcagg gggcggcaca   780
gaagttttct ttggtaaagg aaccagactc acagttgtag aggacctgaa caaggtgttc   840
ccacccgagg tcgctgtgtt tgagccatca gaagcagaga tctcccacac ccaaaaggcc   900
acactggtgt gcctggccac aggcttcttc cctgaccacg tggagctgag ctggtgggtg   960
aatgggaagg aggtgcacag tggggtcagc acggacccgc agcccctcaa ggagcagccc  1020
gccctcaatg actccagata ctgcctgagc agccgcctga gggtctcggc caccttctgg  1080
cagaaccccc gcaaccactt ccgctgtcaa gtccagttct acgggctctc ggagaatgac  1140
gagtggaccc aggatagggc caaacccgtc acccagatcg tcagcgccga ggcctggggt  1200
agagcagacg ttaacatcac gtgccctccc cccatgtccg tggaacacgc agacatctgg  1260
gtcaagagct acagcttgta ctccagggag cggtacattt gtaactctgg tttcaagcgt  1320
aaagccggca cgtccagcct gacggagtgc gtgttgaaca aggccacgaa tgtcgcccac  1380
tggacaaccc cagtctcaa atgcattaga                                    1410

SEQ ID NO: 11             moltype = AA  length = 468
FEATURE                   Location/Qualifiers
source                    1..468
                          mol_type = protein
                          organism = synthetic construct
SEQUENCE: 11
METDTLLLWV LLLWVPGSTG QSVTQPDARV TVSEGASLQL RCKYSYSGTP YLFWYVQYPR   60
QGLQLLLKYY SGDPVVQGVN GFEAEFSKSN SSFHLRKASV HWSDSAVYFC VLSEDSNYQL  120
IWGSGTKLII KPDTSGGGGS GGGGSGGGGS GGGGSSSNSK VIQTPRYLVK GQGQKAKMRC  180
IPEKGHPVVF WYQQKNNEF KFLINFQNQE VLQQIDMTEK RFSAECPSNS PCSLEIQSSE   240
AGDSALYLCA SSLSGGGTEV FFGKGTRLTV VEDLNKVFPP EVAVFEPSEA EISHTQKATL  300
VCLATGFFPD HVELSWWVNG KEVHSGVSTD PQPLKEQPAL NDSRYCLSSR LRVSATFWQN  360
PRNHFRCQVQ FYGLSENDEW TQDRAKPVTQ IVSAEAWGRA DVNITCPPPM SVEHADIWVK  420
SYSLYSRERY ICNSGFKRKA GTSSLTECVL NKATNVAHWT TPSLKCIR               468

SEQ ID NO: 12             moltype = DNA  length = 1467
FEATURE                   Location/Qualifiers
source                    1..1467
                          mol_type = other DNA
                          organism = synthetic construct
SEQUENCE: 12
accaccatgg agacagacac actcctgtta tgggtactgc tgctctgggt tccaggttcc   60
accggtcagt cagtgacgca gcccgatgct cgcgtcactg tctctgaagg agcctctctg  120
cagctgagat gcaagtattc ctactctggg acaccttatc tgttctggta tgtccagtac  180
ccgcggcagg ggctgcagct gctcctcaag tactattcag agacccagt ggttcaagga   240
gtgaatggct cgaggctga gttcagcaag agtaactctt ccttccacct gcggaaagcc   300
tctgtgcact ggagcgactc tgctgtgtac ttctgtgttt gagcgagga tagcaactat   360
cagttgatct ggggctctgg gaccaagcta attataaagc cagacactag tggtggcggt   420
ggcagcggcg gtggtggttc cggtggcggc ggttctggcg gtggcggttc ctcgagcaat   480
tcaaaagtca ttcagactcc aagatatctg gtgaaaggca aaggacaaaa agcaaagatg   540
aggtgtatcc ctgaaaaggg acatccagtt gtattctggt atcaacaaaa taagaacaat   600
gagtttaaat ttttgattaa ctttcagaat caagaagttc ttcagcaaat agacatgact   660
gaaaaacgat tctctgctga gtgtccttca aactcacctt gcagcctaga aattcagtcc   720
tctgaggcag gagactcagc actgtacctc tgtgccagca gtctgtcagg gggcggcaca   780
gaagttttct ttggtaaagg aaccagactc acagttgtag aggacctgaa caaggtgttc   840
ccacccgagg tcgctgtgtt tgagccatca gaagcagaga tctcccacac ccaaaaggcc   900
acactggtgt gcctggccac aggcttcttc cctgaccacg tggagctgag ctggtgggtg   960
aatgggaagg aggtgcacag tggggtcagc acggacccgc agcccctcaa ggagcagccc  1020
gccctcaatg actccagata ctgcctgagc agccgcctga gggtctcggc caccttctgg  1080
cagaaccccc gcaaccactt ccgctgtcaa gtccagttct acgggctctc ggagaatgac  1140
gagtggaccc aggatagggc caaacccgtc acccagatcg tcagcgccga ggcctggggt  1200
agagcagacg ttaacgagcc caaatcttct gacaaaactc acacatctcc accgtctcca  1260
acgcgtatca cgtgccctcc ccccatgtcc gtggaacacg cagacatctg gtcaagagc   1320
tacagcttgt actccaggga gcggtacatt tgtaactctg gtttcaagcg taaagccggc  1380
```

```
acgtccagcc tgacggagtg cgtgttgaac aaggccacga atgtcgccca ctggacaacc    1440
cccagtctca aatgcattag atgataa                                         1467

SEQ ID NO: 13            moltype = AA  length = 485
FEATURE                  Location/Qualifiers
source                   1..485
                         mol_type = protein
                         organism = synthetic construct
SEQUENCE: 13
METDTLLLWV LLLWVPGSTG QSVTQPDARV TVSEGASLQL RCKYSYSGTP YLFWYVQYPR     60
QGLQLLLKYY SGDPVVQGVN GFEAEFSKSN SSPHLRKASV HWSDSAVYFC VLSEDSNYQL    120
IWGSGTKLII KPDTSGGGGS GGGGSGGGGS GGGGSSSNSK VIQTPRYLVK GQGQKAKMRC    180
IPEKGHPVVF WYQQNKNNEF KFLINFQNQE VLQQIDMTEK RFSAECPSNS PCSLEIQSSE    240
AGDSALYLCA SSLSGGGTEV FFGKGTRLTV VEDLNKVFPP EVAVFEPSEA EISHTQKATL    300
VCLATGFFPD HVELSWWVNG KEVHSGVSTD PQPLKEQPAL NDSRYCLSSR LRVSATFWQN    360
PRNHFRCQVQ FYGLSENDEW TQDRAKPVTQ IVSAEAWGRA DVNEPKSSDK THTSPPSPTR    420
ITCPPPMSVE HADIWVKSYS LYSRERYICN SGFKRKAGTS SLTECVLNKA TNVAHWTTPS    480
LKCIR                                                                485

SEQ ID NO: 14            moltype = DNA  length = 1614
FEATURE                  Location/Qualifiers
source                   1..1614
                         mol_type = other DNA
                         organism = synthetic construct
SEQUENCE: 14
accaccatgg agacagacac actcctgtta tgggtactgc tgctctgggt tccaggttcc     60
accggtcagt cagtgacgca gcccgatgct cgcgtcactg tctctgaagg agcctctctg    120
cagctgagat gcaagtattc ctactctggg acacccttat cgttctggta tgtccagtac    180
ccgcggcagg ggctgcagct gctcctcaag tactattcag agacccagt ggttcaagga     240
gtgaattggc tcgaggctga gttcagcaag agtaactctt ccttccacct gcggaaagcc    300
tctgtgcact ggagcgactc tgctgtgtac ttctgtgttt tgagcgagga tagcaactat    360
cagttgatct ggggctctgg gaccaagcta attataaagc cagacactag tggtggcggt    420
ggcagcggcg gtggtggttc cggtggcggc ggttctggcg gtggcggttc ctcgagcaat    480
tcaaaagtca ttcagactcc aagatatctg gtgaaagggc aaggacaaaa agcaaagatg    540
aggtgtatcc ctgaaaaggg acatccagtt gtattctggt atcaacaaaa taagaacaat    600
gagtttaaat ttttgattaa ctttcagaat caagaagttc ttcagcaaat agacatgact    660
gaaaaacgat tctctgctga gtgtccttca aactcacctt gcagcctaga aattcagtcc    720
tctgaggcag gagactcagc actgtacctc tgtgccagca gtctgtcagg ggcggcaca    780
gaagttttct ttggtaaagg aaccagactc acagttgtag gaggacctgaa caaggtgttc    840
ccacccgagg tcgctgtgtt tgagccatca gaagcagaga tctcccacac ccaaaaggcc    900
acactggtgt gcctggccac aggcttcttc cctgaccacg tggagctgag ctggtgggtg    960
aatgggaagg aggtgcacag tggggtcagc acggaccgc agccctcaa ggagcagcc     1020
gccctcaatg actccagata ctgcctgagc agccgcctga gggtctcggc caccttctgg   1080
cagaacccc gcaaccactt ccgctgtcaa gtccagttct acgggctctc ggagaatgac   1140
gagtggaccc aggatagggc caaacccgtc acccagatcg tcagcgccga ggcctggggt   1200
agagcagacg ttaacgagcc caaatcttct gacaaaactc acacatctcc accgtctcca   1260
acgcgtaact gggtgaatgt aataagtgct ttgaaaaaa ttgaagatct tattcaatct   1320
atgcatattg atgctacttt atatacgaaa agtgatgttc accccagttg caaagtaaca   1380
gcaatgaagt gctttctctt ggagttacaa gttatttcac ttgagtccgg agatgcaagt   1440
attcatgata cagtagaaaa tctgatcatc ctagcaaaca acagtttgtc ttctaatggg   1500
aatgtaacag aatctggatg caaagaatgt gaggaactgg aggaaaaaaa tattaaagaa   1560
tttttgcaga gttttgtaca tattgtccaa atgttcatca cacttcttg ataa           1614

SEQ ID NO: 15            moltype = DNA  length = 1614
FEATURE                  Location/Qualifiers
source                   1..1614
                         mol_type = other DNA
                         organism = synthetic construct
SEQUENCE: 15
accaccatgg agacagacac actcctgtta tgggtactgc tgctctgggt tccaggttcc     60
accggtcagt cagtgacgca gcccgatgct cgcgtcactg tctctgaagg agcctctctg    120
cagctgagat gcaagtattc ctactctggg acacccttat cgttctggta tgtccagtac    180
ccgcggcagg ggctgcagct gctcctcaag tactattcag agacccagt ggttcaagga     240
gtgaattggc tcgaggctga gttcagcaag agtaactctt ccttccacct gcggaaagcc    300
tctgtgcact ggagcgactc tgctgtgtac ttctgtgttt tgagcgagga tagcaactat    360
cagttgatct ggggctctgg gaccaagcta attataaagc cagacactag tggtggcggt    420
ggcagcggcg gtggtggttc cggtggcggc ggttctggcg gtggcggttc ctcgagcaat    480
tcaaaagtca ttcagactcc aagatatctg gtgaaagggc aaggacaaaa agcaaagatg    540
aggtgtatcc ctgaaaaggg acatccagtt gtattctggt atcaacaaaa taagaacaat    600
gagtttaaat ttttgattaa ctttcagaat caagaagttc ttcagcaaat agacatgact    660
gaaaaacgat tctctgctga gtgtccttca aactcacctt gcagcctaga aattcagtcc    720
tctgaggcag gagactcagc actgtacctc tgtgccagca gtctgtcagg ggcggcaca    780
gaagttttct ttggtaaagg aaccagactc acagttgtag gaggacctgaa caaggtgttc    840
ccacccgagg tcgctgtgtt tgagccatca gaagcagaga tctcccacac ccaaaaggcc    900
acactggtgt gcctggccac aggcttcttc cctgaccacg tggagctgag ctggtgggtg    960
aatgggaagg aggtgcacag tggggtcagc acggaccgc agccctcaa ggagcagcc     1020
gccctcaatg actccagata ctgcctgagc agccgcctga gggtctcggc caccttctgg   1080
cagaacccc gcaaccactt ccgctgtcaa gtccagttct acgggctctc ggagaatgac   1140
gagtggaccc aggatagggc caaacccgtc acccagatcg tcagcgccga ggcctgggt    1200
```

```
agagcagacg ttaacgagcc caaatcttct gacaaaactc acacatctcc accgtctcca  1260
acgcgtaact gggtgaatgt aataagtaat ttgaaaaaaa ttgagatctt tattcaatct  1320
atgcatattg atgctacttt atatacgaaa agtgatgttc accccagttg caaagtaaca  1380
gcaatgaagt gctttctctt ggagttacaa gttatttcac ttgagtccgg agatgcaagt  1440
attcatgata cagtagaaaa tctgatcatc ctagcaaaca acagtttgtc ttctaatggg  1500
aatgtaacag aatctggatg caaagaatgt gaggaactgg aggaaaaaaa tattaaagaa  1560
tttttgcaga gttttgtaca tattgtccaa atgttcatca acacttcctg ataa         1614

SEQ ID NO: 16             moltype = AA   length = 534
FEATURE                   Location/Qualifiers
source                    1..534
                          mol_type = protein
                          organism = synthetic construct
SEQUENCE: 16
METDTLLLWV LLLWVPGSTG QSVTQPDARV TVSEGASLQL RCKYSYSGTP YLFWYVQYPR   60
QGLQLLLKYY SGDPVVQGVN GFEAEFSKSN SSFHLRKASV HWSDSAVYFC VLSEDSNYQL  120
IWGSGTKLII KPDTSGGGGS GGGGSGGGGS GGGGSSSNSK VIQTPRYLVK GQGQKAKMRC  180
IPEKGHPVVF WYQQNKNNEF KFLINFQNQE VLQQIDMTEK RFSAECPSNS PCSLEIQSSE  240
AGDSALYLCA SSLSGGGTEV FFGKGTRLTV VEDLNKVFPP EVAVFEPSEA EISHTQKATL  300
VCLATGFFPD HVELSWWVNG KEVHSGVSTD PQPLKEQPAL NDSRYCLSSR LRVSATFWQN  360
PRNHFRCQVQ FYGLSENDEW TQDRAKPVTQ IVSAEAWGRA DVNEPKSSDK THTSPPSPTR  420
NWVNVISALK KIEDLIQSMH IDATLYTESD VHPSCKVTAM KCFLLELQVI SLESGDASIH  480
DTVENLIILA NNSLSSNGNV TESGCKECEE LEEKNIKEFL QSFVHIVQMF INTS        534

SEQ ID NO: 17             moltype = AA   length = 534
FEATURE                   Location/Qualifiers
source                    1..534
                          mol_type = protein
                          organism = synthetic construct
SEQUENCE: 17
METDTLLLWV LLLWVPGSTG QSVTQPDARV TVSEGASLQL RCKYSYSGTP YLFWYVQYPR   60
QGLQLLLKYY SGDPVVQGVN GFEAEFSKSN SSFHLRKASV HWSDSAVYFC VLSEDSNYQL  120
IWGSGTKLII KPDTSGGGGS GGGGSGGGGS GGGGSSSNSK VIQTPRYLVK GQGQKAKMRC  180
IPEKGHPVVF WYQQNKNNEF KFLINFQNQE VLQQIDMTEK RFSAECPSNS PCSLEIQSSE  240
AGDSALYLCA SSLSGGGTEV FFGKGTRLTV VEDLNKVFPP EVAVFEPSEA EISHTQKATL  300
VCLATGFFPD HVELSWWVNG KEVHSGVSTD PQPLKEQPAL NDSRYCLSSR LRVSATFWQN  360
PRNHFRCQVQ FYGLSENDEW TQDRAKPVTQ IVSAEAWGRA DVNEPKSSDK THTSPPSPTR  420
NWVNVISNLK KIEDLIQSMH IDATLYTESD VHPSCKVTAM KCFLLELQVI SLESGDASIH  480
DTVENLIILA NNSLSSNGNV TESGCKECEE LEEKNIKEFL QSFVHIVQMF INTS        534

SEQ ID NO: 18             moltype = AA   length = 10
FEATURE                   Location/Qualifiers
source                    1..10
                          mol_type = protein
                          organism = synthetic construct
SEQUENCE: 18
ASGGGGSGGG                                                          10

SEQ ID NO: 19             moltype = DNA   length = 23
FEATURE                   Location/Qualifiers
source                    1..23
                          mol_type = other DNA
                          organism = synthetic construct
SEQUENCE: 19
caccttgcca tagccagctc ttc                                           23

SEQ ID NO: 20             moltype = DNA   length = 24
FEATURE                   Location/Qualifiers
source                    1..24
                          mol_type = other DNA
                          organism = synthetic construct
SEQUENCE: 20
gtctaagcag cagagtgatg tttg                                          24

SEQ ID NO: 21             moltype = DNA   length = 30
FEATURE                   Location/Qualifiers
source                    1..30
                          mol_type = other DNA
                          organism = synthetic construct
SEQUENCE: 21
tggttaacaa ctgggtgaat gtaataagtg                                    30

SEQ ID NO: 22             moltype = DNA   length = 36
FEATURE                   Location/Qualifiers
source                    1..36
                          mol_type = other DNA
                          organism = synthetic construct
SEQUENCE: 22
acgcgtttat caagaagtgt tgatgaacat ttggac                             36
```

```
SEQ ID NO: 23              moltype = DNA   length = 28
FEATURE                    Location/Qualifiers
source                     1..28
                           mol_type = other DNA
                           organism = synthetic construct
SEQUENCE: 23
tggtgggtta acgagcccaa atcttctg                                              28

SEQ ID NO: 24              moltype = DNA   length = 29
FEATURE                    Location/Qualifiers
source                     1..29
                           mol_type = other DNA
                           organism = synthetic construct
SEQUENCE: 24
attattacgc gttggagacg gtggagatg                                             29

SEQ ID NO: 25              moltype = DNA   length = 32
FEATURE                    Location/Qualifiers
source                     1..32
                           mol_type = other DNA
                           organism = synthetic construct
SEQUENCE: 25
tgagtgatcg ataccaccat ggagacagac ac                                         32

SEQ ID NO: 26              moltype = DNA   length = 25
FEATURE                    Location/Qualifiers
source                     1..25
                           mol_type = other DNA
                           organism = synthetic construct
SEQUENCE: 26
tggtggacgc gtaactgggt gaatg                                                 25

SEQ ID NO: 27              moltype = DNA   length = 32
FEATURE                    Location/Qualifiers
source                     1..32
                           mol_type = other DNA
                           organism = synthetic construct
SEQUENCE: 27
tggtggtcta gaattatcaa gaagtgttga tg                                         32

SEQ ID NO: 28              moltype = DNA   length = 20
FEATURE                    Location/Qualifiers
source                     1..20
                           mol_type = other DNA
                           organism = synthetic construct
SEQUENCE: 28
agtccagcgg tgtcctgtgg                                                       20

SEQ ID NO: 29              moltype = DNA   length = 31
FEATURE                    Location/Qualifiers
source                     1..31
                           mol_type = other DNA
                           organism = synthetic construct
SEQUENCE: 29
tgacgcgttt aagtggtgtc gctgtgccct g                                          31

SEQ ID NO: 30              moltype = DNA   length = 29
FEATURE                    Location/Qualifiers
source                     1..29
                           mol_type = other DNA
                           organism = synthetic construct
SEQUENCE: 30
tggttaacat cacgtgccct cccccatg                                              29

SEQ ID NO: 31              moltype = DNA   length = 35
FEATURE                    Location/Qualifiers
source                     1..35
                           mol_type = other DNA
                           organism = synthetic construct
SEQUENCE: 31
ttgttgacgc gtttatctaa tgcatttgag actgg                                      35

SEQ ID NO: 32              moltype = DNA   length = 25
FEATURE                    Location/Qualifiers
source                     1..25
                           mol_type = other DNA
                           organism = synthetic construct
```

```
SEQUENCE: 32
taataaacgc gtatcacgtg ccctc                                                 25

SEQ ID NO: 33           moltype = DNA   length = 31
FEATURE                 Location/Qualifiers
source                  1..31
                        mol_type = other DNA
                        organism = synthetic construct
SEQUENCE: 33
tggtggtcta gattatcatc taatgcattt g                                          31

SEQ ID NO: 34           moltype = DNA   length = 32
FEATURE                 Location/Qualifiers
source                  1..32
                        mol_type = other DNA
                        organism = synthetic construct
SEQUENCE: 34
tgagtgtccg gaaccaccat ggagacagac ac                                         32

SEQ ID NO: 35           moltype = DNA   length = 35
FEATURE                 Location/Qualifiers
source                  1..35
                        mol_type = other DNA
                        organism = synthetic construct
SEQUENCE: 35
ttgttggcgg ccgcttatca tctaatgcat ttgag                                      35

SEQ ID NO: 36           moltype = DNA   length = 34
FEATURE                 Location/Qualifiers
source                  1..34
                        mol_type = other DNA
                        organism = synthetic construct
SEQUENCE: 36
tgagtgttcg aattatcaag aagtgttgat gaac                                       34

SEQ ID NO: 37           moltype = DNA   length = 33
FEATURE                 Location/Qualifiers
source                  1..33
                        mol_type = other DNA
                        organism = synthetic construct
SEQUENCE: 37
ttgttggcgg ccgcttatca agtggtgtcg ctg                                        33

SEQ ID NO: 38           moltype = DNA   length = 42
FEATURE                 Location/Qualifiers
source                  1..42
                        mol_type = other DNA
                        organism = synthetic construct
SEQUENCE: 38
agatcttcaa tttttttcaa mkhacttatt acattcaccc ag                              42

SEQ ID NO: 39           moltype = DNA   length = 42
FEATURE                 Location/Qualifiers
source                  1..42
                        mol_type = other DNA
                        organism = synthetic construct
SEQUENCE: 39
actgggtgaa tgtaataagt dmkttgaaaa aaattgaaga tc                              42

SEQ ID NO: 40           moltype = DNA   length = 31
FEATURE                 Location/Qualifiers
source                  1..31
                        mol_type = other DNA
                        organism = synthetic construct
SEQUENCE: 40
tggtggtcta gattatcaag aagtgttgat g                                          31
```